United States Patent

Durant et al.

[11] Patent Number: 6,147,063
[45] Date of Patent: Nov. 14, 2000

[54] THERAPEUTIC SUBSTITUTED GUANIDINES

[75] Inventors: Graham J. Durant, Cambridge; Sharad Magar, Somerville; Lain-Yen Hu, Bedford, all of Mass.

[73] Assignee: Cambridge NeuroScience, Inc., Norwood, Mass.

[21] Appl. No.: 08/458,741

[22] Filed: Jun. 2, 1995

Related U.S. Application Data

[63] Continuation of application No. PCT/US94/06008, May 27, 1994, abandoned, which is a continuation-in-part of application No. 08/068,522, May 27, 1993, abandoned.

[51] Int. Cl.⁷ .................. A61K 31/18; A61K 31/155; A61K 31/445; A61K 31/655
[52] U.S. Cl. .................. 514/150; 514/311; 514/237.8; 514/353; 514/447; 514/459; 514/472; 514/605; 514/633; 514/634; 544/164; 546/134; 546/306; 549/68; 549/424; 549/480; 552/8; 564/99; 564/229; 564/238; 564/239
[58] Field of Search .................. 514/150, 311, 514/605, 633, 634, 237.8, 353, 447, 459, 472; 546/134, 306; 552/8; 564/99, 229, 238, 239; 544/164; 549/68, 424, 480

[56] References Cited

U.S. PATENT DOCUMENTS

| | | | |
|---|---|---|---|
| 1,422,506 | 7/1922 | Weiss | 564/238 |
| 1,597,233 | 8/1926 | Heuser et al. | 564/238 |
| 1,642,180 | 9/1927 | Scott | 564/238 |
| 1,672,431 | 6/1928 | Schotte | 564/238 |
| 1,677,235 | 7/1928 | Heuser | 564/238 |
| 1,730,388 | 10/1929 | Brooks | 564/238 |
| 1,756,315 | 4/1930 | terHorst | 564/238 |
| 1,795,398 | 3/1931 | Schotte | 564/238 |
| 1,850,682 | 3/1932 | Meiss | 564/238 |
| 1,915,922 | 6/1933 | Christmann et al. | 564/238 |

(List continued on next page.)

FOREIGN PATENT DOCUMENTS

| | | |
|---|---|---|
| 0001500 | 4/1979 | European Pat. Off. |
| 0035374 | 9/1981 | European Pat. Off. |
| 0179642 | 4/1986 | European Pat. Off. |
| 514248 | 11/1930 | Germany |
| 2029707 | 12/1970 | Germany |
| 2133 056 | 1/1973 | Germany |
| 2452691 | 5/1975 | Germany |
| 3108564 | 11/1982 | Germany |
| 223410 | 10/1924 | United Kingdom |
| 224376 | 11/1924 | United Kingdom |
| 258203 | 9/1926 | United Kingdom |
| 478525 | 1/1938 | United Kingdom |
| 1208252 | 10/1970 | United Kingdom |
| WO 87/04433 | 7/1987 | WIPO |
| WO 88/00583 | 1/1988 | WIPO |
| WO 90/12575 | 11/1990 | WIPO |
| WO 90/14067 | 11/1990 | WIPO |
| 9112797 | 9/1991 | WIPO |
| WO 91/12797 | 9/1991 | WIPO |
| WO 91/18868 | 12/1991 | WIPO |
| WO 92/14697 | 9/1992 | WIPO |
| WO 94/22807 | 10/1994 | WIPO |
| WO 95/20950 | 8/1995 | WIPO |

OTHER PUBLICATIONS

Siqqiqui et al., Pakistan Journal of Scientific ad Industrial Research, 30(3), 163–180 (1987).

Database Crossfire, Beilsteninformationsysteme GmbH, BRN 3095078, 3094377, 3093029, J. Org. Chem. USSR, vol. 4, 1968, p. 459.

Database Crossfire, Beilsteninformationsysteme GmbH, BRN 2938786, Curr. Sci., vol. 45, 1976, p. 764.

(List continued on next page.)

*Primary Examiner*—Peter O'Sullivan
*Attorney, Agent, or Firm*—Peter F. Corless; Edwards & Angell, LLP

[57] ABSTRACT

The present invention provides therapeutically useful substituted guanidines of the following Formula:

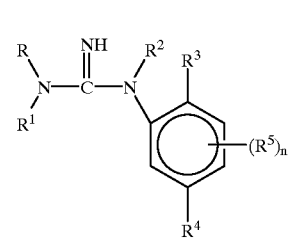

and methods of treatment and pharmaceutical compositions that utilize or comprise one or more of such guanidines.

42 Claims, No Drawings

U.S. PATENT DOCUMENTS

| | | | |
|---|---|---|---|
| 2,145,214 | 1/1939 | Jayne, Jr. | 167/37 |
| 2,254,009 | 8/1941 | Hechenbleikner | 260/564 |
| 2,274,476 | 2/1942 | Hechenbleikner | 167/30 |
| 2,289,541 | 7/1942 | Ericks et al. | 167/22 |
| 2,362,915 | 11/1944 | MacGregor | 3/74 |
| 2,633,474 | 3/1953 | Beaver | 260/565 |
| 2,704,710 | 3/1955 | Sprung | 95/2 |
| 3,117,994 | 1/1964 | McKay et al. | 260/564 |
| 3,140,231 | 7/1964 | Luskin et al. | 167/65 |
| 3,159,676 | 12/1964 | Spickett et al. | 360/564 |
| 3,168,562 | 2/1965 | Walton et al. | 564/237 |
| 3,228,975 | 1/1966 | Abraham et al. | 260/501 |
| 3,248,426 | 4/1966 | Dvornik | 260/564 |
| 3,252,861 | 5/1966 | Mull | 167/65 |
| 3,270,054 | 8/1966 | Gagneux et al. | 260/564 |
| 3,283,003 | 11/1966 | Jack et al. | 260/564 |
| 3,301,755 | 1/1967 | Mull | 167/65 |
| 3,320,229 | 5/1967 | Szabo et al. | 260/96.5 |
| 3,391,189 | 7/1968 | Mull | 260/564 |
| 3,409,669 | 11/1968 | Dyke | 260/564 |
| 3,479,437 | 11/1969 | Szabo et al. | 424/304 |
| 3,547,951 | 12/1970 | Hardie et al. | 260/340.9 |
| 3,639,477 | 2/1972 | L'Italien | 260/564 A |
| 3,681,459 | 8/1972 | Hughes et al. | 424/326 |
| 3,769,427 | 10/1973 | Hughes et al. | 424/326 |
| 3,784,643 | 1/1974 | Suh et al. | 260/564 A |
| 3,803,324 | 4/1974 | Winter et al. | 424/326 |
| 3,804,898 | 4/1974 | Panneman | 260/564 A |
| 3,908,013 | 9/1975 | Hughes et al. | 424/258 |
| 3,949,089 | 4/1976 | Maxwell et al. | 424/326 |
| 3,968,243 | 7/1976 | Maxwell et al. | 424/326 |
| 3,975,533 | 8/1976 | Gauri | 117/54 |
| 3,976,643 | 8/1976 | Diamond et al. | 260/247.5 R |
| 3,976,787 | 8/1976 | Hughes et al. | 424/326 |
| 4,007,181 | 2/1977 | DuCharme et al. | 260/247.5 R |
| 4,014,934 | 3/1977 | Hughes et al. | 260/565 |
| 4,051,256 | 9/1977 | Swallow | 424/304 |
| 4,052,455 | 10/1977 | Matier et al. | 260/563 R |
| 4,060,640 | 11/1977 | Kodama et al. | 424/326 |
| 4,109,014 | 8/1978 | Liu et al. | 424/326 |
| 4,130,663 | 12/1978 | Matier et al. | 424/326 |
| 4,161,541 | 7/1979 | Rasmussen | 424/326 |
| 4,169,154 | 9/1979 | Cohen et al. | 424/322 |
| 4,393,077 | 7/1983 | Douglas et al. | 564/238 |
| 4,471,137 | 9/1984 | Barton et al. | 564/240 |
| 4,709,094 | 11/1987 | Weber et al. | 564/238 |
| 4,742,054 | 5/1988 | Naftchi | 514/215 |
| 4,837,218 | 6/1989 | Olney | 514/646 |
| 4,891,185 | 1/1990 | Goldin | 422/69 |
| 4,898,978 | 2/1990 | Bergfield et al. | 564/238 |
| 4,906,779 | 3/1990 | Weber et al. | 564/238 |
| 5,093,525 | 3/1992 | Weber et al. | 564/238 |
| 5,190,976 | 3/1993 | Weber et al. | 514/634 |
| 5,262,568 | 11/1993 | Weber et al. | 564/238 |
| 5,298,657 | 3/1994 | Durant | 564/238 |
| 5,308,869 | 5/1994 | Keana et al. | 514/637 |
| 5,312,840 | 5/1994 | Keana et al. | 514/634 |
| 5,336,689 | 8/1994 | Weber et al. | 514/634 |
| 5,385,946 | 1/1995 | Keana et al. | 514/634 |
| 5,696,138 | 12/1997 | Olesen et al. | 514/349 |

OTHER PUBLICATIONS

Database Crossfire, Beilsteninformationsysteme GmbH, BRN 3430469, Yuki Gosei Kagaku Kykaisha, vol. 8, 1950, pp. 38, 42.

Doull et al., A Survey of Compounds for Radiation Protection (USAF Radiation Laboratory). (1962).

D. Lloyd et al., *Tetrahedron*, 33:1379–1389 (1977).

H. Shimazu et al., *Chemical Abstracts*, 111(2):16337m (1989).

T. Tada et al., *Chemical Abstracts*, 104(24);208252g (1986).

L. Kiselev et al., *Chemical Abstracts*, 91(21):175291b (1979).

A. Heesing et al., *Chemical Abstracts*, 64(1):15776h (1966).

K. Akiba et al., *Bull. Chem. Soc. Jap.*, 47(4):935–937 (1974).

Database Rtecs, "National Institute of Occupational Safety and Health", RTECS No. MF735000. (Dec. 1990).

J. Keana et al., *Proc. Natl. Acad. Sci.*, 86:5631–5635 (1989).

S. Siddiqui et al., *Pakistan Journal of Scientific and Industrial Res.*, 30(3):163–181 (1987).

E. Maida et al., *Wiener Klinische Wochenschrift*, 90(2):43–48 (1978).

C. Chavkin et al., *Advances in the Biosciences*, 75:407–410 (1989).

P.N. Bhargava et al., *Chemical Abstracts*, 86:598, 189787b (1977).

H.W. Geluk et al., *J. Med. Chem.*, 12:712–715 (1969).

M.W. Scherz et al., *J. Med. Chem.*, 33:2421–2429 (1990).

A.A. Stolyarchuk et al., *Chemical Abstracts*, 86:522–523, 121071h (1977).

T.J.R. Weakley et al., *Acta. Cryst.*, 46:2234–2236 (1990).

J.T. Adams et al., *Eur. J. Pharm.*, 142:61–71 (1987).

B.G. Campbell et al., *J. Neurosci.*, 9:3380–3391 (1989).

G.J. Durant et al., *J. Med. Chem.*, 28:1414–1422 (1985).

M.P. Kavanaugh et al., *Proc. Natl. Acad. Sci. USA*, 85:2844–2848 (1988).

B. Tester et al., *Society for Neuroscience, 19th Annual Meeting*, 983, 396.17 (1989).

E. Weber et al., *Proc. Natl. Acad. Sci. USA*, 83:8784–8788 (1986).

C.A. Maryanoff et al., *J. Org. Chem.*, 51:1822–1884 (1986).

S.R. Safir et al., *J. Org. Chem.*, 13:924–932 (1948).

F.R. Sharp et al., *Society for Neuroscience Abstr.*, 18, Abstr. No. 482.3 (1992).

B. Clemenet et al., *Xenobiotica*, 23(2):155–167 (1993).

Kiselev et al., *Chemical Abstracts*, vol. 66 (1967).

B. Bean, *Ann. N.Y. Acad. Sci.*, 560:334–345 (1989).

B. Bean, *Annu. Rev. Physiol.*, 51:367–384 (1989).

Bent et al., *Pesticides*, 74:63479m (1971).

Chernevskaya et al., *Nature*, 349:418–420 (1991).

D. Choi, *Journal of Neuroscience*, 10(8):2493–2501 (1990).

D. Choi, *Cerebrovascular and Brain Metabolism Reviews*, 2:105–147 (1990).

D. Choi, *Neuron*, 1:623–634 (1988).

Dreyer et al., *Science*, 248:364–367 (1990).

Durant et al., *J. Med. Chem.* 9:22–27 (1966).

Fox et al., *J. Physiol.*, 394:149–172 (1987).

Fox et al., *J. Physiol.*, 394:173–200 (1987).

Ginsburg et al., *Chemical Abstracts*, 4518 (1962).

Ginsburg et al., *Zhurnal Organicheskoi Khimii*, 7(11):2267–2270, Unverified Translation (1971).

Godfraind et al., *Trends in Pharmacological Sciences*, 10(8):297–301 (1989).

S. Goldin et al., *Synthetic Neuroprotective Glutamate Release Blockers*, Small Business Innovation Research Program Phase I Grant Application, funded Dec. 1991.

L. Heinisch, *Journal f. prakt. Chemie*, 329:290–300 (1987).

Huisgen et al., *Chem. Ber.*, 98:1476–1486 (1965).

Huisgen et al., *Chem. Abstracts*, 63:2975 (1965).

Kaneko et al., *Arzneim. Forsch./Drug. Res.*, 39(1):445–450 (1989).

Katragadda et al., *Soc. for Neurosci. Abstr.*, 16:64 (1990).

Kreutzberger et al., *Arch. Pharmz. Ber. Deut. Pharm. Ges.*, 305:400–405 (1972).
Kroeger et al., *Chem. Abstr.*, 60:9264 (1964).
Kroger et al., *Ber.*, 97:396–404 (1964).
Langlais et al., *J. Neuroscience*, 10(5):1664–1674 (1990).
Lemos et al., *Neuron*, 2:1419–1426 (1989).
Leung et al., *Neuron*, 3:767–772 (1989).
Malgouris et al., *J. Neuroscience*, 9(11):3720–3727 (1989).
B. Neldrum, *Cerebrovascular and Brain Metabolism Reviews*, 2:27–57 (1990).
Miura et al., *Chem. Abstr.*, 109:75455d (1988).
Plaitakis et al., *Science*, 216:193–196 (1982).
Plummer et al., *Neuron*, 2:1453–1463 (1989).
Podrebarac et al., *J. Med. Chem.*, 6:283–288 (1963).
Prasad ed al., *Can. J. Chem.*, 45:2247–2252 (1967).
Price et al., *Soc. Neuroscience Abstracts*, 16:377 (1990).
Sah et al., *Soc. Neuroscience Abstr.*, 15:823 (1989).
Sasaki et al., *Synthesis November*, (11):718–719 (1975).
Subbarao et al., *Soc. for Neurosci. Abstr.*, 15:601 (1989).
Sunderdiek et al., *Chemical Abstracts*, 81:91438k (1974).
J.B. Suszkiw, *NATO ASI Series*, H21:285–291 (1988).
Turner et al., *Soc. Neurosci. Abstr.*, 16:1014 (1990).
Turner et al., *Biochemistry*, 28:586–593 (1989).
Turner et al., *Analytical Biochemistry*, 178:8–16 (1989).
Turner et al., *Journal of Neuroscience*, 5(3):841–849 (1985).
Vasilev et al., *Chemical Abstract*, 93:1500095u (1980).
Ahmad et al., *Chemical Abstract*, 108:221382 (1988).

THERAPEUTIC SUBSTITUTED GUANIDINES

This is a continuation of International Application PCT/US94/06008, with an international filing date of May 27, 1994, now abandoned, and which is a continuation-in-part of U.S. application Ser. No. 08/068,522, filed May 27, 1993, now abandoned.

BACKGROUND OF THE INVENTION

1. Field of the Invention

The present invention relates to certain substituted guanidines, and methods of treatment and pharmaceutical compositions that utilize or comprise one or more such guanidines.

2. Background

A number of substituted guanidines have been reported. See, e.g., U.S. Pat. Nos. 1,411,731, 1,422,506, 1,597,233, 1,642,180, 1,672,431, 1,730,388, 1,756,315, 1,795,739, 1,850,682, 2,145,214, 2,254,009, 2,633,474, 3,117,994, 3,140,231, 3,159,676, 3,228,975, 3,248,426, 3,252,816, 3,283,003, 3,270,054, 3,301,755, 3,320,229, 3,301,775, 3,409,669, 3,479,437, 3,547,951, 3,639,477, 3,681,457, 3,769,427, 3,784,643, 3,803,324, 3,908,013, 3,949,089, 3,975,533, 3,976,787, 4,060,640, 4,014,934, 4,161,541, 4,709,094, 4,906,779, 5,093,525, 5,190,976 and 5,262,568; PCT applications WO 90/12575, WO 91/12797, WO 91/18868, and WO 92/14697; and H. W. Geluk, et al., *J. Med. Chem.*, 12:712 (1969).

The amino acid L-glutamate is widely thought to act as a chemical transmitter substance at excitatory synapses within the central nervous system. Neuronal responses to glutamate are complex and appear to be mediated by at least three different receptor types, i.e., KA, QA and NMDA subtypes, each being named for their relatively specific ligands, i.e., kainic acid, quisaqualic acid and N-methyl-D-aspartic acid, respectively. An amino acid which activates one or more of these receptor types is referred to as an excitatory amino acid (EAA).

The NMDA subtype of excitatory amino acid receptors is activated during normal excitatory synaptic transmission in the brain. Activation of NMDA receptors under normal conditions is responsible for the phenomena of long-term potentiation, a memory-like phenomenon, at excitatory synapses. Excessive excitation of neurons occurs in epileptic seizures and it has been shown that over-activation of NMDA receptors contributes to the pathophysiology of epilepsy.

NMDA receptors are also strongly involved in nerve cell death which occurs following brain or spinal cord ischemia. Upon the occurrence of ischemic brain insults such as stroke or heart attack, an excessive release of endogenous glutamate occurs, resulting in the over-stimulation of NMDA receptors. Associated with the NMDA receptors is an ion channel. The recognition site, i.e., the NMDA receptor, is external to the ion channel. When glutamate interacts with the NMDA receptor, it causes the ion channel to open, thereby permitting a flow of cations across the cell membrane, e.g., $Ca^{2+}$ and $Na^+$ into the cell and $K^+$ out of the cell. It is believed that this flux of ions, especially the influx of $Ca^{2+}$ ions, caused by the interaction of glutamate with the NMDA receptor, plays an important role in nerve cell death. See, e.g., S. M. Rothman, et al., *Trends in Neurosci.*, 10(7):299–302 (1987).

Agents which block responses to NMDA receptor activation therefore have therapeutic uses in the treatment of neurological disorders such as epilepsy and also in the prevention of nerve cell death resulting from hypoxia or hypoglycemia or following brain ischemia which occurs during stroke, trauma and heart attack. A number of disorders of the nervous system are associated with neurodegeneration that may be caused by overactivation of NMDA receptors. Antagonists of NMDA receptor-mediated responses have potential therefore for the treatment of such disorders as Alzheimer's disease, Parkinson's disease, Huntington's disease, Amyotrophic Lateral Sclerosis, Down's Syndrome and Korsakoff's disease.

Research on the NMDA receptor-ion channel complex has led to determination of a receptor site within the ion channel known as the PCP receptor. See J. P. Vincent, et al., *Proc. Natl. Acad. Sci. USA*, 76:4678–4682 (1979); S. R. Zukin, et al., *Proc. Natl. Acad. Sci. USA*, 76:5372–5376 (1979); M. S. Sonders, et al., *Trends in Neurosci.*, 11(1):37–40 (1988); and N. A. Anis, et al., *Br. J. Pharmacol.*, 79:565–575 (1983). A compound which binds to the PCP receptor can act as an ion channel blocker, thereby interrupting the flow of ions through the cell membrane. In this manner, agents which interact with the PCP receptor act as non-competitive antagonists reducing the agonist action of glutamate at the NMDA receptor.

Known PCP receptor ligands include PCP, i.e., Phencyclidine, analogues such as 1-[1-(2-thienyl)-cyclohexyl]-piperidine (TCP), benzomorphan (sigma) opiates, and (+)-5-methyl-10,11-dihydro-5H-dibenzo[a,d] cycloheptene-5,10-imine (i.e., the drug MK-801, see U.S. Pat. No. 4,399,141). See, also, E. H. F. Wong, et al., *Proc. Natl. Acad. Sci. USA*, 83:7104–7108 (1986), and W. J. Thompson, et al., *J. Med. Chem.*, 33:789–808 (1990).

SUMMARY OF THE INVENTION

The present invention provides substituted guanidines of Formula I:

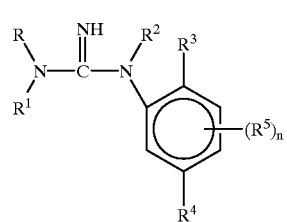

wherein R, $R^1$ and $R^2$ are each independently hydrogen, substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted alkylthio having from 1 to about 20 carbon atoms, substituted or unsubstituted aminoalkyl having from 1 to about 20 carbon atoms, substituted or unsubstituted carbocyclic aryl having at least about 6 ring carbon atoms, substituted or unsubstituted aralkyl having at least about 6 carbon ring atoms, or a substituted or unsubstituted heteroaromatic or heteroalicyclic group having from 1 to 3 rings, 3 to 8 ring members in each ring and from 1 to 3 hetero atoms;

$R^3$ and $R^4$ are each independently halogen, hydroxyl, azido, substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted alkylthio having from 1 to about 20 carbon atoms, substituted or unsubstituted aminoalkyl having from 1 to about 20 carbon atoms, substituted or unsubstituted carbocyclic aryl having at least about 6 ring carbon atoms, or substituted or unsubstituted aralkyl having at least about 6 ring carbon atoms;

each $R^5$ substituent is independently halogen, hydroxyl, azido, substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted alkylthio having from 1 to about 20 carbon atoms, substituted or unsubstituted aminoalkyl having from 1 to about 20 carbon atoms, substituted or unsubstituted carbocyclic aryl having at least about 6 ring carbon atoms, or substituted or unsubstituted aralkyl having at least about 6 ring carbon atoms;

n is an integer of from 0 to 3; and pharmaceutically acceptable salts thereof.

In another aspect, the invention provides compounds of the following Formula II:

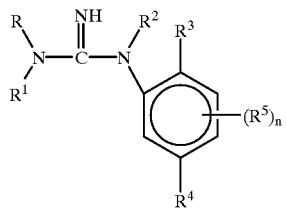

II wherein R, $R^1$ and $R^2$ are each independently hydrogen, substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted alkylthio having from 1 to about 20 carbon atoms, substituted or unsubstituted alkylsulfinyl having from 1 to about 20 carbon atoms, substituted or unsubstituted alkylsulfonyl having from 1 to about 20 carbon atoms, substituted or unsubstituted aminoalkyl having from 1 to about 20 carbon atoms, substituted or unsubstituted carbocyclic aryl having at least 6 ring carbon atoms, substituted or unsubstituted aralkyl having at least 6 ring carbon atoms, or a substituted or unsubstituted heteroaromatic or heteroalicyclic group having 1 to 3 rings, 3 to 8 ring members in each ring and 1 to 3 hetero atoms;

$R^3$, $R^4$, and each $R^5$ substituent are each independently halogen, hydroxyl, azido, substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted alkylthio having from 1 to about 20 carbon atoms, substituted or unsubstituted alkylsulfinyl having from 1 to about 20 carbon atoms, substituted or unsubstituted alkylsulfonyl having from 1 to about 20 carbon atoms, substituted or unsubstituted aminoalkyl having from 1 to about 20 carbon atoms, substituted or unsubstituted carbocyclic aryl having about 6 or more ring carbon atoms, or substituted or unsubstituted aralkyl having about 6 or more ring carbon atoms; n is an integer of from 0–3; or a pharmaceutically acceptable salt thereof. Thus, Formula II is defined the same as above for Formula I except R, $R^1$, $R^2$, $R^3$, $R^4$, $R^5$ of Formula II each also may be independently selected from substituted or unsubstituted alkylsulfoxide having from 1 to about 20 carbon atoms and substituted or unsubstituted alkylsulfonyl having from 1 to about 20 carbon atoms.

Preferred compounds of Formulas I and II exhibit a high affinity for the PCP receptor. The phrase "high affinity for the PCP receptor" as used herein means the compound exhibits an $IC_{50}$ of 1 $\mu$M or less in a typical PCP receptor binding assay such as described in Example 74 which follows, more preferably an $IC_{50}$ of 0.5 $\mu$M or less in such a PCP receptor assay. For reasons discussed below, for at least some therapeutic applications, further preferred are those compounds of Formulas I and II that exhibit such high affinity for the PCP receptor as well as high affinity for the sigma receptor. The phrase "high affinity for the sigma receptor" as used herein means the compound exhibits an $IC_{50}$ of 1 $\mu$M or less in a typical sigma receptor binding assay such as described in Example 75 which follows, more preferably an $IC_{50}$ of 0.5 $\mu$M or less in such a sigma receptor assay.

The substituted guanidines of the invention are useful for a number of therapeutic applications. Accordingly, the present invention includes methods for treatment and/or prophylaxis of neurological conditions such as epilepsy, neurodegenerative conditions and/or nerve cell death resulting from e.g. hypoxia, hypoglycemia, brain or spinal chord ischemia, brain or spinal chord trauma, and the like. Compounds of Formulas I and II also are useful to treat and/or prevent various neurodegenerative diseases such as Parkinson's disease, Huntington's disease, Amyotrophic Lateral Sclerosis, Alzheimer's disease, Down's Syndrome and Korsakoff's disease. The methods of the invention in general comprise administration of a therapeutically effective amount of one or more compounds of Formula I or Formula II to an animal, including a mammal, particularly a human.

The invention also provides pharmaceutical compositions that comprise one or more compounds of Formula I or Formula II and a suitable carrier.

Other aspects of the invention are disclosed infra.

DETAILED DESCRIPTION OF THE INVENTION

Suitable halogen substituent groups of compounds of Formulas I and II as defined above (i.e. compounds of the invention) include F, Cl, Br and I. It is intended that references herein to Formulas I and II, or references to compounds of the invention, apply equally to compounds of Formulas Ia, Ib, Ic, IIa, IIb and IIc as those formulas are defined herein. Hence, suitable and preferred substituent groups of Formulas I and II as identified herein, are also suitable and preferred substituent groups of compounds of Formulas Ia, Ib, Ic, IIa, IIb and IIc. Alkyl groups of compounds of Formulas I and II preferably have from 1 to about 12 carbon atoms, more preferably 1 to about 8 carbon atoms, still more preferably 1 to about 6 carbon atoms, even more preferably 1, 2, 3 or 4 carbon atoms. Methyl, ethyl and propyl including isopropyl are particularly preferred alkyl groups. As used herein, the term alkyl unless otherwise modified refers to both cyclic and noncyclic groups, although of course cyclic groups will comprise at least three carbon ring members. Straight or branched chain noncyclic alkyl groups are generally more preferred than cyclic groups. Preferred alkenyl and alkynyl groups of compounds of the invention have one or more unsaturated linkages and from 2 to about 12 carbon atoms, more preferably 2 to about 8 carbon atoms, still more preferably 2 to about 6 carbon atoms, even more preferably 2, 3 or 4 carbon atoms. The terms alkenyl and alkynyl as used herein refer to both cyclic and noncyclic groups, although straight or branched noncyclic groups are generally more preferred. Preferred alkoxy groups of compounds of Formulas I and II include groups having one or more oxygen linkages and from 1 to about 12 carbon atoms, more preferably from 1 to about 8 carbon atoms, and still more preferably 1 to about 6 carbon atoms, even more preferably 1, 2, 3 or 4 carbon atoms. Preferred alkylthio groups of compounds of Formulas I and II include those groups having one or more thioether linkages and from 1 to about 12 carbon atoms, more preferably from 1 to about 8 carbon atoms, and still more preferably 1 to about 6 carbon atoms. Alkylthio groups having 1, 2, 3 or 4 carbon atoms are particularly preferred. Preferred alkylsulfinyl groups of compounds of the invention include those groups having one or more sulfoxide (SO) groups and from 1 to about 12 carbon atoms, more preferably from 1 to about 8 carbon atoms, and still more preferably 1 to about 6 carbon atoms. Alkylsulfinyl groups having 1, 2, 3 or 4 carbon atoms are particularly preferred. Preferred alkylsulfonyl groups of compounds of the invention include those groups having one or more sulfonyl (SO$_2$) groups and from 1 to about 12 carbon atoms, more preferably from 1 to about 8 carbon atoms, and still more preferably 1 to about 6 carbon atoms. Alkylsulfonyl groups having 1, 2, 3 or 4 carbon atoms are particularly preferred. Preferred aminoalkyl groups include those groups having one or more primary, secondary and/or tertiary amine groups, and from 1 to about 12 carbon atoms, more preferably 1 to about 8 carbon atoms, still more preferably 1 to about 6 carbon atoms, even more preferably 1, 2, 3 or 4 carbon atoms. Secondary and tertiary amine groups are generally more preferred than primary amine moieties. Suitable heteroaromatic groups of compounds of Formula I and Formula II contain one or more N, O or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, imidazolyl, indolyl, benzofuranyl and benzothiazol. Suitable heteroalicyclic groups of compounds of Formula I and Formula II contain one or more N, O or S atoms and include, e.g., tetrahydrofuranyl, tetrahydropyranyl, piperidinyl, morpholino and pyrrolindinyl groups. Suitable carbocyclic aryl groups of compounds of Formula I and Formula II include single and multiple ring compounds, including multiple ring compounds that contain separate and/or fused aryl groups. Typical carbocyclic aryl groups contain 1 to 3 separate or fused rings and from 6 to about 18 carbon ring atoms. Specifically preferred carbocyclic aryl groups include phenyl including 3-substituted phenyl, 2,5-substituted phenyl, 2,3,5-substituted and 2,4,5-substituted phenyl, particularly where the phenyl substituents are independently selected from the same group as defined above for $R^3$—$R^5$; naphthyl including 1-naphthyl and 2-naphthyl; biphenyl; phenanthryl; and anthracyl. Suitable aralkyl groups of compounds of Formula I and Formula II include single and multiple ring compounds, including multiple ring compounds that contain separate and/or fused aryl groups. Typical aralkyl groups contain 1 to 3 separate or fused rings and from 6 to about 18 carbon ring atoms. Preferred aralkyl groups include benzyl and methylenenaphthyl (—CH$_2$-naphthyl).

Said substituted R, $R^1$, $R^2$, $R^3$, $R^4$ and $R^5$ groups of Formula I or Formula II (as well as substituted groups of Formulas Ia–Ic and IIa–IIc as specified below) may be substituted at one or more available positions by one or more suitable groups such as, e.g., halogen such as fluoro, chloro, bromo and iodo; cyano; hydroxyl; nitro; azido; alkanoyl such as a $C_{1-6}$ alkanoyl group such as acyl and the like; carboxamido; alkyl groups including those groups having 1 to about 12 carbon atoms or from 1 to about 6 carbon atoms and more preferably 1–3 carbon atoms; alkenyl and alkynyl groups including groups having one or more unsaturated linkages and from 2 to about 12 carbon or from 2 to about 6 carbon atoms; alkoxy groups having those having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; and aminoalkyl groups such as groups having one or more N atoms and from 1 to about 12 carbon atoms or from 1 to about 6 carbon atoms.

It should be understood that alkoxy, alkylthio, alkylsulfinyl, alkylsulfonyl and aminoalkyl substituent groups described above include groups where a hetero atom is directly bonded to a ring system, such as a carbocyclic aryl group or a heterocyclic group, as well as groups where a hetero atom of the group is spaced from such ring system by an alkylene linkage, e.g. of 1 to about 4 carbon atoms.

Preferred phenyl ring substituents $R^3$, $R^4$ and $R^5$ of Formulas I and II (as well as phenyl ring substituents of Formulas Ia–Ic and IIa–IIc as specified below) include halogen, particularly F, Cl and Br, hydroxyl, azido, substituted or unsubstituted alkyl including halogenated alkyl, substituted and unsubstituted alkoxy including halogenated alkoxy, and substituted and unsubstituted alkylthio. Typically preferred phenyl ring substituents have 1 to 4 carbon atoms with methyl, ethyl, and propyl including isopropyl being particularly preferred. Halogen-substituted alkyl and alkoxy groups are also particularly preferred including fluoroalkyl having 1, 2, 3 or 4 carbon atoms such as trifluoromethyl and fluoro-substituted alkoxy having 1, 2, 3 or 4 carbon atoms such as trifluoromethoxy (—OCF$_3$). Methylthio (—SCH$_3$) and ethylthio (—SCH$_2$CH$_3$) are also particularly preferred phenyl ring substituents.

Preferred compounds of the invention include trisubstituted compounds where one of the guanidine substituents R, $R^1$ and $R^2$ of the above defined Formulas (or the corresponding guanidine substituents of Formulas Ia–Ic and IIa–IIc as specified below) is hydrogen and the other two substituents are other than hydrogen, more preferably where R or $R^1$ is heterocyclic aryl or carbocyclic aryl, still more preferably where R is substituted or unsubstituted heterocyclic aryl or substituted or unsubstituted carbocyclic aryl and one of $R^1$ and $R^2$ is hydrogen and one of $R^1$ and $R^2$ is substituted or unsubstituted alkyl. Also preferred are N,N'-disubstituted compounds, i.e. where one of R and $R^1$ of Formulas I or II (or the corresponding guanidine substituents of Formulas Ia–Ic and IIa–IIc) is hydrogen and $R^2$ is hydrogen, preferably where R is substituted or unsubstituted heterocyclic aryl or substituted or unsubstituted carbocyclic aryl and $R^1$ and $R^2$ are hydrogen. Also preferred are N,N, N',N'-tetrasubstituted compounds, i.e. where each of R, $R^1$ and $R^2$ substituents of Formulas I or II (or the corresponding guanidine substituents of Formulas Ia–Ic and IIa–IIc) is other than hydrogen, preferably where R or $R^1$ is substituted or unsubstituted heterocyclic aryl or substituted or unsubstituted carbocyclic aryl, more preferably where R is substituted or unsubstituted heterocyclic aryl or substituted or unsubstituted carbocyclic aryl and $R^1$ and $R^2$ are each substituted or unsubstituted alkyl. In any event, at least one of the substituents R and $R^1$ of compounds of Formula I or II generally will be other than hydrogen.

Preferred $R^3$, $R^4$ and $R^5$ alkylsulfinyl groups of compounds of Formula II (as well as phenyl ring alkylsulfinyl groups of compounds of Formulas IIa–IIc as specified below) typically have one or more sulfoxide groups, more typically, one or two sulfoxide groups and from 1 to about 8 carbon atoms, more preferably 1 to about 6 carbon atoms, even more preferably 1 to about 3 carbon atoms. Methylsulfinyl (—S(O)CH$_3$) and ethylsulfinyl (—S(O)CH$_2$CH$_3$) are particularly preferred $R^3$, $R^4$ and $R^5$ alkylsulfinyl groups. Preferred substituted alkylsulfinyl groups include haloalkylsulfinyl groups that contain one or more F, Cl, Br or I atoms, preferably one or more F atoms, and preferably 1 to about 3 carbon atoms, more preferably one or two carbon atoms. Specifically preferred groups include fluoromethylsulfinyl, particularly trifluoromethylsulfinyl (—S(O)CF$_3$), and fluoroethylsulfinyl such as 2-trifluoroethylsulfinyl (—S(O)CH$_2$CF$_3$) and pentafluoroethylsulfinyl (—S(O)CF$_2$CF$_3$).

Preferred $R^3$, $R^4$ and $R^5$ alkylsulfonyl ring substituents of compounds of Formula II (as well as phenyl ring alkylsulfonyl groups of compounds of Formulas IIa–IIc as specified below) have one or more sulfono (SO$_2$) groups, more typically one sulfono group, and from 1 to about 8 carbon atoms, still more preferably 1 to about 6 carbon atoms, even more preferably 1 to about 3 carbon atoms. Methylsulfonyl (—S(O)$_2$CH$_3$) and ethylsulfonyl (—S(O)$_2$CH$_2$CH$_3$) are particularly preferred $R^3$ and $R^4$ sulfonoalkyl groups. Preferred substituted alkylsulfonyl groups include haloalkylsulfonyl groups that contain one or more F, Cl, Br or I atoms, preferably one or more F atoms, and preferably 1 to about 3 carbon atoms, more preferably one or two carbon atoms. Specifically preferred groups include fluoromethylsulfonyl, particularly trifluoromethylsulfonyl (—S(O)$_2$CF$_3$), and fluoroethylsulfonyl such as 2-trifluoroethylsulfonyl (—S(O)$_2$CH$_2$CF$_3$) and pentafluoroethylsulfonyl (—S(O)$_2$CF$_2$CF$_3$).

Particularly preferred R and $R^1$ groups include phenyl substituted at least at the 2,5 ring positions. For example, preferred are the following compounds of Formula Ia:

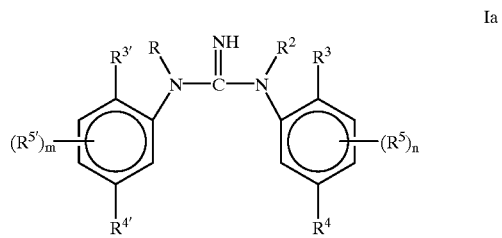

Ia wherein R and $R^2$ are the same as defined above for Formula I; each $R^3$, $R^4$, $R^5$, $R^{3'}$, $R^{4'}$, and $R^{5'}$ substituent is independently selected from the same group of substituents as defined above for $R^3$—$R^5$ for Formula I; m and n are each independently an integer of from 0 to 3; and pharmaceutically acceptable salts thereof. Preferred compounds of Formula Ia include those compounds where at least one of R and $R^2$ is other than heterocyclic aryl or carbocyclic aryl, e.g. where at least one of R and $R^2$ is hydrogen or substituted or unsubstituted alkyl, particularly, substituted or unsubstituted alkyl having 1, 2, 3 or 4 carbon atoms. Preferred values of m and n of Formula Ia are 0 and 1.

Also preferred are compounds of Formula IIa, defined the same as for Formula Ia above, but where each substituent, particularly the $R^3$, $R^4$, $R^5$, $R^{3'}$, $R^{4'}$, and $R^{5'}$ substituents, may be independently alkylsulfinyl having from 1 to about 20 carbon atoms or alkylsulfonyl having from 1 to about 20 carbon atoms. Preferred compounds of Formula IIa include those compounds where at least one of R and $R^2$ is other than heterocyclic aromatic or carbocyclic aryl, e.g. where at least one of R and $R^2$ is hydrogen or substituted or unsubstituted alkyl, particularly, substituted or unsubstituted alkyl having 1, 2, 3 or 4 carbon atoms. Preferred values of m and n of Formula IIa are 0 and 1.

Further preferred compounds of Formula I include those compounds where the value n equals 1, particularly where n equals 1 and the phenyl ring is substituted by a $R^5$ group at the 3- or 4-position, i.e. the phenyl ring is 2,3,5-substituted or 2,4,5-substituted.

Such compounds of Formula II are also preferred, i.e. compounds of Formula II where the value n equals 1, particularly where n equals 1 and the phenyl ring is substituted by a $R^5$ group at the 3- or 4-position, i.e. the phenyl ring is 2,3,5-substituted or 2,4,5-substituted.

Especially preferred compounds of Formula I are those where n is equal to zero (i.e., the 3, 4 and 6 positions of the phenyl ring are hydrogen-substituted), specifically compounds of the following Formula Ib:

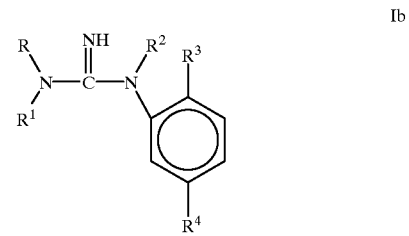

Ib where the groups R through $R^4$ are the same as specified above for Formula I; and pharmaceutically acceptable salts thereof. Particularly preferred compounds of Formula Ib include those compounds where R is substituted or unsubstituted heterocylic aryl or substituted or unsubstituted carbocyclic aryl such as substituted or unsubstituted phenyl or napthyl and where at least one of $R^1$ and $R^2$ is other than heterocyclic aryl or carbocyclic aryl, e.g. where at least one of $R^1$ and $R^2$ is hydrogen or substituted or unsubstituted alkyl, particularly substituted or unsubstituted alkyl having 1, 2, 3 or 4 carbon atoms.

Also preferred are compounds of Formula IIb, defined the same as for Formula Ib above, but where each substituent, particularly the $R^3$ and $R^4$ substituents, may be independently alkylsulfinyl having from 1 to about 20 carbon atoms or alkylsulfonyl having from 1 to about 20 carbon atoms. Particularly preferred compounds of Formula IIb include those compounds where R is substituted or unsubstituted heterocyclic aryl or substituted or unsubstituted carbocyclic aryl such as substituted or unsubstituted phenyl or napthyl and where at least one of $R^1$ and $R^2$ is other than heterocyclic aryl or carbocyclic aryl, e.g. where at least one of $R^1$ and $R^2$ is hydrogen or substituted or unsubstituted alkyl, particularly substituted or unsubstituted alkyl having 1, 2, 3 or 4 carbon atoms.

A still further group of preferred compounds of the invention have, in addition to a 2,5-substituted phenyl moiety, at least one guanidine substituent (i.e., R, $R^1$ or $R_2$ of Formulas I or II) that is a phenyl group substituted at the 3-position, preferably without substitution at other ring positions. Particularly preferred are N-(3-substituted phenyl)-N'-(2,5-disubstituted phenyl)guanidines of the following Formula Ic:

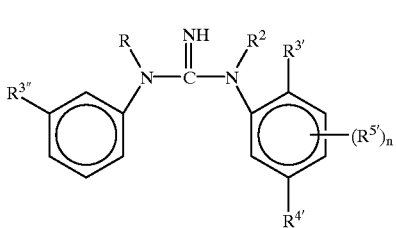

wherein R and R² are the same as defined above for Formula I; each R³', R⁴', R⁵' and R³" substituent is independently selected from the same group of substituents as defined above for R³, R⁴ and R⁵ for Formula I; and n is an integer of from 0 to 3; and pharmaceutically salts of said compounds. Preferred compounds of Formula Ic include those compounds where at least one of R and R² is other than heterocyclic aryl or carbocyclic aryl, e.g. where at least one of R and R² is hydrogen or substituted or unsubstituted alkyl, particularly substituted or unsubstituted alkyl having 1 to about 4 carbon atoms. Especially preferred are compounds of Formula Ic are those where one of R and R² is hydrogen and the other is substituted or unsubstituted alkyl having 1, 2, 3 or 4 carbon atoms, more preferably where R is methyl, ethyl or propyl and R² is hydrogen. Preferred values of n of Formula Ic are 0 and 1.

Also preferred are compounds of Formula IIc, defined the same as for Formula Ic above, but where each substituent, particularly the R³', R⁴', R⁵' and R³" substituents, also may be independently alkylsulfinyl having from 1 to about 20 carbon atoms or alkylsulfonyl having from 1 to about 20 carbon atoms. Preferred compounds of Formula IIc include those compounds where at least one of R and R² is other than heterocyclic aryl or carbocyclic aryl, e.g. where at least one of R and R² is hydrogen or substituted or unsubstituted alkyl, particularly substituted or unsubstituted alkyl having 1, 2, 3 or 4 carbon atoms. Especially preferred are compounds of Formula IIc are those where one of R and R² is hydrogen and the other is substituted or unsubstituted alkyl having 1 to about 4 carbon atoms, more preferably where R is methyl, ethyl or propyl and R² is hydrogen. Preferred values of n of Formula IIc are 0 and 1.

Preferred compounds of Formulas I and II exhibit high affinity to the PCP receptor. For at least some therapeutic applications, use of compounds of Formulas I or II that exhibit high affinity to both the PCP receptor and the sigma receptor may be preferred. While not wishing to be bound by theory, it is thought that an agent that has high affinity to both the PCP and sigma receptors can provide effective therapy for the indications mentioned above without the risk of vacuolar injury as exhibited by some prior NMDA receptor antagonists. See, e.g., Olney et al., *Science*, 244:1360–1364 (1989).

Without wishing to be bound by theory, compounds of the invention that contain an alkylsulfinyl and/or alkylsulfonyl group, may be, in effect, "pro-drugs" wherein after administration of the compound to a subject the sulfinyl or sulfonyl group(s) are metabolized (reduced) in vivo to the corresponding sulfide moiety. In particular, compounds of the invention that have an aryl substituent that is ring-substituted by one or more alkylsulfinyl and/or alkylsulfonyl group(s) may be effective pro-drugs. Thus, preferred compounds of Formula II include those containing a carbocyclic or heterocyclic group, such as a naphthyl or phenyl group, substituted by one or more alkylsulfinyl or alkylsulfonyl groups having from 1 to about 4 carbon atoms.

Specifically preferred compounds of the present invention include:

N-(3-ethylphenyl)-N,N'-dimethyl-N'-(2,5-dichlorophenyl)guanidine;
N-(3-ethylphenyl)-N-methyl-N'-(2,5-dichlorophenyl)guanidine;
N-(3-ethylphenyl)-N'-(2,5-dichlorophenyl)-N'-methylguanidine;
N-(3-ethylphenyl)-N'-(2,5-dichlorophenyl)guanidine;
N-(3-ethylphenyl)-N-methyl-N'-(2,5-dibromophenyl)guanidine;
N-(3-ethylphenyl)-N'-(2,5-dibromophenyl)-N'-methylguanidine;
N-(3-ethylphenyl)-N'-(2,5-dibromophenyl)guanidine;
N-(3-ethylphenyl)-N-methyl-N'-(2-chloro-5-trifluromethylphenyl)guanidine;
N-(3-ethylphenyl)-N'-(2-chloro-5-trifluoromethylphenyl)guanidine;
N-(3-ethylphenyl)-N,N'-dimethyl-N'-(2-bromo-5-trifluoromethylphenyl)guanidine;
N-(3-ethylphenyl)-N-methyl-N'-(2-bromo-5-trifluromethylphenyl)guanidine;
N-(3-ethylphenyl)-N'-(2-bromo-5-trifluoromethylphenyl)guanidine;
N-(3-ethylphenyl)-N-methyl-N'-(2-fluoro-5-trifluromethylphenyl)guanidine;
N-(3-ethylphenyl)-N'-(2-fluoro-5-trifluoromethylphenyl)guanidine;
N-(3-ethylphenyl)-N,N'-dimethyl-N'-(2-chloro-5-ethylphenyl)guanidine;
N-(3-ethylphenyl)-N-methyl-N'-(2-chloro-5-ethylphenyl)guanidine;
N-(3-ethylphenyl)-N'-(2-chloro-5-ethylphenyl)guanidine;
N-(3-ethylphenyl)-N,N'-dimethyl-N'-(2-bromo-5-ethylphenyl)guanidine;
N-(3-ethylphenyl)-N-methyl-N'-(2-bromo-5-ethylphenyl)guanidine;
N-(3-ethylphenyl)-N'-(2-bromo-5-ethylphenyl)guanidine;
N-(3-ethylphenyl)-N,N'-dimethyl-N'-(2-fluoro-5-ethylphenyl)guanidine;
N-(3-ethylphenyl)-N-methyl-N'-(2-fluoro-5-ethylphenyl)guanidine;
N-(3-ethylphenyl)-N'-(2-fluoro-5-ethyiphenyl)guanidine;
N-(3-ethylphenyl)-N,N'-dimethyl-N'-(2-chloro-5-methylphenyl)guanidine;
N-(3-ethylphenyl)-N-methyl-N'-(2-chloro-5-methylphenyl)guanidine;
N-(3-ethylphenyl)-N'-(2-chloro-5-ethylphenyl)guanidine;
N-(3-ethylphenyi)-N'-(2-chloro-5-methylphenyl)guanidine;
N-(3-ethylphenyl)-N-methyl-N'-(2-chloro-5-methylthio)guanidine;
N-(3-ethylphenyl)-N'-(2-chloro-5-methylthio)guanidine;
N-(1-naphthyl)-N'-(2-bromo-5-ethylphenyl)guanidine;

N-(1-naphthyl-N'-(2-fluoro-5-ethylphenyl)guanidine;
N-(1-naphthyl)-N'-(2,5-dichlorophenyl)guanidine;
N-(1-naphthyl)-N'-(2-fluoro-5-methylphenyl)guanidine;
N-(3-ethylphenyl)-N-methyl-N'-(2,4,5-trichlorophenyl)guanidine;
N-(3-ethylphenyl)-N'-(2,4,5-trichlorophenyl)guanidine;
N-(3-ethylphenyl)-N-methyl-N'-(2,3,5-trichlorophenyl)guanidine;
N-(3-ethylphenyl)-N'-(2,3,5-trichlorophenyl)guanidine;
N-(1-naphthyl)-N'-(2,4,5-trichlorophenyl)guanidine;
N-(1-naphthyl)-N'-(2,3,5-trichlorophenyl)guanidine;
N-(1-naphthyl)-N'-(2,5-dichlorophenyl)-N'-methylguanidine;
N-(1-naphthyl)-N'-(2-chloro-5-methylphenyl)guanidine;
N-(1-naphthyl)-N'-(2,5-dimethylphenyl)guanidine;
N-(1-naphthyl)-N'-(2,5-dibromophenyl)guanidine;
N-(1-naphthyl)-N'-(2-chloro-5-methylphenyl)-N'-methylguanidine;
N-(1-naphthyl)-N'-(2-5-dimethylphenyl)-N'-methylguanidine;
N-(1-naphthyl)-N'-(2,5-dibromophenyl)-N-methylguanidine;
N-(1-naphthyl)-N'-(2,5-dibromophenyl)-N'-methylguanidine;
N-(1-naphthyl)-N'-(2-chloro-5-thiomethylphenyl)guanidine;
N-(1-naphthyl)-N'-(2-fluoro-5-trifluoromethylphenyl)guanidine;
N-(1-naphthyl)-N'-(2-chloro-5-trifluoromethylphenyl)guanidine;
N-(1-naphthyl)-N'-(2-bromo-5-trifluoromethylphenyl)guanidine;
N-(1-naphthyl)-N'-(2-thiomethyl-5-trifluoromethylphenyl)guanidine;
N-(1-naphthyl)-N'-(2-methoxy-5-methylphenyl)guanidine;
N-(1-naphthyl)-N'-(2-chloro-5-ethylphenyl)guanidine;
N-(1-naphthyl)-N'-(2-chloro-5-ethylphenyl)-N'-methylguanidine;
N-(1-naphthyl)-N'-methyl-N'-(2-chloro-5-thiomethylphenyl)guanidine;
N-(8-quinolinyl)-N'-(2-chloro-5-methylphenyl)guanidine;
N-(8-quinolinyl)-N'-(2-chloro-5-ethylphenyl)guanidine;
N-(8-quinolinyl)-N'-methyl-(2-chloro-5-ethylphenyl)guanidine;
N-(3-methylthiophenyl)-N-methyl-N'-(2-chloro-5-methylthiophenyl)guanidine;
N-(3-methylthiophenyl)-N'-methyl-N'-(2-chloro-5-methylthiophenyl)guanidine;
N-(3-methylthiophenyl)-N'-(2-chloro-5-methylthiophenyl)guanidine;
N-(3-methylthiophenyl)-N-methyl-N'-(2-chloro-5-ethylphenyl)guanidine;
N-(3-methylthiophenyl)-N'-methyl-N'-(2-chloro-5-ethylphenyl)guanidine;
N-(3-methylthiophenyl)-N'-(2-chloro-5-ethylphenyl)guanidine;
N-(3-methylthiophenyl)-N-methyl-N'-(2-bromo-5-ethylphenyl)guanidine;
N-(3-methylthiophenyl)-N'-methyl-N'-(2-bromo-5-ethylphenyl)guanidine;
N-(3-methylthiophenyl)-N'-(2-bromo-5-ethylphenyl)guanidine;
N-(3-methylthiophenyl-N-methyl-N'-(2,5-dichlorophenyl)guanidine;
N-(3-methylthiophenyl-N'-methyl-N'-(2,5-dichlorophenyl)guanidine;
N-(3-methylthiophenyl-N'-(2,5-dichlorophenyl)guanidine;
N-(3-methylthiophenyl)-N-methyl-N'-(2,5-dibromophenyl)guanidine;
N-(3-methylthiophenyl)-N'-methyl-N'-(2,5-dibromophenyl)guanidine;
N-(3-methylthiophenyl)-N'-(2,5-dibromophenyl)guanidine;
N-(3-trifluoromethylphenyl)-N-methyl-N'-(2-chloro-5-methylthiophenyl)guanidine;
N-(3-trifluoromethylphenyl)-N'-methyl-N'-(2-chloro-5-methylthiophenyl)guanidine;
N-(3-trifluoromethylphenyl)-N'-(2-chloro-5-methylthiophenyl)guanidine;
N-(3-trifluoromethylphenyl)-N-methyl-N'-(2-chloro-5-ethylphenyl)guanidine;
N-(3-trifluoromethylphenyl)-N'-methyl-N'-(2-chloro-5-ethylphenyl)guanidine;
N-(3-trifluoromethylphenyl)-N'-(2-chloro-5-ethylphenyl)guanidine;
N-(3-trifluoromethylphenyl)-N-methyl-N'-(2-bromo-5-ethylphenyl)guanidine;
N-(3-trifluoromethylphenyl)-N'-methyl-N'-(2-bromo-5-ethylphenyl)guanidine;
N-(3-trifluoromethylphenyl)-N'-(2-bromo-5-ethylphenyl)guanidine;
N-(3-trifluoromethylphenyl)-N-methyl-N'-(2,5-dichlorophenyl)guanidine;
N-(3-trifluoromethylphenyl)-N'-methyl-N'-(2,5-dichlorophenyl)guanidine;
N-(3-trifluoromethylphenyl)-N'-(2,5-dichlorophenyl)guanidine;
N-(3-trifluoromethylphenyl)-N-methyl-N'-(2,5-dibromophenyl)guanidine;
N-(3-trifluoromethylphenyl)-N'-methyl-N'-(2,5-dibromophenyl)guanidine;
N-(3-trifluoromethylphenyl)-N'-(2,5-dibromophenyl)guanidine;
N-(3-ethylphenyl)-N-methyl-N'-(2-bromo-5-methylthiophenyl)guanidine;
N-(3-ethylphenyl)-N'-methyl-N'-(2-bromo-5-methylthiophenyl)guanidine;
N-(3-ethylphenyl)-N'-(2-bromo-5-methylthiophenyl)guanidine;
N-(3-methylthiophenyl)-N-methyl-N'-(2-bromo-5-methylthiophenyl)guanidine;
N-(3-methylthiophenyl)-N'-methyl-N'-(2-bromo-5-methylthiophenyl)guanidine;
N-(3-methylthiophenyl)-N'-(2-bromo-5-methylthiophenyl)guanidine;
N-(3-methylthiophenyl)-N-methyl-N'-(2-bromo-5-ethylphenyl)guanidine;
N-(3-methylthiophenyl)-N'-methyl-N'-(2-bromo-5-ethylphenyl)guanidine;

N-(3-methylthiophenyl)-N'-(2-bromo-5-ethylphenyl) guanidine;
N-(3-trifluoromethylphenyl)-N-methyl-N'-(2-bromo-5-methylthiophenyl)guanidine;
N-(3-trifluoromethylphenyl)-N'-methyl-N'-(2-bromo-5-methylthiophenyl)guanidine;
N-(3-trifluoromethylphenyl)-N'-(2-bromo-5-methylthiophenyl)guanidine;
N-(3-bromophenyl)-N-methyl-N'-(2-chloro-5-methylthiophenyl)guanidine;
N-(3-bromophenyl)-N'-methyl-N'-(2-chloro-5-methylthiophenyl)guanidine;
N-(3-bromophenyl)-N'-(2-chloro-5-methylthiophenyl) guanidine;
N-(3-trifluoromethoxyphenyl)-N-methyl-N'-(2,5-dibromophenyl)guanidine;
N-(3-trifluoromethoxyphenyl)-N'-methyl-N'-(2,5-dibromophenyl)guanidine;
N-(3-trifluoromethoxyphenyl)-N'-(2,5-dibromophenyl) guanidine;
N-(3-trifluoromethoxyphenyl)-N-methyl-N'-(2-bromo-5-ethylphenyl)guanidine;
N-(3-trifluoromethoxyphenyl)-N'-methyl-N'-(2-bromo-5-5 ethylphenyl)guanidine;
N-(3-trifluoromethoxyphenyl)-N'-(2-bromo-5-ethylphenyl)guanidine;
N-(3-methylsulfonylphenyl)-N-methyl-N'-(2,5-dibromophenyl)guanidine;
N-(3-methylsulfonylphenyl)-N'-methyl-N'-(2,5-dibromophenyl)guanidine;
N-(3-methylsulfonylphenyl)-N'-(2,5-dibromophenyl) guanidine;
N-(3-methylsulfinylphenyl)-N-methyl-N'-(2,5-dibromophenyl)guanidine;
N-(3-methylsulfinylphenyl)-N'-methyl-N'-(2,5-dibromophenyl)guanidine;
N-(3-methylsulfinylphenyl)-N'-(2,5-dibromophenyl) guanidine;
N-(3-iodophenyl)-N-methyl-N'-(2-chloro-5-methylthiophenyl)guanidine;
N-(3-iodophenyl)-N'-methyl-N'-(2-chloro-5-methylthiophenyl)guanidine;
N-(3-iodophenyl)-N'-(2-chloro-5-methylthiophenyl) guanidine;
N-(3-iodophenyl)-N-methyl-N'-(2-chloro-5-ethylphenyl) guanidine;
N-(3-iodophenyl)-N'-methyl-N'-(2-chloro-5-ethylphenyl) guanidine;
N-(3-iodophenyl)-N'-(2-chloro-5-ethylphenyl)guanidine;
N-(3-ethylphenyl)-N'-(2-chloro-5-ethylthiophenyl) guanidine;
N-(3-ethylphenyl)-N-methyl-N'-(2-chloro-5-ethylthiophenyl)guanidine;
N-(3-ethylphenyl)-N'-methyl-N'-(2-chloro-5-ethylthiophenyl)guanidine;
N-(3-ethylphenyl)-N,N'-dimethyl-N'-(2-chloro-5-ethylthiophenyl)guanidine;
N-(3-ethylphenyl)-N'-(2-bromo-5-ethylthiophenyl) guanidine;
N-(3-ethylphenyl)-N-methyl-N'-(2-bromo-5-ethylthiophenyl)guanidine;
N-(3-ethylphenyl)-N'-methyl-N'-(2-bromo-5-ethylthiophenyl)guanidine;
N-(3-ethylphenyl)-N,N'-dimethyl-N'-(2-bromo-5-ethylthiophenyl)guanidine;
N-(3-methylthiophenyl)-N'-(2-chloro-5-ethylthiophenyl) guanidine;
N-(3-methylthiophenyl)-N-methyl-N'-(2-chloro-5-ethylthiophenyl)guanidine;
N-(3-methylthiophenyl)-N'-methyl-N'-(2-chloro-5-ethylthiophenyl)guanidine;
N-(3-methylthiophenyl)-N,N'-dimethyl-N'-(2-chloro-5-ethylthiophenyl)guanidine;
N-(3-methylthiophenyl)-N'-(2-bromo-5-ethylthiophenyl) guanidine;
N-(3-methylthiophenyl)-N-methyl-N'-(2-bromo-5-ethylthiophenyl)guanidine;
N-(3-methylthiophenyl)-N'-methyl-N'-(2-bromo-5-ethylthiophenyl)guanidine;
N-(3-methylthiophenyl)-N,N'-dimethyl-N'-(2-bromo-5-ethylthiophenyl)guanidine;
N-(3-trifluoromethylphenyl)-N'-(2-chloro-5-ethylthiophenyl) guanidine;
N-(3-trifluoromethylphenyl)-N-methyl-N'-(2-chloro-5-ethylthiophenyl)guanidine;
N-(3-trifluoromethylphenyl)-N'-methyl-N'-(2-chloro-5-ethylthiophenyl)guanidine;
N-(3-trifluoromethylphenyl)-N,N'-dimethyl-N'-(2-chloro-5-ethylthiophenyl)guanidine;
N-(3-trifluoromethylphenyl)-N'-(2-bromo-5-ethylthiophenyl)guanidine;
N-(3-trifluoromethylphenyl)-N-methyl-N'-(2-bromo-5-ethylthiophenyl)guanidine;
N-(3-trifluoromethylphenyl)-N'-methyl-N'-(2-bromo-5-ethylthiophenyl)guanidine;
N-(3-trifluoromethylphenyl)-N,N'-dimethyl-N'-(2-bromo-5-ethylthiophenyl)guanidine;
N-(3-ethylphenyl)-N'-(2-chloro-5-trifluoromethylthiophenyl)guanidine;
N-(3-ethylphenyl)-N-methyl-N'-(2-chloro-5-trifluoromethylthiophenyl)guanidine;
N-(3-ethylphenyl)-N'-methyl-N'-(2-chloro-5-trifluoromethylthiophenyl)guanidine;
N-(3-ethylphenyl)-N,N'-dimethyl-N'-(2-chloro-5-trifluoromethylthiophenyl)guanidine;
N-(3-ethylphenyl)-N'-(2-bromo-5-trifluoromethylthiophenyl)guanidine;
N-(3-ethylphenyl)-N-methyl-N'-(2-bromo-5-trifluoromethylthiophenyl)guanidine;
N-(3-ethylphenyl)-N'-methyl-N'-(2-bromo-5-trifluoromethylthiophenyl)guanidine;
N-(3-ethylphenyl)-N,N'-dimethyl-N'-(2-bromo-5-trifluoromethylthiophenyl)guanidine;
N-(3-methylthiophenyl)-N'-(2-chloro-5-trifluoromethylthiophenyl)guanidine;
N-(3-methylthiophenyl)-N-methyl-N'-(2-chloro-5-trifluoromethylthiophenyl)guanidine;
N-(3-methylthiophenyl)-N'-methyl-N'-(2-chloro-5-trifluoromethylthiophenyl)guanidine;
N-(3-methylthiophenyl)-N,N'-dimethyl-N'-(2-chloro-5-trifluoromethylthiophenyl)guanidine;
N-(3-methylthiophenyl)-N'-(2-bromo-5-trifluoromethylthiophenyl)guanidine;

N-(3-methylthiophenyl)-N-methyl-N'-(2-bromo-5-trifluoromethylthiophenyl)guanidine;

N-(3-methylthiophenyl)-N'-methyl-N'-(2-bromo-5-trifluoromethylthiophenyl)guanidine;

N-(3-methylthiophenyl)-N,N'-dimethyl-N'-(2-bromo-5-trifluoromethylthiophenyl)guanidine;

N-(3-trifluoromethylphenyl)-N'-(2-chloro-5-trifluoromethylthiophenyl)guanidine;

N-(3-trifluoromethylphenyl)-N-methyl-N'-(2-chloro-5-trifluoromethylthiophenyl)guanidine;

N-(3-trifluoromethylphenyl)-N'-methyl-N'-(2-chloro-5-trifluoromethylthiophenyl)guanidine;

N-(3-trifluoromethylphenyl)-N,N'-dimethyl-N'-(2-chloro-5-trifluoromethylthiophenyl)guanidine;

N-(3-trifluoromethylphenyl)-N'-(2-bromo-5-trifluoromethylthiophenyl)guanidine;

N-(3-trifluoromethylphenyl)-N-methyl-N'-(2-bromo-5-trifluoromethylthiophenyl)guanidine;

N-(3-trifluoromethylphenyl)-N'-methyl-N'-(2-bromo-5-trifluoromethylthiophenyl)guanidine;

N-(3-trifluoromethylphenyl)-N,N'-dimethyl-N'-(2-bromo-5-trifluoromethylthiophenyl)guanidine;

N-(1-naphthyl)-N'-(2-chloro-5-methylthiophenyl)guanidine;

N-(1-naphthyl)-N'-(2-iodo-5-methylthiophenyl)guanidine;

N-(1-naphthyl)-N'-(2-bromo-5-methylthiophenyl)guanidine; and pharmaceutically acceptable salts of said compounds.

Also specifically preferred are compounds specifically identified 25 above and having one or more additional guanidine substituents (i.e., R, $R^1$ or $R^2$ substituents of Formulas I or II) that are other than hydrogen, particularly one or more additional substituents that are substituted or unsubstituted alkyl, especially unsubstituted methyl, ethyl, propyl, butyl, pentyl or hexyl, more preferably unsubstituted methyl, ethyl or propyl. For example, tetra-substituted compounds are particularly preferred such as di-alkyl-, di-aryl-substituted compounds such as N-(3-ethylphenyl)-N,N'-dimethyl-N'-(2,5-dibromophenyl)guanidine, N-(3-ethylphenyl)-N,N'-dimethyl-N'-(2-chloro-5-trifluromethylphenyl)guanidine, and the like.

In a further aspect, the invention provides compounds of Formula II', which Formula II' is defined the same as Formula II above but where each of the substituents $R^3$, $R^4$ and each $R^5$ also may be independently nitro, cyano, substituted or unsubstituted alkanoyl or substituted or unsubstituted carboxyl. Suitable and preferred substituents of compounds of Formula II as disclosed herein are also suitable and preferred substituents of Formula II'. Suitable alkanoyl groups of Formula II' have 1 to about 8 carbon atoms, more preferably 1 to about 4 carbon atoms. Acyl is a particularly suitable alkanoyl group. Carboxyl groups of Formula II' include acid and ester groups of the formula $-(CH_2)_n COOY$ where n is an integer equal to 0 to about 8, more preferably 1, 2, 3 or 4, and Y is hydrogen or substituted or unsubstituted alkyl, preferably have 1 to about 6 carbon atoms, or 1 to about 3 carbon atoms. Compounds of Formula II' can be prepared as disclosed herein for synthesis of compounds of Formulas I and II. The invention also includes use of compounds of Formula II' for the methods of treatment disclosed herein, in the same manner as described for Formulas I and II.

Compounds of Formulas I and II can be readily prepared by the reaction of an amine, typically an amine salt such as an amine hydrochloride, with a preformed alkyl or aryl cyanamide (see S. R. Safer, et al., *J. Org. Chem.*, 13:924 (1948)) or the corresponding N-substituted alkyl or aryl cyanamide. This is a particularly suitable method for producing N,N'-diaryl-N'-alkyl guanidines in which the substituents are not identical. For a synthesis of asymmetrical guanidines, see G. J. Durant, et al., *J. Med. Chem.*, 28:1414 (1985), and C. A. Maryanoff, et al., *J. Org. Chem.*, 51:1882 (1986), incorporated by reference herein. For additional discussion of guanidine synthesis, see PCT application WO 91/12797 and U.S. Pat. Nos. 5,093,525, 5,262,568 and 5,265,568, all incorporated by reference herein. See also H. W. J. Cressman, *Org. Syn. Coll.*, 3:608–609 (1955); M. P. Kavanaugh, et al., *Proc. Natl. Acad. Sci. USA*, 85:2844–2848 (1988); and E. Weber, et al., *Proc. Natl. Acad. Sci. USA*, 83:8784–8788 (1 986), all incorporated herein by reference.

More particularly, compounds of Formulas I and II can be prepared suitably by reaction of an appropriate amine salt such an amine hydrochloride with a slight molar excess (e.g., ca. 1.1 molar equivalent) of a substituted cyanamide in a suitable solvent such as toluene or chlorobenzene under an inert atmosphere such as argon or nitrogen. The reaction solution is then heated from about 110° to 120° C. for 2 to about 16 hours until reaction completion, e.g. as indicated by thin layer chromatography. The reaction solution is then cooled to room temperature, and then preferably diluted with a solvent such as absolute alcohol. The solvent is then removed under reduced pressure to provide the desired substituted guanidine. The crude product then can be purified by recrystallization and/or flash chromatography, e.g. by elution on silica gel (60–200 mesh, 50× w/w) with 5–25% methanol in ethyl acetate. Suitable recrystallization solvents include an ethanol/ethyl acetate mixture or an ethanol/ether mixture. The cyanamide and amine reagents with appropriate substituents (i.e., R, $R^1$, $R^2$ and $R^3$,$R^4$,$R^5$-substituted phenyl substituents), are commercially available or can be readily prepared by known procedures. For example, the cyanamide starting material can be synthesized from the correspondingly substituted amine by treatment with cyanogen bromide (BrCN) in suitable solvent such as dry ethyl ether. The amine hydrochloride can be obtained by treatment of an appropriate amine with an excess of HCl. For example, a 2,5-substituted aniline hydrochloride salt can be prepared by adding methanolic HCl to a cooled solution of the substituted aniline and then stirring at room temperature for about 30 minutes. An alkylsulfinyl-substituted or alkylsulfonyl-substituted reagent, that can provide correspondingly substituted compounds of the invention as described above, can be provided by oxidation (e.g., $H_2O_2$) of alkylthio-substituted reagents. See, for instance, Example 5 which follows.

As discussed above, the present invention includes methods for treating or preventing certain neurological disorders, including the consequences of stroke or traumatic brain injury, epilepsy or neurodegenerative diseases comprising the administration of an effective amount of one or more guanidines of Formulas I or II to a subject including a mammal, particularly a human, in need of such treatment. In particular, the invention provides methods for treatment and/or prophylaxis of nerve cell death resulting e.g. from hypoxia, hypoglycemia, brain or spinal cord ischemia, brain or spinal cord trauma, stroke, heart attack or drowning. Typical candidates for treatment include e.g. heart attack, stroke, brain or spinal cord injury patients, patients undergoing major surgery such as heart surgery where brain ischemia is a potential complication and patients such as divers suffering from decompression sickness due to gas emboli in the blood stream.

In particular, the invention provides methods for treatment which comprise administration of one or more compounds of the invention to a patient that is undergoing surgery or other procedure where brain or spinal cord ischemia is a potential risk. For example, carotid endarterectomy is a surgical procedure employed to correct atherosclerosis of the carotid arteries. Major risks associated with the procedure include intraoperative embolization and the danger of hypertension in the brain following increased cerebral blood flow, which may result in aneurism or hemorrhage. Thus, an effective amount of one or more compounds of the present invention could be administered pre-operatively or peri-operatively to reduce such risks associated with carotid endarterectomy.

The present invention further includes methods for prophylaxis against neurological deficits resulting from coronary artery bypass grafts and aortic valve replacement surgery. Those methods will comprise administering to a patient undergoing such surgical procedures an effective amount of one or more compounds of the invention, typically either pre-operatively or peri-operatively.

The present invention also provides methods for prophylaxis against neurological injury for patients undergoing myocardial infarction, a procedure that can result in ischemic insult to the patient. Such methods will comprise administering to a patient undergoing such surgical procedure an effective amount of one or more compounds of the invention, typically either pre-operatively or peri-operatively.

Also provided are methods for treating or preventing neuropathic pain such as may experienced by cancer patients, persons having diabetes, amputees and other persons who may experience neuropathic pain. These methods for treatment comprise administration of an effective amount of one or more compounds of Formulas I or II to a patient in need of such treatment.

Further provided are methods of ameliorating the neurotoxic effect induced by glutamate interacting with the NMDA receptor of a nerve cell, comprising administering to a subject, such as a mammal, particularly a human, exhibiting symptoms of or susceptible to such neurotoxic effect, one or more compounds of Formulas I or II in an amount effective to ameliorate the neurotoxic effect.

This invention also provides methods of inhibiting NMDA receptor-ion channel related neurotoxicity comprising administering to a subject in need thereof such as a mammal, particularly a human, one or more compounds of Formulas I or II in an amount effective to inhibit or prevent the neurotoxicity.

The invention further provides a method of treating Korsakoff's disease, a chronic alcoholism-induced condition, comprising administering to a subject including a mammal, particularly a human, one or more compounds of Formula I or Formula II in an amount effective to treat the disease. Pretreatment of animals with the NMDA antagonist MK-801 (Merck Index, monograph 3392, 11th ed., 1989) markedly attenuates the extent of cell loss, hemorrhages and amino acid changes in a rat model of Korsakoff's disease. See P. J. Langlais, et al., Soc. Neurosci. Abstr., 14:774 (1988). Therefore, compounds of the present invention have utility for the attenuation of cell loss, hemorrhages and amino acid changes associated with Korsakoff's disease.

The invention also provides methods for determining binding activity of compounds of the invention, e.g. binding activity to NMDA receptors, as well as in vitro and in vivo binding activity diagnostic methods using one or more radiolabelled compounds of Formula I or Formula II, e.g., a compound of the invention that is labeled with $^{125}$I, tritium, $^{32}$P, $^{99}$Tc, or the like, preferably $^{125}$I. For instance, a compound of the invention having a phenyl substituent that is ring substituted with one or more $^{125}$I groups can be administered to a mammal and the subject then scanned for binding of the compound to NMDA receptors. Specifically, single photon emission computed tomography ("SPECT") can be employed to detect such binding. Such an analysis of the mammal could e.g. aid in the diagnosis and treatment of acute cerebral ischemia.

Accordingly, the invention includes compounds of Formula I or II that contain a radiolabel such as $^{125}$I, tritium, $^{32}$P, $^{99}$Tc, or the like, preferably $^{125}$I. Such radiolabelled compounds can be suitably prepared by procedures known in the synthesis art. For example, a compound of the invention having an aromatic group, such as phenyl, that has a bromo or chloro ring substituent can be employed in an exchange labeling reaction to provide the corresponding compound having an $^{125}$I ring substituent.

Certain pharmacological activity of compounds of Formulas I and II can be determined by, e.g., a method involving: (a) determining the binding affinity with respect to the PCP receptor by competitive displacement of tritiated MK-801; (b) in vitro cytotoxicity studies measuring the ability of the compound to prevent nerve cell death caused by exposure to glutamate; and (c) determination of in vivo neuroprotective ability using animal models.

Evaluation of the binding activity of compounds of Formulas I and II with respect to the PCP receptor is suitably performed using radioligand binding assays. The compounds are tested to determine their ability to displace tritiated MK-801 which is used to label PCP receptors. Evaluating the competitive displacement binding data, the preferred compounds are those which exhibit a high affinity (i.e., low $IC_{50}$ value) for the PCP receptors. Under such PCP binding activity studies, an $IC_{50}$ value of at most about 1 $\mu$M, preferably at most about 0.5 $\mu$M, indicates a high binding affinity.

As discussed above, under sigma binding studies an $IC_{50}$ value of less than 1 $\mu$M indicates a high binding affinity of a compound to the sigma receptor. The sigma receptor binding assay, preferably against $^3$H-DTG, may be performed as disclosed by E. Weber, et al., Proc. Natl. Acad. Sci (USA), 83:8784–8788 (1986), which is incorporated by reference herein.

Compounds of Formulas I and II may be used in therapy in conjunction with other medicaments. For example, for treatment of a stroke victim, one or more compounds of Formulas I or II may be suitably administered together with a pharmaceutical targeted for interaction in the blood clotting mechanism such as streptokinase, tPA, urokinase and other agents that lyse clots.

As discussed above, preferred guanidines of Formulas I and II exhibit high affinity for the PCP receptor. Thus, in addition to the treatment of neurodegeneration and related conditions discussed above, the guanidines of the present invention may also be used as a pharmacological tool in an animal model for the screening of potential PCP receptor ligands.

The compounds of this invention can be administered intranasally, orally or by injection, e.g., intramuscular, intraperitoneal, subcutaneous or intravenous injection, or by transdermal, intraocular or enteral means. The optimal dose can be determined by conventional means. Guanidines of the present invention are suitably administered to a subject in the protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, etc.

The compounds of this invention can be employed, either alone or in combination with one or more other therapeutic agents as discussed above, as a pharmaceutical composition in mixture with conventional excipient, i.e., pharmaceutically acceptable organic or inorganic carrier substances suitable for parenteral, enteral or intranasal application which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

For parenteral application, particularly suitable are solutions, preferably oily or aqueous solutions as well as suspensions, emulsions, or implants, including suppositories. Ampules are convenient unit dosages.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

Intravenous or parenteral administration, e.g., subcutaneous, intraperitoneal or intramuscular administration are preferred. The compounds of this invention are particularly valuable in the treatment of mammalian subjects, e.g., humans, wherein the pathophysiology of the disease involves excessive excitation of nerve cells by agonists of the NMDA receptor. Typically, such subjects include those afflicted with neurodegenerative diseases such as Parkinson's disease, Huntington's disease, Amyotrophic Lateral Sclerosis, Alzheimer's disease, Down's Syndrome and Korsakoff's disease. Also suitable for treatment are those subjects suffering from or likely to suffer from nervous system dysfunctions resulting from, for example, epilepsy or nerve cell degeneration which is the result of hypoxia, hypoglycemia, brain or spinal chord ischemia or brain or spinal chord trauma. As discussed above, typical candidates for treatment include heart attack, stroke, brain or spinal cord injury patients, patients undergoing major surgery where brain or spinal cord ischemia is a potential complication and patients such as divers suffering from decompression sickness due to gas emboli in the blood stream.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines. In general, a suitable effective dose of one or more compounds of Formula I or Formula II, particularly when using the more potent compound(s) of Formulas I or II, will be in the range of from 0.01 to 100 milligrams per kilogram of bodyweight of recipient per day, preferably in the range of from 0.01 to 20 milligrams per kilogram bodyweight of recipient per day, more preferably in the range of 0.05 to 4 milligrams per kilogram bodyweight of recipient per day. The desired dose is suitably administered once daily, or several sub-doses, e.g. 2 to 4 sub-doses, are administered at appropriate intervals through the day, or other appropriate schedule. Such sub-doses may be administered as unit dosage forms, e.g., containing from 0.05 to 10 milligrams of compound(s) of Formula I or II per unit dosage, preferably from 0.2 to 2 milligrams per unit dosage.

As with prior guanidines such as those reported in U.S. Pat. No. 1,411,713, the guanidines of the present invention should have utility as rubber accelerators.

The entire text of all applications, patents and publications cited above and below are incorporated by reference herein.

The following non-limiting examples are illustrative of the invention.

GENERAL COMMENTS

In the following examples, melting points (mp) were determined in open capillary tubes on a Thomas-Hoover apparatus (compounds melting <230° C.) and are uncorrected. The NMR spectra of all compounds were recorded on a General Electric QE-300 or Bruker 300, and chemical shifts are reported in ppm relative to the residual signal of the deuterated solvent ($CHCl_3$, 7.26 ppm; $HCD_2OD$, 3.30 ppm; TMS, 0.00 ppm). IR spectra were recorded on a Nicolet 5DXB FT-IR, or a Perkin-Elmer model 1420 in $CHCl_3$ or neat. IR and NMR spectra of all compounds are consistent with their assigned structures. Elemental analyses were performed by M-H-W Laboratories (Phoenix, Ariz.), or Galbraith Laboratories (Knoxville, Tenn.). 1-Naphthylamine, cyanogen bromide, 3-ethylaniline and chlorobenzene were obtained from Aldrich Chemical Company, and were used as received. All other solvents were reagent grade. 1-Naphthyl cyanamide that can be used to prepare compounds of Examples 27–46 and 51 is suitably prepared by the following procedure. To a solution of 20.0 g (140 mMol) 1-naphthylamine in ether at 0° C. was added by cannulation a solution of 17.5 mL (87.5 mMol) BrCN (5.0 M in $CH_3CN$; Aldrich). After 0.5 hours the cooling bath was removed and the mixture was stirred at room temperature overnight (14 hours). A crystalline precipitate of the amine•HBr was formed, which was filtered off under suction, and washed with ethyl acetate (15 mL×3). The filtrate was concentrated in vacuo to provide 12.5 g of a purple colored solid of the crude cyanamide, whose TLC showed the presence of minor amounts of the hydrobromide amine salt. The crude solid was stirred with water (200 mL) for 1 hour, after which filtration under suction left a pinkish solid which was dried in a vacuum oven overnight to afford 9.2 g, (78.3%) of the pure 1-naphthyl cyanamide.

EXAMPLE 1

Preparation of N-(3-ethylphenyl)-N-methyl-N'-2,5-dichlorophenyl)guanidine hydrochloride (Formula I: hydrochloride salt of R=3-ethylphenyl, $R^1=CH_3$, $R^2=H$, $R^3=R^4=Cl$, n=0).

Part 1: Preparation of N-(3-ethylphenyl)-N-methylcyanamide

Step A: 3-ethylphenylcyanamide

A solution of cyanogen bromide (11.36 g, 107 mmol) in anhydrous diethylether (50 mL) was added slowly to a stirred solution of 3-ethylaniline (20.8 g, 171 mmol) in diethylether at 4° C. After the addition, the reaction mixture was stirred at 24° C. for 12 hours and it became a brown solution with a white precipitate. The precipitate was filtered off; the filtrate was washed with aqueous HCl (1N, 3×150 mL) and brine (60 mL). Then the etherate solution was dried over $MgSO_4$, filtered, and concentrated to yield a thick liquid. The crude product was further purified by chromatography ($SiO_2$, hexanes, hexanes/$CH_2Cl_2$, $CH_2Cl_2$) to afford 3-ethylphenylcyanamide (11.6 g, 76% in yield) as a liquid.

Step B: N-(3-ethylphenyl)-N-methylcyanamide

A suspension of 3-ethylphenylcyanamide (4.65 g, 31.8 mmol) and sodium hydride (2.55 g of 80% NaH in mineral oil suspension, 63.6 mmol of NaH) in dried THF was heated at reflux for 3 hours. The reaction mixture was cooled in an ice bath and methyl iodide (11.28 g, 79.5 mmol) was added dropwise with stirring to the mixture. The reaction mixture was then allowed to stir for 15 hours, followed by the successive addition of MeOH (10 mL). The reaction mixture was then concentrated to dryness to give the crude product. Distilled water (40 mL) was added to this crude product and the aqueous mixture was extracted with $CH_2Cl_2$ (4×40 mL). The combined organic extracts were washed with water (3×30 mL) and then dried over $MgSO_4$. The solvent was removed to afford the crude product as an amber syrup. Flash chromatography ($SiO_2$, $CH_2Cl_2$) of the crude product afforded 4.2 g (75% yield) of the desired product.

Part 2: Preparation of 2,5-Dichloroaniline Hydrochloride

To a solution of 2,5-dichloroaniline (Aldrich, 1.5 g, 9 mmol) in methanol (10 mL) was added methanolic HCl (1M, 30 mL) at 4° C., then the reaction mixture was stirred at 25° C. for 30 minutes. The resulting solution was then evaporated and dried under vacuum to afford 1.6 g of 2,5-dichloroaniline hydrochloride (88% yield).

Part 3: Guanidine Synthesis

A mixture of N-(3-ethylphenyl)-N-methylcyanamide (520 mg, 3.3 mmol), 2,5-dichloroaniline hydrochloride (600 mg, 3 mmol), and chlorobenzene (2 mL) were combined in a dry round bottom flask equipped with a water cooled condenser under nitrogen and placed in a preheated oil bath (150–160° C.). The reaction mixture was heated for 4 hours. After cooling, the crude reaction product was purified by crystallization from chlorobenzene/diethylether. The resulting crystals were collected by filtration, washed with diethylether, and dried in a vacuum oven (40° C., 15 hours) to yield the title compound, N-(3-ethylphenyl)-N-methyl-N'-(2,5-dichlorophenyl)guanidine hydrochloride, as a white solid (760 mg, 72% yield).

TLC: $R_f$=0.45 (10% MeOH/$CH_2Cl_2$); mp: 162–163° C.; $^1$H NMR ($CD_3OD$): δ 7.53–7.23 (m, 7H, Ar—H), 3.48 (s, 3H, $CH_3$), 2.70 (q, J=7.6 Hz, 2H, $CH_2$), 1.26 (t, J=7.6 Hz, 3H, $CH_3$); MS(EI): m/e 322 ($M^+$ for the free base); Anal.: $C_{16}H_{17}Cl_2N_3$.HCl; Calcd. (%): C: 53.57, H: 5.05, N: 11.71; Found (%): C: 53.66, H: 5.20, N: 11.71.

EXAMPLE 2

Preparation of N-(3-ethylphenyl)-N-methyl-N'-(2,5-dibromophenyl)guanidine hydrochloride (Formula I: hydrochloride salt of R=3-ethylphenyl, $R^1$=$CH_3$, $R_2$=H, $R_3$=$R_4$=Br, n=0).

Part 1: Preparation of 2,5-dibromoaniline hydrochloride

To a solution of 2,5-dibromoaniline (Aldrich, 1.5 g, 6 mmol) in methanol (5 mL) was added methanolic HCl (1M, 30 mL) at 4° C., then the reaction mixture was stirred at 25° C. for 30 minutes. The reaction mixture became a light brown solution with a white precipitate. The precipitate was collected by filtration, washed with diethylether (2 mL), and dried under vacuum to afford 1.6 g of 2,5-dibromoaniline hydrochloride (93% yield).

Part 2: Guanidine Synthesis

A mixture of N-(3-ethylphenyl)-N-methylcyanamide (520 mg, 3.3 mmol), 2,5-dibromoaniline hydrochloride (861 mg, 3 mmol), and chlorobenzene (2 mL) were combined in a dry round bottom flask equipped with water cooled condenser under nitrogen and placed in a preheated oil bath (150–160° C.). The reaction mixture was heated for 3 hours. After cooling, the crude reaction product was purified by crystallization from chlorobenzene/diethylether. The resulting crystals were collected by filtration, washed with diethylether, and dried in a vacuum oven (40° C., 15 hours) to yield the title compound, N-(3-ethylphenyl)-N-methyl-N'-(2,5-dibromophenyl)guanidine hydrochloride, as a white solid (780 mg, 59% yield).

TLC: $R_f$=0.5 (10% MeOH/$CH_2Cl_2$); mp: 217–218° C.; $^1$H NMR ($CD_3OD$): δ 7.56–7.20 (m, 7H, Ar—H), 3.41 (s, 3H, $CH_3$), 2.62 (q, J=7.7 Hz, 2H, $CH_2$), 1.18 (t, J=7.7 Hz, 3H, $CH_3$); MS(EI): m/e 411 ($M^+$ for the free base); Anal.: $C_{16}H_{17}Br_2N_3$.HCl; Calcd. (%): C: 42.93, H: 4.05, N: 9.39; Found (%): C: 42.90, H: 4.01, N: 9.13.

EXAMPLE 3

Preparation of N-(3-ethylphenyl)-N'-(2,5-dichlorophenyl)guanidine mesylate (Formula I: mesylate of R=3-ethylphenyl, $R^1$=$R^2$=H, $R^3$=$R^4$=Cl, n=0).

Part 1: Preparation of 2,5-dichlorophenylcyanamide

To a heterogeneous slurry of 2,5-dichloroaniline (3.0 g, 18.5 mmol) in 60 mL of water at 4° C. was added solid BrCN (1.22 g, 11.3 mmol) slowly. After 5 minutes the cooling bath was removed and the heterogeneous reaction mixture was stirred at room temperature for 24 hours to yield the product in water suspension. The product was collected by filtration, washed with water (100 mL), and dried under vacuum to yield the pure product (2 g, 60% yield).

Part 2: Preparation of 3-ethylaniline mesylate

To a solution of 3-ethylaniline (Aldrich, 4.84 g, 40 mmol) in methanol (10 mL) was added methanesulfonic acid (4.4 g, 45 mmol) at 4° C., then the reaction mixture was stirred at 25° C. for 30 minutes to yield a solution with white precipitates. The precipitates were collected by filtration, washed with ether, and dried under vacuum to afford 7.7 g of 3-ethylaniline mesylate (7.7 g, 91% yield).

Part 3: Guanidine Synthesis

A mixture of 2,5-dichlorophenylcyanamide (1.02 g, 5.5 mmol), 3-ethylaniline mesylate (1.1 g, 5 mmol), and chlorobenzene (15 mL) were combined in a dry round bottom flask equipped with a water cooled condenser under nitrogen and placed in a preheated oil bath (150–160° C.). The reaction mixture was heated for 2 hours. After cooling, the crude reaction product was purified by crystallization from chlorobenzene/diethylether. The resulting crystals were collected by filtration, washed with diethylether, and dried in a vacuum oven (40° C., 15 hours) to yield the title compound, N-(3-ethylphenyl)-N'-(2,5-dichlorophenyl)guanidine mesylate, as a white solid (1.5 g, 75% yield).

TLC: $R_f$=0.4 (10% MeOH/$CH_2Cl_2$); mp: 220–221° C.; $^1$H NMR (300 MHz, $CD_3OD$): δ 7.58–7.17 (m, 7H, Ar—H), 2.68 (s, 3H, $SO_3CH_3$), 2.68 (m, 2H, $CH_2$), 1.24 (t, J=7.6 Hz, $CH_3$); Anal: $C_{16}H_{19}Cl_2N_3O_3$; Calcd. (%): C: 47.83, H: 4.74, N: 10.39; Found (%): C: 47.44, H: 4.64, N: 10.27.

EXAMPLE 4

Preparation of N-(3-ethylphenyl)-N'-(2-chloro-5-ethylphenyl)guanidine mesylate (Formula I: mesylate of R=3-ethylphenyl, $R^1$=$R^2$=H, $R^3$=Cl, $R^4$=$CH_2CH_3$, n=0).

Part 1: Preparation of 2-chloro-5-ethylphenylcyanamide

To a heterogeneous slurry of 2-chloro-5-ethylaniline (1.6 g, 10 mmol) in 60 mL of water at 4° C. was added solid BrCN (0.848 g, 8 mmol) slowly. After 5 minutes the cooling bath was removed and the heterogeneous reaction mixture was stirred at room temperature for 24 hours to yield the product in water suspension. The precipitates were collected by filtration, washed with water (100 mL), and dried under vacuum to yield the pure title compound (1.45 g, 80% yield).

Part 2: Guanidine Synthesis

A mixture of 2-chloro-5-ethylphenylcyanamide (0.6 g, 3.08 mmol), 3-ethylaniline mesylate (0.64 g, 2.93 mmol), and chlorobenzene (12 mL) were combined in a dry round bottom flask equipped with a water cooled condenser under nitrogen and placed in a preheated oil bath (150–160° C.). The reaction mixture was heated for 3 hours. After cooling, the crude reaction product was purified by crystallization from chlorobenzene/diethylether. The resulting crystals were collected by filtration, washed with diethylether, and dried in a vacuum oven (40° C., 15 hours) to yield the title compound, N-(3-ethylphenyl)-N'-(2-chloro-5-ethylphenyl) guanidine mesylate, as a white solid (1.1 g, 91% yield).

TLC: $R_f$=0.4 (10% MeOH/$CH_2Cl_2$); mp: 162–163° C.; $^1$H NMR (300 MHz, $CD_3OD$): δ 7.48–7.17 (m, 7H, Ar—H), 2.69 (s, 3H, $SO_3CH_3$), 2.67 (q, J=7.6 Hz, 4H), ($H_2$), 1.24 (t, J=7.5 Hz, 6H, $CH_3$); Anal.: $C_{18}H_{24}ClN_3SO_3$; Calcd. (%): C: 54.33, H: 6.08, N: 10.56; Found (%): C: 53.98, H: 6.14, N: 10.40.

EXAMPLE 5

Other substituted aniline intermediates, suitable for reaction with an appropriate cyanamide compound to provide compounds of the invention as described above, are either commercially available or can be prepared by methods generally known to those skilled in the synthesis art. The following Examples 5a through 5d disclose procedures for preparation of four different substituted aniline compounds that are suitably used to prepare compounds of the invention, including e.g. the compounds of Examples 23, 58, 64, 69 and 70 which follow.

EXAMPLE 5a

Preparation of 2-Bromo-5-methylthioaniline hydrochloride

To a stirred solution (cooled to 16–19° C.) of 2-bromo-5-(methylthio)benzoic acid (1.5 g, 6.07 mmol, prepared by the method described in Kuenzle, F., et al., *Helv. Chim. Acta.*, 52(3):622–628 (1969)) in DMF (17 mL) was added triethylamine (1.05 mL, 7.28 mmol). After stirring briefly, diphenyphosphoryl azide (1.7 mL, 7.59 mmol) was added by an addition funnel over a 15 minute period. After 2 hours of stirring at ambient temperature, thin layer chromatography ($SiO_2$, cyclohexane/ethyl acetate 8:1) showed the reaction was completed. To this solution was added distilled water (7 mL) and the mixture was then heated to 65° C. for 2 hours.

The reaction mixture was concentrated in vacuo at 45° C. to afford a light yellow, syrupy residue. After adding water (50 mL) to this residue, saturated potassium carbonate was added until pH 9. The mixture was then extracted with 40 mL of methylene chloride two times. The combined extracts were washed with brine, dried over $MgSO_4$ and concentrated in vacuo to yield a yellow oil. The yellow oil was dissolved in 10 mL of ether and added HCl/ether (10 mL, 1N) to provide a white precipitate. The solid was collected by filtration and further purified by column chromatography ($SiO2_2$, hexanes/EtOAc: 100% -80%). The final product was a white solid (0.6 g, 39% in yield); $^1$H NMR ($CD_3OD$): δ (ppm) 7.76 (d, 1H, 8.5 Hz), 7.20 (s, 1H), 7.18 (d, 1H), 2.50 (s, 3H, $CH_3$); Anal: $C_7H_8BrNS.HCl$; Calcd. (%): C: 33.03, H: 3.56, N: 5.50; Found (%): C: 33.00, N: 3.52, N: 5.59.

EXAMPLE 5b

Preparation of N-Methyl-3-methylsulfinylaniline hydrochloride

Part 1: N-Methyl-(3-methylthiophenyl)amine:

3-Methylmercaptoaniline (5 g, 34.8 mmol) was dissolved in formic acid (1.92 mL, 49 mmol) and heated to 100–105° C. under argon for overnight. The reaction mixture was cooled to room temperature and extracted with $CH_2Cl_2$ (75 ml). The organic layer was washed with saturated $Na_2CO_3$ (30 ml) three times and dried over $MgSO_4$, filtered to remove $MgSO_4$ and the solution concentrated to afford the formamide. The formamide was dissolved in anhydrous THF (30 ml) under argon. To this solution was added slowly $LiAlH_4$ in THF (50 ml, 1 M) at 0–5° C. The reaction was warmed up to room temperature and stirred for 20 hours. To this reaction mixture was added 50 ml of saturated aqueous $MgSO_4$. The organic layer was saved. The water layer was further extracted with ethyl acetate (50 ml) three times and the combined organic solution was washed with $H_2O$ (50 ml), brine (50 ml) and dried over $MgSO_4$. The solution was filtered to remove $MgSO_4$ and then concentrated to yield the crude product which was purified by column chromatography ($SiO_2$, hexanes/EtOAc: 8/1). The fractions which contained the product were collected and concentrated, dried under vacuum to yield the pure N-Methyl-(3-methylthiophenyl)amine (5.25 g, 98% in yield).

Part 2: N-Methyl-3-methylsulfinylaniline hydrochloride

Hydrogen peroxide (30% in water, 10.22 mL, 1 mol, Aldrich) was added to a solution of N-methyl-3-methylmercaptoaniline (3.0 g, 19.6 mmol) in acetone (17 mL) at 0–5° C. The reaction was stirred overnight and then the acetone was removed. A 1N NaOH aqueous solution was added until pH 12, which was then extracted with ether (30 ml) three times. The combined organic layers were dried over $MgSO_4$, and then the solution was filtered to remove $MgSO_4$ and the resulting solution concentrated to yield the crude product of the title compound which was purified by column chromatography (silica gel, eluted by EtOAc/MeOH: 100% -90%). N-Methyl-3-methylsulfinylaniline was obtained and was further converted to its hydrochloride salt (1.82 g, 45% in yield).

$^1$H NMR ($CD_3OD$): δ (ppm) 7.90–7.55 (m, Ar—H, 4H), 3.11 (s, $NCH_3$, 3H), 2.85 (s, $SOCH_3$, 3H); MS(EI): m/e 169 ($M^+$ for the free base); TLC: $R_f$=0.29 ($SiO_2$, EtOAc); M.P.: 137–138° C.

EXAMPLE 5c

Preparation of N-Methyl-3-methylsulfonyl aniline hydrochloride

Hydrogen peroxide (30% in water, 10.22 mL, 1 mol, Aldrich) was added to a solution of N-methyl-3-methylmercaptoaniline (3.0 g, 19.6 mmol) in acetone (17 mL) at 0–5° C. The reaction was stirred for overnight and then the acetone was removed. A 1N NaOH aqueous solution was added until pH 12, which solution was then extracted with 30 ml of ethyl ether three times and the combined organic layers were dried $MgSO_4$. The $MgSO_4$ was removed by filtration and the resulting solution was concentrated to yield the crude product which was purified by column chromatography (silica gel, eluted by EtOAc/MeOH 100% -90%). N-methyl-3-methylsulfonyl aniline was obtained and further converted to its hydrochloride salt (1.8 g, 42% in yield).

$^1$H NMR ($CD_3OD$): δ (ppm) 7.90–7.50 (m, Ar—H, 4H), 3.16 (s, $SO_2CH_3$, 3H), 3.05 (s, $NCH_3$, 3H); MS(EI): m/e 185 ($M^+$: $C_8H_{11}NSO_2$); TLC: $R_f$=0.81 ($SiO_2$, EtOAc); M.P.: 169–170° C.

EXAMPLE 5d

Preparation of 2-Fluoro-5-ethylaniline

Part 1: 3'-Nitro-4'-fluoroacetophenone:

To stirred, pre-cooled fuming nitric acid (40 mL) at −10° C. was added dropwise 4'-fluoroacetophenone (Aldrich, 75 g, 54.3 mmol) over a period of 10 minutes. The temperature was strictly maintained at −9 to −10° C. for a total of 8 hours. The reaction mixture flask was then transferred to the freezer (−10° C.) for storage overnight. In the morning the reaction mixture was poured onto ice (1.5 Kg). The resultant mixture was extracted three times with ether (400 mL). The organic layer was washed four times with NaOH (1N, 300 mL) and brine. Concentration in vacuo afforded a yellow liquid which by thin layer chromatography ($SiO_2$, cyclohexane/ethyl acetate: 2/1) showed one major and two minor products. The crude product was purified over 600 grams of 230–400 mesh silica gel, eluting with a gradient of hexanes-ethyl acetate 10:1 to 3:1. The product containing fractions were concentrated to afford a light yellow liquid (27.6 grams).

Part 2: 3'-Amino-4'-fluoroacetophenone:

To a stirred mixture of 3'-nitro-4'-fluoroacetophenone (10.04 g, 55 mmol) in 72 mL of concentrated hydrochloric acid, was added tin (II) chloride dihydrate (37 grams), in portions. After approximately one third of the material had been added, a rapid rise in the internal reaction temperature (to 95° C.) was noted. The mixture was then heated to reflux for 10 minutes, this resulted in the dissolution of all solids to give a solution. The mixture was then cooled to room temperature and poured onto an ice/water mixture (150 g). The mixture was then further cooled in an ice bath while 50% sodium hydroxide was added until pH 12 was reached. The aqueous layer was extracted twice with ether (50 mL). The combined organic extracts were washed with brine and then dried over sodium sulfate. Removal of the drying agent and in vacuo concentration of the filtrate afforded a yellow-orange oil (8.73 g) which was recrystallized on standing. This material was of sufficient purity to be used directly in the next step (Part 3).

Part 3: 2-Fluoro-5-ethylaniline:

To a stirred mixture of 3'-amino-4'-fluoroacetophenone (7.56 g, 49.4 mmol) in triethylene glycol (60 mL) was added 4.94 g of sodium hydroxide. Neat hydrazine hydrate (7.2 mL) was added to the mixture in one portion via a syringe. This addition resulted in a slight exotherm (temperature around 50°). The reaction flask (three neck, equipped with claisen adapter and receiving flask) was then equipped with a heating mantle and the reaction heated to 100° C. for 1 hour, then 150° C. At the higher temperature distillate began to collect in the receiving flask. After 1 hour at 150° C. the reaction mixture was then heated to 180° C., while still collecting distillate. After 45 minutes at 180° C. thin layer chromatography indicated the complete absence of starting material and the appearance of a single major product. The reaction mixture was cooled to room temperature with an ice bath and poured into 100 mL of water. The aqueous mixture was extracted three times with ether (125 mL). The combined organic extracts were washed once with water, once with brine and then dried over potassium carbonate. Concentration of the organic extracts in vacuo afforded 2-fluoro-5-ethylaniline (6.82 g) as an amber liquid. This material was further purified by column chromatography (silica gel, hexanes/ethyl acetate: 2/1) to give 7.11 grams of product as a viscous liquid.

$^1$H NMR ($CDCl_3$): δ (ppm) 8.0–7.0 (m, Ar—H), 2.52 (q, $CH_2$), 1.20 (t, $CH_3$); MW: 139.18 (for the free base); Anal.: $C_8H_{10}NF$; Calcd. (%): C: 69.04, H: 7.24, N: 10.07; Found (%): C: 69.03; N: 7.49, N: 9.89.

EXAMPLES 6–73

By procedures similar to those employed in Examples 1 through 5 above but using appropriately substituted amine hydrochloride and cyanamide reagents, the following compounds of Formulas I and II were prepared having the specified physical characteristics.

EXAMPLE 6

N-(3-Ethylphenyl)-N-methyl-N'-(2,5-dichlorophenyl)-N'-methylguanidine hydrochloride (Formula I: hydrochloride salt of R=3-ethylphenyl, $R^1=R^2=CH_3$, $R_3=R_4=Cl$, n=0).

white solid; TLC: $R_f$=0.4 (10% $MeOH/CH_2Cl_2$); mp: 161–162° C.; $^1$H NMR (300 MHz, $CD_3OD$): δ 7.38–7.09 (m, 7H, Ar—H), 3.44 (s, 3H, $CH_3$), 3.38 (s, 3H, $CH_3$), 2.51 (q, J=7.6 Hz, 2H, $CH_2$), 1.16 (t, J=7.6 Hz, 3H, $CH_3$); Anal.: ($C_{17}H_{19}Cl_2N_3 \cdot HCl \cdot H_2O$); Calcd. (%): C: 52.26, H: 5.68, N: 10.75; Found (%): C: 51.94, H: 5.59, N: 10.44.

EXAMPLE 7

N-(3-Ethylphenyl)-N'-(2,5-dichlorophenyl)-N'-methylguanidine hydrochloride (Formula I: hydrochloride salt of R=3-ethylphenyl, $R^1$=H, $R^2=CH_3$, $R^3=R^4=Cl$, n=0).

white solid; TLC: $R_f$=0.4 (10% $MeOH/CH_2Cl_2$); mp=92–93° C., $^1$H NMR (300 MHz, $CD_3OD$): δ 7.76–7.12 (m, 7H, Ar—H), 3.44 (s, 3H, $CH_3$), 2.68 (q, J=7.6 Hz, 2H, $CH_2$), 1.24 (t, J=7.6 Hz, 3H, $CH_3$); Anal.: ($C_{16}H_{17}Cl_2N_3 \cdot HCl$), Calcd. (%) C: 53.58, H: 5.06, N: 11.91; Found (%): C: 53.49, H: 5.20, N: 11.92; MS (EI)=m/e 321 ($M^+$ for the free base).

EXAMPLE 8

N-(3-Ethylphenyl)-N'-(2,5-dichlorophenyl)guanidine hydrochloride (Formula I: hydrochloride salt of R=3-ethylphenyl, $R^1=R^2$=H, $R^3=R^4=Cl$, n=0).

white solid; TLC: $R_f$=0.4 (10% $MeOH/CH_2Cl_2$); mp: 111–112° C.; $^1$H NMR (300 MHz, $CD_3OD$): δ 7.58–7.15 (m, 7H, Ar—H), 2.68 (q, J=7.6 Hz, 2H, $CH_2$), 1.24 (t, J=7.6 Hz, 3H, $CH_3$); MS (EI): m/e 308 ($M^+$ for the free base); Anal.: ($C_{15}H_{15}Cl_2N_3 \cdot HCl$); Calcd. (%): C: 52.27, H: 4.68, N: 12.19; Found (%): C: 52.17, H: 4.76, N: 12.25.

EXAMPLE 9

N-(3-Ethylphenyl)-N-methyl-N'-(2,5-dibromophenyl)-N'-methylguanidine hydrochloride (Formula I: hydrochloride salt of R=3-ethylphenyl, $R^1=R^2=CH_3$, $R^3=R^4=Br$, n=0).

white solid; TLC: $R_f$=0.3 (10% $MeOH/CH_2Cl_2$); mp: 179–180° C.; $^1$H NMR (300 MHz, $CD_3OD$): δ 7.48–7.10 (m, 7H, Ar—H), 3.45 (s, 3H, $CH_3$), 3.38 (s, 3H, $CH_3$), 2.52 (q, J=7.7 Hz, 2H, $CH_2$), 1.18 (t, J=7.7 Hz, 3H, $CH_3$); MS (EI): m/e 425 ($M^+$ for the free base); Anal.: ($C_{17}H_{19}Br_2N_3 \cdot HCl$); Calcd. (%): C: 44.23, H: 4.37, N: 9.10; Found (%): C: 44.00, H: 4.57, N: 9.04.

EXAMPLE 10

N-(3-Ethylphenyl)-N'-(2,5-dibromophenyl)guanidine hydrochloride (Formula I: hydrochloride salt of R=3-ethylphenyl, $R^1=R^2$=H, $R^3=R^4=Br$, n=0).

white solid; TLC: $R_f$=0.54 (10% $MeOH/CH_2Cl_2$); mp: 76–77° C.; $^1$H NMR (300 MHz, $CD_3OD$): δ 7.70–7.15 (m, 7H, Ar—H), 2.67 (q, J=7.6 Hz, 2H, $CH_2$), 1.24 (t, J=7.6 Hz, 3H, $CH_3$); MS (EI): m/e 397 ($M^+$ for the free base); HRMS: 394.9618 (394.9632 calculated for $C_{15}H_{15}Br_2N_3$).

EXAMPLE 11

N-(3-Ethylphenyl)-N-methyl-N'-(2-chloro-5-trifluoromethylphenyl)guanidine hydrochloride (Formula I: hydrochloride salt of R=3-ethylphenyl, $R^1$=$CH_3$, $R^2$=H, $R^3$=Cl, $R^4$=$CF_3$, n=0).

white solid; TLC: $R_f$=0.5 (10% MeOH/$CH_2Cl_2$); mp: 180–181° C.; $^1$H NMR: δ 7.76–7.25 (m, 7H, Ar—H), 3.53 (s, 3H, $CH_3$), 2.70 (q, J=7.5 Hz, 2H, $CH_2$), 1.26 (t, J=7.5 Hz, 3H, $CH_3$); MS (EI): m/e 355 ($M^+$ for the free base); Anal.: ($C_{17}H_{17}ClF_3N_3$·HCl); Calcd. (%): C: 52.05, H: 4.63, N: 10.71; Found (%): C: 52.15, H: 4.53, N: 10.72.

EXAMPLE 12

N-(3-Ethylphenyl)-N'-(2-chloro-5-trifluoromethylphenyl)guanidine hydrochloride (Formula I: hydrochloride salt of R=3-ethylphenyl, $R^1$=$R^2$=H, $R^3$=Cl, $R^4$=$CF_3$, n=0).

white solid; TLC: $R_f$=0.4 (10% MeOH/$CH_2Cl_2$); mp: 73–74° C.; $^1$H NMR: δ 7.55–7.16 (m, 7H, Ar—H), 2.60 (q, J=7.6 Hz, 2H, $CH_2$), 1.21 (t, J=7.6 Hz, 3H, $CH_3$); MS (EI): m/e 341 ($M^+$ for the free base); HRMS: 341.0907 (341.0917 calculated for $C_{16}H_{15}ClF_3N_3$).

EXAMPLE 13

N-(3-Ethylphenyl)-N-methyl-N'-(2-bromo-5-trifluoromethylphenyl)guanidine hydrochloride (Formula I: hydrochloride salt of R=3-ethylphenyl, $R^1$=$CH_3$, $R^2$=H, $R^3$=Br, $R^4$=$CF_3$, n=0).

white solid; TLC: $R_f$=0.5 (10% MeOH/$CH_2Cl_2$); mp: 184–185° C.; $^1$H NMR: δ 7.93–7.28 (m, 7H, Ar—H), 3.50 (s, 3H, $CH_3$), 2.70 (q, J=7.6 Hz, 2H, $CH_2$), 1.25 (t, J=7.6 Hz, 3H, $CH_3$); MS (EI): m/e 400 ($M^+$ for the free base); Anal.: ($C_{17}H_{17}BrF_3N_3$·HCl); Calcd. (%): C: 46.76, H: 4.15, N: 9.62; Found (%): C: 46.57, H: 4.12, N: 9.36.

EXAMPLE 14

N-(3-Ethylphenyl)-N'-(2-bromo-5-trifluoromethylphenyl)guanidine hydrochloride (Formula I: hydrochloride salt of R=3-ethylphenyl, $R^1$=$R^2$=H, $R^3$=Br, $R^4$=$CF_3$, n=0).

white solid; TLC: $R_f$=0.4 (10% MeOH/$CH_2Cl_2$); mp: 109–110° C.; $^1$H NMR: δ 7.77–7.17 (m, 7H, Ar—H), 2.61 (q, J=7.7 Hz, 2H, $CH_2$); MS(EI): m/e 386 ($M^+$ for the free base); HRMS: 385.0391 (385.0401 calculated for $C_{16}H_{15}BrF_3N_3$).

EXAMPLE 15

N-(3-Ethylphenyl)-N-methyl-N'-(2-fluoro-5-trifluoromethylphenyl)guanidine hydrochloride (Formula I: hydrochloride salt of R=3-ethylphenyl, $R^1$=$CH_3$, $R^2$=H, $R^3$=F, $R^4$=$CF_3$, n=0).

white solid; TLC: $R_f$=0.5 (10% MeOH/$CH_2Cl_2$); mp: 158–159° C.; $^1$H NMR: δ 8.20–7.20 (m, 7H, Ar—H), 3.43 (s, 3H, $CH_3$), 2.61 (q, J=7.6 Hz, 2H, $CH_2$), 1.17 (t, J=7.6 Hz, 3H, $CH_3$); MS (EI): m/e 339 ($M^+$ for the free base); Anal.: ($C_{17}H_{17}F_4N_3$·HCl); Calcd. (%): C: 54.33, H: 4.83, N: 11.18; Found (%): C: 54.20, H: 4.90, N: 11.04.

EXAMPLE 16

N-(3-Ethylphenyl)-N'-(2-fluoro-5-trifluoromethylphenyl)guanidine hydrochloride (Formula I: hydrochloride salt of R=3-ethylphenyl, $R^1$=$R^2$=H, $R^3$=F, $R^4$=$CF_3$, n=0).

white solid; TLC: $R_f$=0.4 (10% MeOH/$CH_2Cl_2$); mp: 105–106° C.; $^1$H NMR: δ 7.25–6.85 (m, 7H, Ar—H), 2.60 (q, J=7.7 Hz, 2H, $CH_2$), 1.21 (t, J=7.6 Hz, 3H, $CH_3$); MS (EI): m/e 325 ($M^+$ for the free base); HRMS: 325.1212 (325.1202 calculated for $C_{16}H_{15}N_3F_4$).

EXAMPLE 17

N-(3-Ethylphenyl)-N-methyl-N'-(2-chloro-5-ethylphenyl)-N'-methylguanidine hydrochloride (Formula I: hydrochloride salt of R=3-ethylphenyl, $R^1$=$R^2$=$CH_3$, $R^3$=Cl, $R^4$=$CH_2CH_3$, n=0).

white solid; TLC: $R_f$=0.3 (10% MeOH/$CH_2Cl_2$); mp: 129–130° C.; $^1$H NMR (300 MHz, $CD_3OD$): δ 7.28–7.01 (m, 7H, Ar—H), 3.42 (s, 3H, $CH_3$), 3.39 (s, 3H, $CH_3$), 2.49 (q, J=7.6 Hz, 2H, $CH_2$), 2.34 (q, J=7.6 Hz, 2H, $CH_2$), 1.13 (t, J=7.7 Hz, 3H, $CH_3$), 1.05 (t, J=7.7 Hz, 3H, $CH_3$); MS (EI): m/e 330 ($M^+$ for the free base).

EXAMPLE 18

N-(3-Ethylphenyl)-N-methyl-N'-(2-chloro-5-ethylphenyl)guanidine hydrochloride (Formula I: hydrochloride salt of R=3-ethylphenyl, $R^1$=$CH_3$, $R^2$=H, $R^3$=Cl, $R^4$=$CH_2CH_3$, n=0).

white solid; TLC: $R_f$=0.4 (10% MeOH/$CH_2Cl_2$); mp: 190–191° C.; $^1$H NMR (300 MHz, $CD_3OD$): δ 7.44–7.20 (m, 7H, Ar—H), 3.48 (s, 3H, $CH_3$), 2.71 (q, J=7.6 Hz, 2H, $CH_2$), 2.65 (J=7.6 Hz, 2H, $CH_2$), 1.27 (t, J=7.7 Hz, 3H, $CH_3$), 1.23 (t, J=7.7 Hz, 3H, $CH_3$); MS (EI): m/e 315 ($M^+$ for the free base); Anal.: ($C_{18}H_{22}ClN_3$·HCl); Calcd. (%): C: 61.36, H: 6.58, N: 11.93; Found (%): C: 61.09, H: 6.37, N: 11.86.

EXAMPLE 19

N-(3-Ethylphenyl)-N'-(2-chloro-5-ethylphenyl)guanidine hydrochloride (Formula I: hydrochloride salt of R=3-ethylphenyl, $R^1$=$R^2$=H, $R^3$=Cl, $R^4$=$CH_2CH_3$, n=0).

white solid; TLC: $R_f$=0.5 (10% MeOH/$CH_2Cl_2$); mp: 77–78° C.; $^1$H NMR (300 MHz, $CD_3OD$): δ 7.49–7.18 (m, 7H, Ar—H), 2.69 (q, J=7.6 Hz, 4H, $CH_2$), 1.24 (t, J=7.6 Hz, 6H, $CH_3$); MS (EI): m/e301 ($M^+$ for the free base); Anal.: ($C_{17}H_{20}ClN_3$·HCl); Calcd. (%): C: 60.36, H: 6.26, N: 12.42; Found (%): C: 60.33, H: 6.42, N: 12.37.

EXAMPLE 20

N-(3-Ethylphenyl)-N-methyl-N'-(2-bromo-5-ethylphenyl)guanidine hydrochloride (Formula I: hydrochloride salt of R=3-ethylphenyl, $R^1$=$CH_3$, $R^2$=H, $R^3$=Br, $R^4$=$CH_2CH_3$, n=0).

white solid; TLC: $R_f$=0.4 (10% MeOH/$CH_2Cl_2$); mp: 189–190° C.; $^1$H NMR (300 MHz, $CD_3OD$): δ 7.62–7.18 (m, 7H, Ar—H), 3.49 (s, 3H, $CH_3$), 2.71 (q, J=7.6 Hz, 2H, $CH_2$), 2.64 (q, J=7.6 Hz, 2H, $CH_2$), 1.26 (t, J=7.6 Hz, 3H, $CH_3$), 1.23 (t, J=7.7 Hz, 3H, $CH_3$); MS (EI): m/e 360 ($M^+$ for the free base); Anal.: ($C_{18}H_{22}BrN_3$·HCl); Calcd. (%): C: 54.49, H: 5.84, N: 10.59; Found (%): C: 54.46, H: 5.95, N: 10.62.

EXAMPLE 21

N-(3-Ethylphenyl)-N'-(2-bromo-5-ethylphenyl)guanidine hydrochloride (Formula I: hydrochloride salt of R=3-ethylphenyl, $R^1$=$R^2$=H, $R^3$=Br, $R^4$=$CH_2CH_3$, n=0).

white solid; TLC: $R_f$=0.54 (10% MeOH/$CH_2Cl_2$); mp: 70–71° C.; $^1$H NMR (300 MHz, $CD_3OD$): δ 7.62–7.10 (m, 7H, Ar—H), 2.71–2.62 (m, 4H, $CH_2$), 1.27 (t, J=7.6 Hz, 3H, $CH_3$), 1.22 (t, J=7.7 Hz, 3H, $CH_3$); Anal.: ($C_{17}H_{20}BrN_3$·HCl); Calcd. (%): C: 53.35, H: 5.53, N: 10.98;

Found (%): C: 53.61, H: 5.56, N: 11.04; MS(EI): m/e 345 (M⁺ for the free base).

EXAMPLE 22

N-(3-Ethylphenyl)-N-methyl-N'-(2-fluoro-5-ethylphenyl) guanidine hydrochloride (Formula I: hydrochloride salt of R=3-ethylphenyl, $R^1=CH_3$, $R^2=H$, $R^3=F$, $R^4=CH_2CH_3$, n=0).

white solid; TLC: $R_f$=0.4 (10% MeOH/$CH_2Cl_2$); mp: 171–172° C.; $^1$H NMR (300 MHz, $CD_3OD$): δ 7.45–7.14 (m, 7H, Ar—H), 3.48 (s, 3H, $CH_3$), 2.70 (q, J=7.6 Hz, 2H, $CH_2$), 2.64 (q, J=7.5 Hz, 2H, $CH_2$), 1.26 (t, J=7.7 Hz, 3H, $CH_3$), 1.22 (t, J=7.5 Hz, 3H, $CH_3$); MS (EI): m/e 299 (M⁺ for the free base); Anal.: ($C_{18}H_{22}FN_3$.HCl); Calcd. (%): C: 64.37, H: 6.90, N: 12.51; Found (%): C: 64.49, N: 7.01, N: 12.45.

EXAMPLE 23

N-(3-Ethylphenyl)-N'-(2-fluoro-5-ethylphenyl)guanidine hydrochloride (Formula I: hydrochloride salt of R=3-ethylphenyl, $R^1=R^2=H$, $R^3=F$, $R^4=CH_2CH_3$, n=0).

white solid; TLC: $R_f$=0.3 (10% MeOH/$CH_2Cl_2$); mp=52.53° C.; $^1$H NMR (300 MHz, $CD_3OD$): δ 7.34–7.11 (m, 7H, Ar—H), 2.70–2.61 (m, 4H, $CH_2$), 1.26–1.20 (m, 6H, $CH_3$); Anal.: ($C_{17}H_{20}FN_3$.HCl); Calcd. (%): C: 63.45, H: 6.58, N: 13.06; Found (%): C: 63.52, H: 6.77, N: 13.32; MS(EI): m/e 285 (M⁺ for the free base).

EXAMPLE 24

N-(3-Ethylphenyl)-N-methyl-N'-(2-chloro-5-methylphenyl)guanidine hydrochloride (Formula I: hydrochloride salt of R=3-ethylphenyl, $R^1=CH_3$, $R^2=H$, $R^3=Cl$, $R^4=CH_3$, n=0).

white solid; TLC: $R_f$=0.45 (10% MeOH/$CH_2Cl_2$); mp: 204–205° C.; $^1$H NMR (300 MHz, $CD_3OD$): δ 7.46–7.16 (m, 7H, Ar—H), 3.48 (s, 3H, $CH_3$), 2.70 (q, J=7.6 Hz, 2H, $CH_2$), 2.33 (s, 3H, $CH_3$), 1.26 (t, J=7.6 Hz, 3H, $CH_3$); MS (EI): m/e 302 (M⁺ for the free base); Anal.: ($C_{17}H_{20}ClN_3$.HCl); Calcd. (%): C: 60.36, H: 6.26, N: 12.42; Found (%): C: 60.23, H: 6.50, N: 12.32.

EXAMPLE 25

N-(3-Ethylphenyl)-N'-(2-chloro-5-methylphenyl) guanidine hydrochloride (Formula I: hydrochloride salt of R=3-ethylphenyl, $R^1=R^2=H$, $R^3=Cl$, $R^4=CH_3$, n=0).

white solid; TLC: $R_f$=0.35 (10% MeOH/$CH_2Cl_2$); mp: 88–89° C.; $^1$H NMR (300 MHz, $CD_3OD$): δ 7.45–7.18 (m, 7H, Ar—H), 2.69 (q, J=7.7 Hz, 2H, $CH_2$), 2.37 (s, 3H, $CH_3$), 1.25 (t, J=7.7 Hz, 3H, $CH_3$); MS (EI): m/e 288 (M⁺ for the free base); Anal.: ($C_{16}H_{18}ClN_3$.HCl.0.5$H_2O$); Calcd. (%): C: 57.66, H: 6.05, N: 12.61; Found (%): C: 57.36, H: 6.08, N: 12.46.

EXAMPLE 26

N-(3-Ethylphenyl)-N-methyl-N'-(2-chloro-5-methylthiophenyl)guanidine hydrochloride (Formula I: hydrochloride salt of R=3-ethylphenyl, $R^1=CH_3$, $R^2=H$, $R^3=Cl$, $R^4=SCH_3$, n=0).

white solid; TLC: $R_f$=0.45 (10% MeOH/$CH_2Cl_2$); mp: 198–199° C.; MS (EI): m/e 333 (M⁺ for the free base); $^1$H NMR ($CD_3OD$): δ 7.45–7.20 (m, 7H, Ar—H), 3.49 (s, 3H, $CH_3$), 2.70 (q, J=7.5 Hz, 2H, $CH_2$), 2.49 (s, 3H, $SCH_3$), 1.26 (t, J=7.5 Hz, 3H, $CH_3$); Anal.: ($C_{17}H_{20}ClN_3S$.HCl); Calcd. (%): C: 55.14, H: 5.72, N: 11.35; Found (%): C: 54.99, H: 5.63, N: 11.23.

EXAMPLE 27

N-(3-Ethylphenyl)-N'-(2-chloro-5-methylthiophenyl) guanidine hydrochloride (Formula I: hydrochloride salt of R=3-ethylphenyl, $R^1=R^2=H$, $R^3=Cl$, $R^4=SCH_3$, n=0).

white solid; TLC: $R_f$=0.45 (10% MeOH/$CH_2Cl_2$); mp=132–133° C.; $^1$H NMR ($CD_3OD$): δ 7.50–7.18 (m, 7H, Ar—H), 2.69 (q, J=7.6 Hz, 2H, $CH_2$), 2.51 (s, 3H, $CH_3$), 1.25 (t, J=7.6 Hz, 3H, $CH_3$); Anal.: ($C_{16}H_{18}ClN_3S$.HCl); Calcd. (%): C: 53.93, N: 11.79, H: 5.37; Found (%): C: 54.09, N: 11.72, H: 5.44.

EXAMPLE 28

N-(1-Naphthyl)-N'-(2-fluoro-5-methylphenyl)guanidine hydrochloride (Formula I: hydrochloride salt of R=1-naphthyl, $R^1=R^2=H$, $R^3=F$, $R^4=CH_3$, n=0).

white solid; mp 194° C.; $^1$H NMR (300 MHz, $CD_3OD$): δ 7.98–8.15 (m, 2, Ar—H), 7.57–7.68 (m, 3, Ar—H) 7.15–7.24 (d, 5, Ar—H); 2.35 (s, 3, $CH_3$); MS (EI); m/e 293 (M⁺ for free base).

EXAMPLE 29

N-(1-Naphthyl)-N'(2,5-dichlorophenyl)-N'-methylguanidine hydrochloride (Formula I: hydrochloride salt of R=1-naphthyl, $R^1=H$, $R^2=CH_3$, $R^3=R^4=Cl$, n=0).

white solid; mp 210° C., $^1$H NMR (300 MHz, $CD_3OD$): δ 7.96–8.02 (m, 3, Ar—H), 7.48–7.64 (m, 7, Ar—H); 3.52 (s, 3, N—$CH_3$); MS (EI): m/e 344 (M⁺ for free base); Anal.: ($C_{18}H_{15}Cl_2N_3$.HCl.0.25 $H_2O$); Calcd. (%): C: 56.13, H: 4.32, N: 10.91; Found (%): C: 56.02, H: 4.60, N: 10.73.

EXAMPLE 30

N-(1-Naphthyl)-N'(2-chloro-5-methylphenyl)guanidine hydrochloride (Formula I: hydrochloride salt of R=1-naphthyl, $R^1=R^2=H$, $R^3=Cl$, $R^4=CH_3$, n=0).

white solid; mp 125° C.; $^1$H NMR (300 MHz, $CD_3OD$): δ 7.95–8.10 (m, 3, Ar—H), 7.52–7.70 (m, 6, Ar—H); 7.41–7.48 (d, 1, Ar—H); 7.30–7.35 (s, 1, Ar—H); 7.20–7.25 (m, 2, Ar—H); 2.37 (s, 3, Ar—$CH_3$); MS (EI): m/e 310 (M⁺ for free base); Anal.: ($C_{18}H_{16}ClN_3$.HCl); Calcd. (%): C: 62.44, H: 4.95, N: 12.14; Found (%): C: 62.52, H: 5.04, N: 11.96.

EXAMPLE 31

N-(1-Naphthyl)-N'-(2,5-dimethylphenyl)guanidine hydrochloride (Formula I: hydrochloride salt of R=1-naphthyl, $R^1=R^2=H$, $R^3=R^4=CH_3$, n=0).

white solid; mp 122–123° C.; $^1$H NMR (300 MHz, $CD_3OD$): δ 7.95–8.08 (m, 3, Ar—H), 7.55–7.71 (m, 4, Ar—H); 7.10–7.28 (m, 3, Ar—H); 2.32 (s, 6, 2 Ar—$CH_3$); MS (EI): m/e 289 (M⁺ for free base); Anal.: ($C_{19}H_{19}N_3$.HCl); Calcd. (%): C: 70.04, H: 6.19, N: 12.90; Found (%): C: 70.02, H: 6,20, N: 12.87.

EXAMPLE 32

N-(1-Naphthyl)-N'-(2,5-dibromophenyl)guanidine hydrochloride (Formula I: hydrochloride salt of R=1-naphthyl, $R^1=R^2=H$, $R^3=R^4=Br$, n=0).

white solid; mp 231–232° C.; $^1$H NMR (300 MHz, $CD_3OD$): δ 7.97–8.13 (m, 3, Ar—H), 7.48–7.72 (m, 7, Ar—H); MS (EI): M/e 419 (M⁺ for free base).

EXAMPLE 33

N-(1-Naphthyl)-N'-(2-chloro-5-methylphenyl)-N'-methylguanidine hydrochloride (Formula I: hydrochloride salt of R=1-naphthyl, $R^1=H$, $R^2=CH_3$, $R^3=Cl$, $R^4=CH_3$, n=0).

white solid; mp 228–229° C.; $^1$H NMR (300 MHz, CD$_3$OD): δ 7.96–7.99 (m, 3, Ar—H), 7.48–7.61 (m, 6, Ar—H); 7.26–7.30 (d, 1, Ar—H); 3.50 (s, 3, N—CH$_3$); 2.39 (s, 3, Ar—CH$_3$)I MS (EI): m/e 324 (M$^+$ for free base); Anal.: (C$_{19}$H$_{18}$ClN$_3$.HCl); Calcd. (%): C: 63.34, H: 5.32, N: 11.66; Found (%): C: 63.20, H: 5.43, N: 11.66.

EXAMPLE 34

N-(1-Naphthyl)-N'-(2,5-dimethylphenyl)-N'-methylguanidine hydrochloride (Formula I: hydrochloride salt of R=1-naphthyl, R$^1$=H, R$^2$=CH$_3$, R$^3$=R$^4$=CH$_3$, n=0).

white solid; mp 216–217° C.; $^1$H NMR (300 MHz, CD$_3$OD): δ 7.95–8.00 (m, 2, Ar—H), 7.5–7.7 (m, 4, Ar—H); 7.18–7.38 (m, 4, Ar—H); 3.5 (br s, 3, N—CH$_3$); 2.38 (s, 3, Ar—CH$_3$); MS (EI): m/e 303 (M$^+$ for free base); Anal.: (C$_{20}$H$_{21}$N$_3$.HCl); Calcd. (%): C: 70.68, H: 6,52, N: 12.36; Found (%): C: 70.51, H: 6,46, N: 12.18.

EXAMPLE 35

N-(1-Naphthyl)-N'-(2,5-dibromophenyl)-N-methylguanidine hydrochloride (Formula I: hydrochloride salt of R=1-naphthyl, R$^1$=H, R$^2$=CH$_3$, R$^3$=R$^4$=Br, n=0).

white solid; mp 213° C.; $^1$H NMR (300 MHz, CD$_3$OD): δ 7.94–8.06 (m, 3, Ar—H), 7.54–7.74 (m, 6, Ar—H); 7.2–7.38 (m, 1, Ar—H); 3.5 (br, s, N—CH$_3$); MS (EI): m/e 433 (M$^+$ for free base); Anal.: (C$_{18}$H$_{15}$Br$_2$N$_3$.HCl); Calcd. (%): C: 46.04, H: 3.43, N: 8.95; Found (%): C: 46.15, H: 3.33, N: 8.89.

EXAMPLE 36

N-(1-Naphthyl)-N'-(2-chloro-5-thiomethylphenyl) guanidine hydrochloride (Formula I: hydrochloride salt of R=1-naphthyl, R$^1$=R$^2$=H, R$^3$=Cl, R$^4$=SCH$_3$, n=0).

white solid; mp 175° C.; $^1$H NMR (300 MHz, CD$_3$OD): δ 7.95–8.10 (m, 3, AR—H), 7.55–7.70 (m, 4, Ar—H); 7.46–7.51 (d, J=8 Hz; 1, Ar—H); 7.34–7.39 (s, 1, Ar—H); 7.25–7.32 (dd, 1, Ar—H); 2.51 (s, 3, S—CH$_3$); MS (EI): m/e 342 (M$^+$ for free base); Anal.: (C$_{18}$H$_{16}$ClN$_3$S.HCl.EtOH); Calcd. (%): C: 56.61, H: 5.23, N: 9.90; Found (%): C: 56.71, H: 5.21, N: 10.19.

EXAMPLE 37

N-(1-Naphthyl)-N'-(2-fluoro-5-trifluoromethylphenyl) guanidine hydrochloride (Formula I: hydrochloride salt of R=1-naphthyl, R$^1$=R$^2$=H, R$^3$=F, R$^4$=CF$_3$, n=0).

white solid; mp 149° C.; $^1$H NMR (300 MHz, CD$_3$OD): δ 7.97–8.07 (m, 3, Ar—H), 7.48–7.85 (m, 7, Ar—H); MS (EI): m/e 347 (M$^+$ for free base); Anal.: (C18H$_{13}$F$_4$N$_3$.HCl); Calcd. (%): C: 56.33, H: 3.68, N: 10.95; Found (%): C: 55.91, H: 3.69, N: 10.79.

EXAMPLE 38

N-(1-Naphthyl)-N'-(2-chloro-5-trifluoromethylphenyl) guanidine hydrochloride (Formula I: hydrochloride salt of R=1-naphthyl, R$^1$=R$^2$=H, R$^3$=Cl, R$^4$=CF$_3$, n=0).

white solid; mp 198° C.; $^1$H NMR (300 MHz, CD$_3$OD): δ 8.07–8.09 (d, J=8.5 Hz, 1, Ar—H), 7.98–8.01 (m, 2, Ar—H); 7.56–7.86 (m; 7, Ar—H); MS (EI): m/e 364 (M$^+$ for free base); Anal.: (C$_{18}$H$_{13}$ClF$_3$N$_3$.HCl); Calcd. (%): C: 54.02, H: 3.53, N: 10.50; Found (%): C: 54.16, H: 3.52, N: 10.35.

EXAMPLE 39

N-(1-Naphthyl)-N'-(2-bromo-5-trifluoromethylphenyl) guanidine hydrochloride (Formula I: hydrochloride salt of R=1-naphthyl, R$^1$=R$^2$=H, R$^3$=Br, R$^4$=CF$_3$, n=0).

white solid; mp 234° C.; $^1$H NMR (300 MHz, CD$_3$OD): δ 8.10–8.12 (d, J=9 Hz, 1, Ar—H), 7.97–8.01 (m, 3, Ar—H); 7.86 (s, 1, Ar—H); 7.56–7.70 (m, 5, Ar—H); MS (EI): m/e 408 (M$^+$ for free base); Anal.: (C$_{18}$H$_{13}$BrF$_3$N$_3$.HCl); Calcd. (%): C: 48.62, H: 3.17, N: 9.45; Found (%): C: 48.49, H: 3.11, N: 9.18.

EXAMPLE 40

N-(1-Naphthyl)-N'-(2-thiomethyl-5-trifluoromethylphenyl)guanidine hydrochloride (Formula I: hydrochloride salt of R=1-naphthyl, R$^1$=R$^2$=H, R$^3$=SCH$_3$, R$^4$=CF$_3$, n=0).

white solid; mp 210° C.; $^1$H NMR (300 MHz, CD$_3$OD): δ 8.11–8.14 (d, J=8 Hz, 1, Ar—H), 7.98–8.01 (d, J=7 Hz; 2, Ar—H); 7.55–7.73 (m, 7, Ar—H); 2.62 (3, s, S—CH$_3$); MS (EI): m/e 375 (M$^+$ for free base); Anal.: (C$_{19}$H$_{16}$F$_3$N$_3$S.HCl); Calcd. (%): C: 55.41, H: 4.16, N: 10.20; Found (%): C: 55.27, H: 4.18, N: 10.90.

EXAMPLE 41

N-(1-Naphthyl)-N'-(2-methoxy-5-methylphenyl) guanidine hydrochloride (Formula I: hydrochloride salt of R=1-naphthyl, R$^1$=R$^2$=H, R$^3$=OCH$_3$, R$^4$=CH$_3$; n=0).

white solid; mp 194° C.; $^1$H NMR (300 MHz, CD$_3$OD): δ 8.06–8.09 (d, J=8 Hz, 1, Ar—H), 7.96–8.00 (m, 2, Ar—H); 7.52–7.69 (m, 4, Ar—H); 7.14–7.20 (m, 2, Ar—H); 7.02–7.05 (dd, J=8.5 Hz; 1, Ar—H); 3.94 (s, 3, OCH$_3$); 2.29 (3, s, Ar—CH$_3$); Anal.: (C$_{19}$H$_{19}$N$_3$O.HCl); Calcd. (%): C: 66.76, H: 5.90, N: 12.29; Found (%): C: 66.25, H: 5.89, N: 12.23.

EXAMPLE 42

N-(1-Naphthyl)-N'-(2-chloro-5-ethylphenyl)guanidine hydrochloride (Formula I: hydrochloride salt of R=1-naphthyl, R$^1$=R$^2$=H, R$^3$=Cl, R$^4$=CH$_2$CH$_3$, n=0).

white solid; mp 154° C.; $^1$H NMR (300 MHz, CD$_3$OD): δ 8.07–8.10 (d, J=9 Hz, 1, Ar—H), 7.97–8.01 (m, 2, Ar—H); 7.57–7.69 (m, 4, Ar—H); 7.47–7.50 (d, J=8 Hz, 1, Ar—H); 7.13–7.35 (m, 2, Ar—H); 2.63–2.71 (q, J=7.5 Hz, 2, CH$_2$); 1.21–1.26 (t, J=8 Hz, 3, CH$_3$); MS (EI): m/e 324 (M$^+$ for free base).

EXAMPLE 43

N-(1-Naphthyl)-N'-(2-chloro-5-ethylphenyl)-N'-methylguanidine hydrochloride (Formula I: hydrochloride salt of R=1-naphthyl, R$^1$=H, R$^2$=CH$_3$, R$^3$=Cl, R$^4$=CH$_2$CH$_3$, n=0).

white solid; mp 233° C.; $^1$H NMR (300 MHz, CD$_3$OD): δ 7.97–8.02 (m, 3, Ar—H), 7.52–7.63 (m, 6, Ar—H); 7.31–7.34 (d, J=8 Hz, 1, Ar—H); 3.51 (br s, 3, N—CH$_3$); 2.67–2.74 (q, J=7.5 Hz, 2, CH$_2$); 1.24–1.29 (t, J=8 Hz, 3, CH$_3$); MS (EI): m/e 338 (M$^+$ for free base); Anal.: (C$_{20}$H$_{20}$ClN$_3$.HCl); Calcd. (%): C: 64.18, H: 5.65, N: 11.23; Found (%): C: 63.96, H: 5.83, N: 11.25.

EXAMPLE 44

N-(1-Naphthyl)-N'-(2-bromo-5-ethylphenyl)guanidine hydrochloride (Formula I: hydrochloride salt of R=1-naphthyl, R$^1$=R$^2$=H, R$^3$=Br, R$^4$=CH$_2$CH$_3$, n=0).

white solid; TLC: R$_f$=0.5 (10% MeOH/CH$_2$Cl$_2$); $^1$H NMR (300 MHz, CD$_3$OD): δ 8.09–7.22 (m, 10H, Ar—H), 2.67 (q, J=7.5 Hz, 2H, CH$_2$), 1.24 (t, J=7.5 Hz, 3H, CH$_3$).

EXAMPLE 45

N-(1-Naphthyl)-N'-(2-fluoro-5-ethylphenyl)guanidine hydrochloride (Formula I: hydrochloride salt of R=1-naphthyl, R$^1$=R$^2$=H, R$^3$=F, R$^4$=CH$_2$CH$_3$, n=0).

white solid; TLC: $R_f$=0.5 (10% MeOH/CH$_2$Cl$_2$); $^1$H NMR (300 MHz, CD$_3$OD): δ 8.05–7.19 (m, 10H, Ar—H), 2.65 (q, J=7.5 Hz, 2H, CH$_2$), 1.23 (t, J=7.5 Hz, 3H, CH$_3$).

EXAMPLE 46

N-(1-Naphthyl)-N'-(2-bromo-5-ethylphenyl)guanidine hydrochloride (Formula I: hydrochloride salt of R=1-naphthyl, $R^1$=$R^2$=H, $R^3$=Br, $R^4$=CH$_2$CH$_3$, n=0).

white solid; TLC: $R_f$=0.5 (10% MeOH/CH$_2$Cl$_2$); mp: 145–146° C.; $^1$H NMR (300 MHz, CD$_3$OD): δ 8.09–7.22 (m, 10H, Ar—H), 2.67 (q, J=7.5 Hz, 2H, CH$_2$), 1.24 (t, J=7.5 Hz, 3H, CH$_3$); MS (EI): m/e 367 (M$^+$ for free base).

EXAMPLE 47

N-(1-Naphthyl)-N'-(2-fluoro-5-ethylphenyl)guanidine hydrochloride (Formula I: hydrochloride salt of R=1-naphthyl, $R^1$=$R^2$=H, $R^3$=F, $R^4$=CH$_2$CH$_3$, n=0).

white solid; TLC: $R_f$=0.5 (10% MeOH/CH$_2$Cl$_2$); mp: 100–101° C.; $^1$H NMR (300 MHz, CD$_3$OD): δ 8.05–7.19 (m, 10H, Ar—H), 2.65 (q, J=7.5 Hz, 2H, CH$_2$), 1.23 (t, J=7.5 Hz, 3H, CH$_3$); MS (EI): m/e 307.1 (M$^+$ for the free base); Anal.: (C$_{19}$H$_{18}$FN$_3$.HCl); Calcd. (%): C: 66.37, H: 5.57, H: 12.22; Found (%): C: 66.21, H: 5.50, N: 12.17.

EXAMPLE 48

N-(8-Quinolinyl)-N'-(2-chloro-5-methylphenyl)guanidine hydrochloride (Formula I: hydrochloride salt of R=8-quinolinyl, $R^1$=$R^2$=H, $R^3$=Cl, $R^4$=CH$_3$, n=0).

yellowish solid; mp 150° C.; $^1$H NMR (300 MHz, CD$_3$OD): δ 8.98–8.00 (dd, 1, Ar—H), 8.40–8.44 (dd, 1, Ar—H); 7.93–7.96 (d, 1, Ar—H); 7.82–7.84 (d, 1, Ar—H); 7.61–7.68 (m, 2, Ar—H); 7.38–7.44 (m, 3, Ar—H); 7.21–7.22 (d, 1, Ar—H); 3.30 (s, 3, CH$_3$); MS (EI): m/e 310 (M$^+$ for free base).

EXAMPLE 49

N-(8-Quinolinyl)-N'-(2-chloro-5-ethylphenyl)guanidine hydrochloride (Formula I: hydrochloride salt of R=8-quinolinyl, $R^1$=$R^2$=H, $R^3$=Cl, $R^4$=CH$_2$CH$_3$, n=0).

brown solid; mp 167° C.; $^1$H NMR (300 MHz, CD$_3$OD): δ 8.40–9.25 (m, 2, Ar—H), 7.27–8.34 (m, 7, Ar—H); 2.65–2.72 (q, 2, CH$_2$); 1.22–1.27 (t, 3, CH$_3$); MS (EI): m/e 324 (M$^+$ for free base).

EXAMPLE 50

N-(3-Ethylphenyl)-N-methyl-N'-(2,4,5-trichlorophenyl)guanidine hydrochloride (Formula I: hydrochloride salt of R=3-ethylphenyl, $R^1$=CH$_3$, $R^2$=H, $R^3$=$R^4$=Cl, $R^5$=4-Cl, n=1).

white solid; TLC: $R_f$=0.3 (10% MeOH/CH$_2$Cl$_2$); mp: 164–165° C.; $^1$H NMR (300 MHz, CD$_3$OD): δ 7.79–7.23 (m, 6H, Ar—H), 3.49 (s, 3H, CH$_3$), 2.70 (q, J=7.6 Hz, 2H, CH$_2$), 1.26 (t, J=7.6 Hz, 3H, CH$_3$); MS (EI): m/e 335.0 (M$^+$ for the free base); Anal.: (C$_{16}$H$_{16}$Cl$_3$N$_3$.HCl.1/2H$_2$O); Calcd. (%): C: 47.78, H: 4.51, N: 10.45; Found (%): C: 47.93, H: 4.63, N: 10.33.

EXAMPLE 51

N-(3-Ethylphenyl)-N'-(2,4,5-trichlorophenyl)guanidine hydrochloride (Formula I: hydrochloride salt of R=3-ethylphenyl, $R^1$=$R^2$=H, $R^3$=$R^4$=Cl, $R^5$=4-Cl, n=1).

white solid; TLC: $R_f$=0.4 (10% MeOH/CH$_2$Cl$_2$); mp: 82–83° C.; $^1$H NMR (300 MHz, CD$_3$OD): δ 7.63–7.18 (m, 6H, Ar—H), 2.63 (q, J=7.6 Hz, 2H, CH$_2$), 1.22 (t, J=7.6 Hz, 3H, CH$_3$); MS (EI): m/e 341 (M$^+$ for the free base).

EXAMPLE 52

N-(1-Naphthyl)-N'-(2,4,5-trichlorophenyl)guanidine hydrochloride (Formula I: hydrochloride salt of R=1-naphthyl, $R^1$=$R^2$=H, $R^3$=$R^4$=Cl, $R^5$=4-Cl, n=1).

white solid; TLC: $R_f$=0.4 (10% MeOH/CH$_2$Cl$_2$); mp: 238–239° C.; $^1$H NMR (300 MHz, CD$_3$OD): δ 8.08–7.58 (m, 10H, Ar—H); MS (EI): m/e 363 (M$^+$ for the free base); Anal.: (C$_{17}$H$_{12}$Cl$_3$N$_3$.HCl); Calcd. (%): C: 50.9, H: 3.29, N: 10.48; Found (%): C: 51.11, H: 3.33, N: 10.63.

EXAMPLE 53

N-(3-Ethylphenyl)-N-methyl-N'-(2-bromo-5-methylthiophenyl)guanidine hydrochloride (Formula I: hydrochloride salt of R=3-ethylphenyl, $R^1$=CH$_3$, $R^2$=H, $R^3$=Br, $R^4$=CH$_3$S, n=0).

TLC: $R_f$=0.5 (SiO$_2$, CH$_2$Cl$_2$/MeOH=10/1); M.P.: 90–92° C.; $^1$H NMR (CD$_3$OD): δ (ppm) 7.64–7.15 (m, Ar—H, 7H), 3.49 (s, CH$_3$, 3H), 2.70 (q, J=7.4 Hz, 2H, CH$_2$), 2.47 (s, SCH$_3$, 3H), 1.25 (t, J=7.5 Hz, 3H, CH$_3$); MS (EI): m/e 377 (M$^+$: C$_{17}$H$_{20}$N$_3$Br$_1$S$_1$); Anal. (C$_{17}$H$_{20}$N$_3$Br$_1$S$_1$.HCl); Calcd. (%): C: 49.23, H: 5.1, N: 10.13; Found (%) C: 49.30, H: 5.28, N: 10.28.

EXAMPLE 54

N-(3-Methylthiophenyl)-N-methyl-N'-(2,5-dichlorophenyl)guanidine hydrochloride (Formula I: hydrochloride salt of R=3-methylthiophenyl, $R^1$=CH$_3$, $R^2$=H, $R^3$=$R^4$=Cl, n=0).

TLC: $R_f$=0.3 (10% MeOH/CH$_2$Cl$_2$); MP: 200–201° C.; $^1$H NMR (300 MHz, CD$_3$OD): δ (ppm) 7.55–7.15 (m, 7H, Ar—H), 3.49 (s, 3H, NCH$_3$), 2.52 (s, 3H, SCH$_3$); MS (EI): m/e 339 (M$^+$ for the free base); Anal. (C$_{15}$H$_{15}$Cl$_2$N$_3$S.HCl); Calcd. (%): C: 47.82, H: 4.28, N: 11.15; Found (%): C: 47.66, H: 4.26, N: 11.34.

EXAMPLE 55

N-(3-Methylthiophenyl)-N-methyl-N'-(2,5-dibromophenyl)guanidine hydrochloride (Formula I: hydrochloride salt of R=3-methylthiophenyl, $R^1$=CH$_3$, $R^2$=H, $R^3$=$R^4$=Br, n=0).

TLC: $R_f$=0.4 (10% MeOH/CH$_2$Cl$_2$); MP: 239–240° C.; $^1$H NMR: δ (ppm) 7.70–7.20 (m, 7H, Ar—H), 3.49 (s, 3H, NCH$_3$), 2.53 (s, 3H, SCH$_3$); MS (EI): m/e 429 (M$^+$ for the free base); Anal. (C$_{15}$H$_{15}$Br$_2$N$_3$S.HCl); Calcd. (%): C: 38.69, H: 3.46, N: 9.02; Found (%): C: 38.65, H: 3.60, N: 8.98.

EXAMPLE 56

N-(3-Methylthiophenyl)-N-methyl-N'-(2-chloro-5-ethylphenyl)guanidine hydrochloride (Formula I: hydrochloride salt of R=3-methylthiophenyl, $R^1$=CH$_3$, $R^2$=H, $R^3$=Cl, $R^4$=CH$_2$CH$_3$, n=0).

white solid; TLC: $R_f$=0.3 (10% MeOH/CH$_2$Cl$_2$); MP: 212–213° C.; $^1$H NMR (300 MHz, CD$_3$OD): δ (ppm) 7.45–7.19 (m, 7H, Ar—H), 3.49 (s, 3H, CH$_3$), 2.68 (q, J=7.5 Hz, 2H, CH$_2$), 2.51 (s, 3H, SCH$_3$), 1.22 (t, J=7.5 Hz, 3H, CH$_3$); MS (EI): m/e 333 (M$^+$ for the free base); Anal. (C$_{17}$H$_{20}$ClN$_3$S.HCl); Calcd. (%): C: 55.14, H: 5.72, N: 11.35; Found (%): C: 55.29, H: 5.81, N: 11.36.

EXAMPLE 57

N-(3-Methylthiophenyl)-N-methyl-N'-(2-chloro-5-methylthiophenyl)guanidine hydrochloride (Formula I:

hydrochloride salt of R=3-methylthiophenyl, $R^1=CH_3$, $R^2=H$, $R^3=Cl$, $R^4=SCH_3$, n=0).

TLC: $R_f$=0.25 (10% MeOH/CH$_2$Cl$_2$); MP: 203–204° C.; $^1$H NMR (300 MHz, CD$_3$OD): δ (ppm) 7.50–7.18 (m, 7H, Ar—H), 3.49 (s, 3H, CH$_3$), 2.52 (s, 3H, SCH$_3$), 2.49 (s, 3H, SCH$_3$); MS (EI): m/e 351 (M$^+$ for the free base); Anal. (C$_{16}$H$_{18}$ClN$_3$S$_2$.HCl); Calcd. (%): C: 49.48, H: 4.93, N: 10.82; Found (%): C: 49.41, H: 5.07, N: 10.81.

EXAMPLE 58

N-(3-Methylthiophenyl)-N-methyl-N'-(2-bromo-5-methylthiophenyl)guanidine (Formula I: R=3-methylthiophenyl, $R^1=CH_3$, $R^2=H$, $R^3=Br$, $R^4=SCH_3$, n=0).

TLC: $R_f$=0.43 (SiO$_2$, CH$_2$Cl$_2$/MeOH=10/1); M.P.: 174–175° C.; $^1$H NMR (CD$_3$OD): δ (ppm) 7.65–7.15 (m, Ar—H, 7H), 3.49 (s, CH$_3$, 3H), 2.52 (s, SCH$_3$, 3H), 2.49 (s, SCH$_3$, 3H); HRMS: 395.0120 (Calcd.: 395.0126 for C$_{16}$H$_{18}$N$_3$BrS$_2$); HPLC: 98.47%.

EXAMPLE 59

N-(3-Methylthiophenyl)-N-methyl-N'-(2-bromo-5-ethylphenyl)guanidine hydrochloride (Formula I: hydrochloride salt of R=3-methylthiophenyl, $R^1=CH_3$, $R^2=H$, $R^3=Br$, $R^4=CH_2CH_3$, n=0)

TLC: $R_f$=0.3 (10% MeOH/CH$_2$Cl$_2$); MP: 199–200° C.; $^1$H NMR (300 MHz, CD$_3$OD): δ (ppm) 7.65–7.15 (m, 7H, Ar—H), 3.49 (s, 3H, CH$_3$), 2.64 (q, J=7.5 Hz, 2H, CH$_2$), 2.52 (s, 3H, SCH$_3$), 1.23 (t, J=7.5 Hz, 3H, CH$_3$); MS (EI): m/e 378 (M$^+$ for the free base); Anal. (C$_{17}$H$_{20}$BrN$_3$S.HCl); Calcd. (%): C: 49.23, H: 5.10, N: 10.13; Found (%): C: 49.39, H: 5.01, N: 10.02.

EXAMPLE 60

N-(3-Trifluoromethylphenyl)-N-methyl-N'-(2,5-dichlorophenyl)guanidine hydrochloride (Formula I: hydrochloride salt of R=3-trifluoromethylphenyl, $R^1=CH_3$, $R^2=H$, $R^3=R^4=Cl$, n=0).

TLC: $R_f$=0.3 (10% MeOH/CH$_2$Cl$_2$); MP: 209–210° C.; $^1$H NMR: δ (ppm) 7.86–7.39 (m, 7H, Ar—H); 3.54 (s, 3H, CH$_3$); MS (EI): m/e 361 (M$^+$ for the free base); Anal. (C$_{15}$H$_{12}$Cl$_2$F$_3$N$_3$.HCl); Calcd. (%): C: 45.19, H: 3.29; N: 10.54; Found (%): C: 45.31, H: 3.50, N: 10.61.

EXAMPLE 61

N-(3-Trifluoromethylphenyl)-N-methyl-N'-(2,5-dibromophenyl)guanidine hydrochloride (Formula I: hydrochloride salt of R=3-trifluoromethylphenyl, $R^1=CH_3$, $R^2=H$, $R^3=R^4=Br$, n=0).

TLC: $R_f$=0.5 (10% MeOH/CH$_2$Cl$_2$); MP: 233–234° C.; $^1$H NMR: δ (ppm) 7.90–7.45 (m, 7H, Ar—H); 3.54 (s, 3H, CH$_3$); MS (EI): m/e 449 (M$^+$ for the free base); Anal. (C$_{15}$H$_{12}$Br$_2$F$_3$N$_3$.HCl); Calcd. (%): C: 36.93, H: 2.69, N: 8.62; Found (%): C: 37.00, H: 2.70, N: 8.56.

EXAMPLE 62

N-(3-Trifluoromethylphenyl)-N-methyl-N'-(2-chloro-5-methylthiophenyl)guanidine hydrochloride (Formula I: hydrochloride salt of R=3-trifluoromethylphenyl, $R^1=CH_3$, $R^2=H$, $R^3=Cl$, $R^4=SCH_3$, n=0).

TLC: $R_f$=0.3 (10% MeOH/CH$_2$Cl$_2$); MP: 156–157° C.; $^1$H NMR (300 MHz, CD$_3$OD): δ (ppm) 7.90–7.20 (m, 7H, Ar—H), 3.53 (s, 3H, CH$_3$), 2.49 (s, 3H, SCH$_3$); MS (EI): m/e 373 (M$^+$ for the free base); Anal. (C$_{16}$H$_{15}$ClF$_3$N$_3$S$_2$.HCl); Calcd. (%): C: 46.84, H: 3.93, N: 10.24; Found (%): C: 46.78, H: 4.07, N: 10.12.

EXAMPLE 63

N-(3-Trifluoromethylphenyl)-N-methyl-N'-(2-chloro-5-ethylphenyl)guanidine hydrochloride (Formula I: hydrochloride salt of R=3-trifluoromethylphenyl, $R^1=CH_3$, $R^2=H$, $R^3=Cl$, $R^4=CH_2CH_3$, n=0).

TLC: $R_f$=0.3 (10% MeOH/CH$_2$Cl$_2$); MP: 164–165° C.; $^1$H NMR (300 MHz, CD$_3$OD): δ (ppm) 7.83–7.19 (m, 7H, Ar—H), 3.53 (s, 3H, CH$_3$), 2.65 (q, J=7.5 Hz, 2H, CH$_2$), 1.22 (t, J=7.5 Hz, 3H, CH$_3$); MS (EI): m/e 355 (M$^+$ for the free base); Anal. (C$_{17}$H$_{17}$ClF$_3$N$_3$.HCl); Calcd. (%): C: 52.06, H: 4.63, N: 10.71; Found (%): C: 52.14, H: 4.79, N: 10.66.

EXAMPLE 64

N-(3-Trifluoromethylphenyl)-N-methyl-N'-(2-bromo-5-methylthiophenyl)guanidine hydrochloride (Formula I: hydrochloride salt of R=3-trifluoromethylphenyl, $R^1=CH_3$, $R^2=H$, $R^3=Br$, $R^4=SCH_3$, n=0).

TLC: $R_f$=0.5 (10% MeOH/CH$_2$Cl$_2$); MP: 121–122° C.; $^1$H NMR (300 MHz, CD$_3$OD): δ (ppm) 7.87–7.15 (m, 7H, Ar—H), 3.53 (s, 3H, CH$_3$), 2.49 (s, 3H, CH$_3$); MS (EI): m/e 419 (M$^+$ for the free base); Anal. (C$_{16}$H$_{15}$BrF$_3$N$_3$S.HCl); Calcd. (%): C: 42.26, H: 3.5, N: 9.24; Found (%): C: 42.27, H: 3.70, N: 9.06.

EXAMPLE 65

N-(3-Trifluoromethylphenyl)-N-methyl-N'-(2-bromo-5-ethylphenyl)guanidine hydrochloride (Formula I: hydrochloride salt of R=3-trifluoromethylphenyl, $R^1=CH_3$, $R^2=H$, $R^3=Br$, $R^4=CH_2CH_3$, n=0).

TLC: $R_f$=0.5 (10% MeOH/CH$_2$Cl$_2$); MP: 95–96° C.; $^1$H NMR (300 MHz, CD$_3$OD): δ (ppm) 7.70–6.75 (m, 7H, Ar—H), 3.47 (s, 3H, CH$_3$), 2.58 (q, J=7.5 HZ, 2H, CH$_2$), 1.22 (t, J=7.5 Hz, 3H, CH$_3$); MS (EI): m/e 401 (M$^+$ for the free base); Anal. (C$_{17}$H$_{17}$BrF$_3$N$_3$.HCl); Calcd. (%): C: 46.76, H: 4.15, N: 9.62; Found (%): C: 46.57, H: 4.43, N: 9.38.

EXAMPLE 66

N-(3-Bromophenyl)-N-methyl-N'-(2-chloro-5-methylthiophenyl)guanidine hydrochloride (Formula I: hydrochloride salt of R=3-bromophenyl, $R^1=CH_3$, $R^2=H$, $R^3=Cl$, $R^4=SCH_3$, n=0).

TLC: $R_f$=0.5 (10% MeOH/CH$_2$Cl$_2$); MP: 244–245° C.; $^1$H NMR (300 MHz, CD$_3$OD): δ (ppm) 7.80–7.20 (m, 7H, Ar—H), 3.53 (s, 3H, CH$_3$), 2.49 (s, 3H, SCH$_3$); MS (EI): m/e 385 (M$^+$ for the free base); Anal. (C$_{15}$H$_{15}$BrClN$_3$S.HCl); Calcd. (%): C: 42.78, H: 3.83, N: 9.98; Found (%): C: 42.85, H: 3.99, N: 9.80.

EXAMPLE 67

N-(3-Trifluoromethoxyphenyl)-N'-(2-bromo-5-ethylphenyl)-N-methylguanidine hydrochloride (Formula I: hydrochloride salt of R=3-trifluoromethoxyphenyl, $R^1=CH_3$, $R^2=H$, $R^3=Br$, $R^4=CH_2CH_3$, n=0).

TLC: $R_f$=0.36 (SiO$_2$, CH$_2$Cl$_2$/MeOH=10/1); MP: 74–75° C.; $^1$H NMR (CD$_3$OD): δ (ppm) 7.63–7.15 (m, Ar—H, 7H), 3.30 (s, CH$_3$, 3H), 2.64 (m, CH$_2$, 2H), 1.23 (t, CH$_3$, J=7.45 Hz, 3H); MS (EI): m/e 416.0 (M$^+$: C$_{17}$H$_{17}$N$_3$BrOF$_3$); Anal. (C$_{17}$H$_{17}$N$_3$BrOF$_3$.HCl); Calcd. (%): C: 45.10, H: 4.01, N: 9.28; Found (%): C: 45.31, H: 4.15, N: 9.09.

EXAMPLE 68

N-(3-Trifluoromethoxyphenyl)-N'-(2,5-dibromophenyl)-N-methylguanidine hydrochloride (Formula I: hydrochloride salt of R=3-trifluoromethoxyphenyl, $R^1$=$CH_3$, $R^2$=H, $R^3$=$R^4$=Br, n=0).

TLC: $R_f$=0.55 ($SiO_2$, $CH_2Cl_2$/MeOH=10/1); MP: 188–189° C.; $^1$H NMR ($CD_3OD$): δ (ppm) 7.80–7.40 (m, Ar—H, 7H), 3.52 (s, $CH_3$, 3H); MS (EI): m/e 467.80 ($M^+$: $C_{15}H_{12}N_3Br_2OF_3$); Anal. ($C_{15}H_{12}N_3Br_2OF_3$.HCl); Calcd. (%): C: 35.78, H: 2.60, N: 8.34; Found (%): C: 35.72, H: 2.75, N: 8.26.

EXAMPLE 69

N-(3-Methylsulfonylphenyl)-N-methyl-N'-(2,5-dibromophenyl)guanidine hydrochloride (Formula II: hydrochloride salt of R=3-methylsulfonylphenyl, $R^1$=$CH_3$, $R^2$=H, $R^3$=$R^4$=Br, n=0).

TLC: $R_f$=0.47 ($SiO_2$, $CH_2Cl_2$/MeOH=10/1); MP: 245–246° C.; $^1$H NMR ($CD_3OD$): δ (ppm) 8.15–7.45 (m, Ar—H, 7H), 3.56 (s, $CH_3$, 3H), 3.17 (s, $CH_3$, 3H); MS (EI): m/e 462 ($M^+$: $C_{15}H_{15}N_3Br_2SO_2$); Anal. ($C_{15}H_{15}N_3Br_2So_2$.HCl); Calcd. (%): C: 36.20, H: 3.24, N: 8.44; found (%): C: 35.98, H: 3.11, N: 8.36.

EXAMPLE 70

N-(3-Methylsulfinylphenyl)-N-methyl-N'-(2,5-dibromophenyl)guanidine hydrochloride (Formula II: hydrochloride salt of R=3-methylsulfinylphenyl, $R^1$=$CH_3$, $R^2$=H, $R^3$=$R^4$=Br, n=0).

TLC: $R_f$=0.52 ($SiO_2$, $CH_2Cl_2$/MeOH=10/1); MP: 169–170° C.; $^1$H NMR ($CD_3OD$): δ (ppm) 7.90–7.45 (m, Ar—H, 7H), 3.55 (s, $CH_3$, 3H), 2.85 (s, $CH_3$, 3H); MS (EI): m/e 446 ($M^+$: $C_{15}H_{15}N_3Br_2SO$); Anal. ($C_{15}H_{15}N_3Br_2SO$.HCl); Calcd. (%): C: 37.41, H: 3.35, N: 8.72; Found (%): C: 37.15, H: 3.46, N: 8.38.

EXAMPLE 71

N-(3-Iodophenyl)-N-methyl-N'-(2-chloro-5-methylthiophenyl)guanidine hydrochloride (Formula I: hydrochloride salt of R=iodophenyl, $R^1$=$CH_3$, $R_2$=H, $R^3$=Cl, $R^4$=$SCH_3$, n=0). M.P.: 61–63° C.

EXAMPLE 72

N-(2-Chloro-5-ethylphenyl)-N'-(3-iodophenyl)guanidine hydrochloride (Formula I: hydrochloride salt of R=3-iodophenyl, $R^1$=$R^2$=H, $R^3$=Cl, $R^4$=$CH_2CH_3$, n=0).

white solid; mp 76–77° C.; $R_f$=0.28 (10:1 $CHCl_3$/MeOH): $^1$H NMR (300 MHz, $CD_3OD$): δ (ppm) 7.76–7.78 (m, 1H, Ar—H), 7.52–7.56 (m, 1H, Ar—H), 7.39–7.42 (d, J=6 Hz, 1H, Ar—H), 7.31–7.36 (m, 1H, Ar—H), 7.08–7.22 (m, 3H, Ar—H), 3.30 (q, 2H, $CH_2$), 1.20–1.30 lt, 3H, $CH_3$); MS(EI): m/e 400 ($M^+$ for free base); Anal.: ($C_{15}H_{16}Cl_2IN_3$.HCl); Calcd. (%): C: 41.31, H: 3.70, N: 9.63; Found (%): c: 44.60, H: 3.96, N: 9.59.

EXAMPLE 73

N-(2-chloro-5-thiomethylphenyl)-N'-(3-iodophenyl)-N'-methylguanidine hydrochloride (Formula I: hydrochloride salt of R=3-iodophenyl, $R^1$=$CH_3$, $R^2$=H, $R^3$=Cl, $R^4$=$SCH_3$, n=0).

brown solid; mp 61–63° C.; $R_f$=0.24 (10:1) $CHCl_3$/MeOH); $^1$H NMR (300 MHz, $CD_3OD$): δ 7.74–7.75 (3, 1H, Ar—H), 7.58–7.62 (dt, 1H, Ar—H), 7.30–7.37 (m, 2H, Ar—H), 7.14–7.19 (t, 1H, Ar—H), 6.92–6.97 (m, 2H, Ar—H), 3.36 (s, 3H, N—$CH_3$), 2.46 (s, 3H, SCH3); MS (EI): m/e 432 ($M^+$ for free base); Anal. ($C_{15}H_{15}ClN_3S$.HCl.$Et_2O$); Calcd. (%): C: 40.76, H: 4.33, N: 8.20; Found (%): C: 44.37, H: 4.69, N: 8.58.

EXAMPLE 74

PCP Radioligand Binding Assays

PCP receptor binding assays were performed using rat brain membranes as the source of receptors. The radioligand used to label PCP receptors was [$^3$H]MK-801.

Synthesis of [$^3$H]MK-801 and PCP receptor binding assay protocols are described in J. F. W. Keana, et al., *Life Sci.*, 43:965–973 (1988). Briefly, in the protocols, rat brain membranes were prepared and used as described for "detergent-treated membranes" (see D. E. Murphy, et al., *J. Pharmacol. Exp. Ther.*, 240:778–784 (1987)), and stored at a protein concentration of 10 mg/ml at −70° C. No effect of storage (1 month) of the membranes at −70° C. on receptor number or affinity for [$^3$H]MK-801 was observed.

For assays with rat membranes, the thawed membranes were incubated at 1 mg/ml with 0.01% Triton X-100 for 15 minutes at 32° C., then washed three times by centrifugation to reduce the endogenous amino acid concentrations, and finally resuspended in buffer for assay. Glycine and 1-glutamate were each added back to a final concentration of 1 μM to maximally stimulate the [$^3$H]MK-801 binding. The assays contain 400 μl of membranes, and 50 μl of buffer or unlabelled drug.

For [$^3$H]MK-801 binding, 1 nm radioligand was incubated with 200 μg/ml of rat brain membranes for 4 hours at room temperature. All assays were stopped by rapid filtration under vacuum through Whatman GF/B glass fiber filters presoaked in 0.05% polyethyleneimine using a Brandel 48-well cell harvester (Brandel, Gaithersburg, Md.). The filters were washed three times with 5 ml of cold 5 mM tris-HCl, pH=7.4. Each filter was suspended in 10 ml of Cytoscint (ICN Biomedicals, Costa Mesa, Calif.) and radioactivity was measured by liquid scintillation spectrometry at a counting efficiency of 50%. Nonspecific binding was defined as that remaining in the presence of 10 μM MK-801 or 100 μM PCP.

Saturation data were evaluated and $IC_{50}$ values were determined as described by J. B. Fischer and A. Schonbrunn (*J. Biol. Chem.*, 263:2808–2816 (1988)). $K_i$ values are derived from the $IC_{50}$ values as described by Cheng et al., *Biochem. Pharmacol.*, 22:3099–3108 (1973).

Results of the assay are shown in Table I which follows Example 75 below, wherein the general formula of the tested compounds (i.e., compounds identified as compound nos. 1–83) is shown at the top of Table I with the particular substituent groups of each compound specified within the Table.

EXAMPLE 75

Sigma Receptor Binding Assay

Methods.

Sigma receptor binding assays using guinea pig brain membrane homogenates and the radioligand [$^3$H]DTG were conducted as described by E. Weber, et al., *P.N.A.S.* (*USA*), 83:8784–8788 (1986). Briefly, frozen whole guinea-pig brains (Biotrol, Indianapolis, Ind.) were homogenized in 10 volumes (w/v) of ice-cold 320 mM sucrose using a Brinkman polytron. The homogenate was centrifuged at 1,000×g for 20 minutes at 4° C. The supernatant was centrifuged at 20,000×g for 20 minutes at 4° C. The resulting pellet was resuspended in 10 initial volumes of 50 mM Tris/HCl buffer at pH 7.4 and centrifuged at 20,000×g for 20 minutes at 4° C. The resulting pellet was resuspended in 5 initial volumes ice-cold 50 mM Tris/HCl (pH 7.4), and the final volume was adjusted to yield a protein concentration of 3 mg/ml. Aliquots of 20-ml were stored at −70° C. until used, with no detectable loss of binding.

For [$^3$H]DTG binding assays, the frozen membrane suspensions were thawed and diluted 1:3 in 50 mM Tris/HCl (pH 7.4). To 12×75 mm polystyrene test tubes were added 0.8 ml of diluted membrane suspension, 0.1 ml of [$^3$H]DTG (Dupont/NEN) to yield a final concentration of 1.4 nM, and 0.1 ml of unlabelled drugs or buffer. The protein concentration in the 1-ml final incubation volume was 800 μg/ml, corresponding to 32 mg of brain tissue (original wet weight) and to a tissue concentration within the linear range for specific binding. Non-specific binding was defined as that remaining in the presence of 10 μM haloperidol. Incubations were terminated after 90 minutes at room temperature by addition of 4 ml of ice-cold 50 mM Tris/HCl (pH 7.4) and rapid filtration of the membrane suspension through Whatman GF/B glass-fiber filters under vacuum, using a 48-well cell harvester (Brandel). The filters were washed 2 times with 4 ml of 50 mM Tris/HCl (pH 7.4). Each filter was suspended in 10 ml Cytoscint (ICI), and radioactivity was measured by liquid scintillation spectrometry at a counting efficiency of approximately 50%. IC$_{50}$ values were determined by non-linear regression analysis. The results are shown in Table I below for each of the tested compounds of the specified structure. In Table I, the designation "NT" indicates the compound was not tested in the specified assay.

TABLE I

| | | | | | | [$^3$H-MK801] | | [$^3$H-DTG] |
|---|---|---|---|---|---|---|---|---|
| Compd. No. | R | R$^1$ | R$^2$ | R$^3$ | R$^4$ | IC$_{50}$ (nM) | K$_i$ (nM) | IC$_{50}$ (nM) |
| 1 | 3-ethylphenyl | H | H | Cl | Cl | 88 | 67.7 | 11.8 |
| 2 | 3-ethylphenyl | H | H | Br | Br | 87.5 | 67.3 | 18.2 |
| 3 | 3-ethylphenyl | H | H | H | Cl | 146 | 112 | 15.5 |
| 4 | 3-ethylphenyl | H | H | Br | CF$_3$ | 86.9 | 66.8 | 10.3 |
| 5 | 3-ethylphenyl | H | H | F | CF$_3$ | 98.9 | 76.0 | 14.8 |
| 6 | 3-ethylphenyl | H | H | Cl | CF$_3$ | 57.1 | 43.9 | 14.2 |
| 7 | 3-ethylphenyl | H | H | Cl | CH$_3$ | 100 | 76.9 | 30.6 |
| 8 | 3-ethylphenyl | H | H | Cl | CH$_2$CH$_3$ | 45.2 | 34.7 | 2.04 |
| 9 | 3-ethylphenyl | H | H | H | CH$_2$CH$_3$ | 168 | 129 | 8.0 |
| 10 | 3-ethylphenyl | CH$_3$ | H | Cl | Cl | 84.6 | 65.0 | 28.5 |
| 11 | 3-ethylphenyl | CH$_3$ | H | Br | Br | 47.6 | 36.6 | 40.2 |
| 12 | 3-ethylphenyl | CH$_3$ | H | H | Cl | 646 | 497 | 43.5 |
| 13 | 3-ethylphenyl | CH$_3$ | H | Br | CF$_3$ | 102 | 78.4 | 208 |
| 14 | 3-ethylphenyl | CH$_3$ | H | F | CF$_3$ | 252 | 194 | 85 |
| 15 | 3-ethylphenyl | CH$_3$ | H | Cl | CF$_3$ | 131 | 101 | 120 |
| 16 | 3-ethylphenyl | CH$_3$ | H | Cl | CH$_3$ | 101 | 77.6 | 45.3 |
| 17 | 3-ethylphenyl | CH$_3$ | H | Cl | CH$_2$CH$_3$ | 53 | 40.7 | 115 |
| 18 | 3-ethylphenyl | CH$_3$ | H | H | CH$_2$CH$_3$ | 213 | 164 | 81.8 |
| 19 | 3-ethylphenyl | CH$_3$ | H | H | Br | 105 | 80.7 | 40 |
| 20 | 3-ethylphenyl | CH$_3$ | H | F | CH$_2$CH$_3$ | 126 | 96.9 | 112.5 |
| 21 | 3-ethylphenyl | H | H | F | CH$_2$CH$_3$ | 64.8 | 49.8 | 7.4 |
| 22 | 3-ethylphenyl | CH$_3$ | H | Br | CH$_2$CH$_3$ | 16.7 | 12.8 | 203 |
| 23 | 3-ethylphenyl | H | H | Br | CH$_2$CH$_3$ | 38.3 | 24.9 | 5.07 |
| 24 | 3-ethylphenyl | CH$_3$ | H | Cl | SCH$_3$ | 6.7 | 5.1 | 309.5 |
| 25 | 3-ethylphenyl | H | H | Cl | SCH$_3$ | 15.4 | 11.8 | 15.8 |
| 26 | 3-ethylphenyl | CH$_3$ | CH$_3$ | Cl | Cl | 93.7 | 72.0 | 39.3 |
| 27 | 3-ethylphenyl | CH$_3$ | CH$_3$ | Br | Br | 35.5 | 27.3 | 380 |
| 28 | 3-ethylphenyl | CH$_3$ | CH$_3$ | Cl | CH$_2$CH$_3$ | 145 | 112 | 240.5 |
| 29 | 2-chloro-5-ethylphenyl | H | H | Cl | CH$_3$ | 54.7 | 42.1 | 36.1 |
| 30 | 2-chloro-5-ethylphenyl | H | H | Br | Br | 66.4 | 51.0 | 186 |
| 31 | 1-naphthyl | H | H | Cl | Cl | 41 | 31.5 | 25 |
| 32 | 1-naphthyl | H | H | Br | Br | 48.6 | 37.3 | 37.6 |
| 33 | 1-naphthyl | H | H | CH$_3$ | CH$_3$ | 79.2 | 60.9 | 27.4 |
| 34 | 1-naphthyl | H | H | F | CH$_3$ | 86 | 66.1 | 69 |
| 35 | 1-naphthyl | H | H | Cl | CH$_3$ | 31.2 | 24.0 | 43 |
| 36 | 1-naphthyl | H | H | OCH$_3$ | CH$_3$ | 61.5 | 47.3 | 161 |
| 37 | 1-naphthyl | H | H | H | Cl | 371 | 285 | 33 |
| 38 | 1-naphthyl | H | H | H | CH$_3$ | 192 | 148 | 75 |
| 39 | 1-naphthyl | H | H | F | CF$_3$ | 38.4 | 29.5 | 79.4 |
| 40 | 1-naphthyl | H | H | Cl | CF$_3$ | 38.6 | 29.6 | 52.5 |
| 41 | 1-naphthyl | H | H | Br | CF$_3$ | 51.1 | 39.3 | 49.6 |
| 42 | 1-naphthyl | H | H | SCH$_3$ | CF$_3$ | 170 | 131 | 418 |
| 43 | 1-naphthyl | H | H | H | CF$_3$ | 129 | 99.2 | 238 |
| 44 | 1-naphthyl | H | H | Cl | CH$_2$CH$_2$ | 20.6 | 15.8 | 4.94 |

TABLE I-continued

[Structure: R-N(R¹)-C(=NH)-N(R²)-phenyl with R³ and R⁴ substituents on the phenyl ring]

| Compd. No. | R | R¹ | R² | R³ | R⁴ | [³H-MK801] IC$_{50}$ (nM) | K$_i$ (nM) | [³H-DTG] IC$_{50}$ (nM) |
|---|---|---|---|---|---|---|---|---|
| 45 | 1-naphthyl | H | H | H | CH$_2$CH$_3$ | 39 | 30.0 | 53.8 |
| 46 | 1-naphthyl | H | H | Cl | SCH$_3$ | 43 | 33.2 | 25.4 |
| 47 | 1-naphthyl | H | H | H | SCH$_3$ | 124 | 95.3 | 27 |
| 48 | 8-quinolinyl | H | H | Cl | CH$_3$ | 32 | 24.4 | 989 |
| 49 | 8-quinolinyl | H | H | Cl | CH$_2$CH$_3$ | 4.2 | 3.2 | 322 |
| 50 | 1-naphthyl | H | CH$_3$ | Cl | Cl | 62 | 47.6 | 1318 |
| 51 | 1-naphthyl | H | CH$_3$ | Br | Br | 65 | 49.9 | 1250 |
| 52 | 1-naphthyl | H | CH$_3$ | H | Cl | 107 | 82.3 | 2982 |
| 53 | 1-naphthyl | H | CH$_3$ | H | Br | 54 | 41.6 | 2759 |
| 54 | 1-naphthyl | H | CH$_3$ | CH$_3$ | CH$_3$ | 79 | 60.8 | 1554 |
| 55 | 1-naphthyl | H | CH$_3$ | Cl | CH$_3$ | 41 | 31.6 | 2425 |
| 56 | 1-naphthyl | H | CH$_3$ | H | CH$_3$ | 85 | 65.4 | 1262 |
| 57 | 1-naphthyl | H | CH$_3$ | Cl | CH$_2$CH$_3$ | 32.8 | 25.2 | 136 |
| 58 | 1-naphthyl | H | CH$_3$ | H | CH$_2$CH$_3$ | 37.5 | 28.8 | 2635 |
| 59 | 3-ethylphenyl | CH$_3$ | H | Br | CH$_3$ | 3.19 | 2.45 | 240 |
| 60 | 3-methylthiophenyl | CH$_3$ | H | Cl | SCH$_3$ | 2.43 | 1.84 | 480 |
| 61 | 3-methylthiophenyl | CH$_3$ | H | Cl | CH$_2$CH$_3$ | 12.6 | 9.69 | 178 |
| 62 | 3-methylthiophenyl | CH$_3$ | H | Cl | Cl | 59.3 | 45.6 | 130 |
| 63 | 3-methylthiophenyl | CH$_3$ | H | Br | SCH$_3$ | 2.15 | 1.65 | NT |
| 64 | 3-methylthiophenyl | CH$_3$ | H | Br | CH$_2$CH$_3$ | 5.09 | 3.92 | 180 |
| 65 | 3-methylthiophenyl | CH$_3$ | H | Br | Br | 5.38 | 4.13 | 113 |
| 66 | 3-trifluoromethyl-phenyl | CH$_3$ | H | Cl | SCH$_2$ | 8.47 | 6.92 | 421 |
| 67 | 3-trifluoromethyl-phenyl | CH$_3$ | H | Cl | CH$_2$CH$_3$ | 77.0 | 59.2 | 200 |
| 68 | 3-trifluoromethyl-phenyl | CH$_3$ | H | Cl | Cl | 201 | 155 | 110 |
| 69 | 3-trifluoromethyl-phenyl | CH$_3$ | H | Br | SCH$_3$ | 5.55 | 4.27 | 631 |
| 70 | 3-trifluoromethyl-phenyl | CH$_3$ | H | Br | CH$_2$CH$_3$ | 20.4 | 15.7 | 166 |
| 71 | 3-trifluoromethyl-phenyl | CH$_3$ | H | Br | Br | 34.0 | 26.1 | 224 |
| 72 | 3-bromophenyl | CH$_3$ | H | Cl | SCH$_3$ | 4.65 | 3.58 | NT |
| 73 | 3-trifluoro-methoxyphenyl | CH$_3$ | H | Br | Br | 25.6 | 19.7 | NT |
| 74 | 3-trifluoro-methoxyphenyl | CH$_3$ | H | Br | CH$_2$CH$_3$ | 16.0 | 12.3 | NT |
| 75 | 3-methyl-sulfonylphenyl | CH$_3$ | H | Br | Br | 530 | 408 | NT |
| 76 | 3-methyl-sulfinylphenyl | CH$_3$ | H | Br | Br | 322 | 248 | NT |
| 77 | iodophenyl | CH$_3$ | H | Cl | SCH$_3$ | 2.11 | 1.62 | NT |
| 78 | 3-iodophenyl | H | H | Cl | CH$_2$CH$_3$ | 13.7 | 10.5 | NT |
| 79 | 8-quinolinyl | CH$_3$ | H | Cl | SCH$_3$ | 22.3 | 17 | 542 |

EXAMPLE 76

In vivo assay for protection against NMDA-induced excitotoxic damage to the central nervous system.

The in vivo potency of compounds of the present invention is exemplified by data summarized in Table II and obtained pursuant to the following protocol. Day 7 neonatal rats were anesthetized with metophane inhalation anesthetic for 4–6 minutes, inserted into a stereotaxic apparatus and injected intrastriatally with 0.5 µl of 50 mM NMDA (N-methyl-D-aspartate). 15 minutes after the NMDA injection, the rat pups were injected intraperitoneally with 10, 30 or 60 µmol/kg of the NMDA antagonist of the structure specified in Table II. Animals were returned to their mother and watched for signs of distress (e.g., respiratory depression). After five days, the animals were anesthetized with CO$_2$ and then decapitated; their brains were removed and weighed to determine the degree of neuroprotection. Because NMDA injection results in a retardation of brain growth (including necrosis), effects can be measured gravimetrically in terms of the weights of injected and non-injected hemispheres. Two groups of rat pups were used at each of three doses of a compound to generate a neuroprotection dose-response curve. The chemical structure of each of the tested compounds is specified below with the general formula of the compounds shown at the top of Table II with particular substituent groups specified within that Table. Table II discloses 1) the ED$_{80}$ for each tested compound, i.e., the dose of a compound that provides 80% of the maximum protection against damage to the central nervous system; and 2) the percent (%) maximum protection against damage to the central nervous system provided by the indicated dose expressed as µmol per kilogram bodyweight of the test subject.

TABLE II

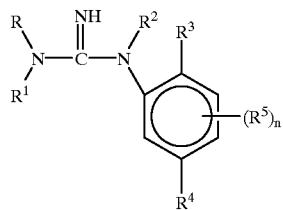

| Cmpd. No. | R | $R_1$ | $R_2$ | $R_3$ | $R_4$ | ED80 µmol/kg | % maximum protection per dose (µmol/kg) |
| --- | --- | --- | --- | --- | --- | --- | --- |
| 1 | 3-ethylphenyl | $CH_3$ | H | Cl | Cl | 36.4 | 88.8 @ 60 |
| 2 | 3-ethylphenyl | $CH_3$ | H | Br | Br | 13.4 | 93.8 @ 60 |
| 3 | 3-ethylphenyl | H | H | F | $CF_3$ | 15.2 | 76.6 @ 60 |
| 4 | 3-ethylphenyl | $CH_3$ | H | Cl | $C_2H_5$ | 19.8 | 77.8 @ 60 |
| 5 | 1-naphthyl | H | $CH_3$ | Cl | $C_2H_5$ | 22.3 | 92.2 @ 60 |
| 6 | 1-naphthyl | H | $CH_3$ | Br | Br | 26.9 | 85.7 @ 60 |
| 7 | 1-naphthyl | H | $CH_3$ | $CH_3$ | $CH_3$ | 22.5 | 86.0 @ 30 |
| 8 | 1-naphthyl | H | H | F | $CF_3$ | 28.8 | 96.0 @ 60 |
| 9 | 1-naphthyl | H | H | Cl | $SCH_3$ | 10.8 | 92.7 @ 60 |
| 10 | 1-naphthyl | H | H | Cl | $CH_3$ | 45.8 | 96.4 @ 60 |
| 11 | 8-quinolyl | H | H | Cl | $C_2H_5$ | 14.2 | 94.5 @ 30 |

This invention has been described in detail with reference to preferred embodiments thereof. However, it will be appreciated that those skilled in the art, upon consideration of this disclosure, may make modifications and improvements within the spirit and scope of the invention.

What is claimed is:

1. A method of inhibiting NMDA receptor-ion channel related neurotoxicity or susceptible thereto in a mammal exhibiting such neurotoxicity comprising administering to the mammal an effective amount of a compound of the following formula I:

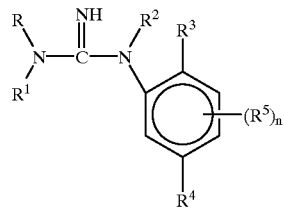

wherein R is substituted or unsubstituted carbocyclic aryl, substituted or unsubstituted aralkyl, or a substituted or unsubstituted heteroaromatic or heterocyclic group having 1 to 3 rings, 3 to 8 ring members in each ring and 1 to 3 heteroatoms;

$R^1$ and $R^2$ are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted carbocyclic aryl, substituted or unsubstituted aralkyl, or a substituted or unsubstituted heteroaromatic or heteroalicyclic group having 1 to 3 rings, 3 to 8 ring members in each ring and 1 to 3 hetero atoms;

$R^3$, $R^4$, and each $R^5$ substituent are each independently halogen, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted carbocyclic aryl, or substituted or unsubstituted aralkyl; n is an integer of from 0–3; or a pharmaceutically acceptable salt thereof, with the exclusion of N-(2,4-di-iodo-5-hydroxyphenyl)-N'-(2-tolyl)-guanidine and N-(2-methoxy-5-ethylphenyl)-N'-naphthylguanidine.

2. The method of claim 1 wherein said neurotoxicity is caused by excessive release of endogenous glutamate following the occurrence of hypoxia, hypoglycemia, brain or spinal chord ischemia, or brain or spinal chord trauma.

3. A method of treating nerve cell death, stroke, heart attack, brain or spinal cord trauma, brain or spinal cord ischemia or heart attack comprising administering to a mammal in need of such treatment an effective amount of a compound of the following formula I:

wherein R is substituted or unsubstituted carbocyclic aryl, substituted or unsubstituted aralkyl, or a substituted or unsubstituted heteroaromatic or heterocyclic group having 1 to 3 rings, 3 to 8 ring members in each ring and 1 to 3 heteroatoms;

$R^1$ and $R^2$ are each independently hydrogen, substituted or unsubstituted alkyl, substituted or unsubstituted alkenyl, substituted or unsubstituted alkynyl, substituted or unsubsuituted alkoxy, substituted or unsubstituted alkylthio, substituted or unsubstituted aminoalkyl, substituted or unsubstituted carbocyclic aryl, substituted or unsubstituted aralkyl, or a substituted or unsubstituted heteroaromatic or heteroalicyclic group having 1 to 3 rings, 3 to 8 ring members in each ring and 1 to 3 hetero atoms;

$R^3$, $R^4$, and each $R^5$ substituent are each independently halogen, azido, substituted or unsubstituted alkyl, substituted or unsubstituted alkenyl, substituted or unsubstituted alkyl, substituted or unsubstituted alkoxy, substituted or unsubstituted alkyithio, substituted or unsubstituted aminoalkyl, substituted or unsubstituted carbocyclic aryl, or substituted or unsubstituted aralkyl; n is an integer of from 0–3; or a pharmaceutically acceptable salt thereof, with the exclusion of N-(2,4-di-iodo-5-hydroxyphenyl)-N'-(2-tolyl)-guanidine and N-(2-methoxy-5-ethylphenyl)-N'-naphthylguanidine.

4. A method of inhibiting NMDA receptor-ion channel related neurotoxicity or susceptible thereto in a mammal exhibiting such neurotoxicity comprising administering to the mammal an effective amount of a compound of the following formula II:

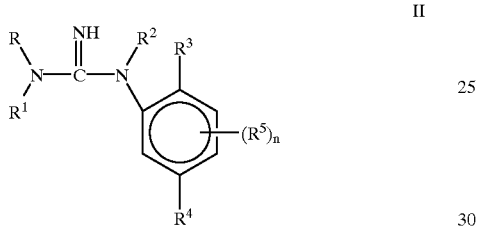

II wherein R is substituted or unsubstituted carbocyclic aryl, substituted or unsubstituted aralkyl, or a substituted or unsubstituted heteroaromatic or heterocyclic group having 1 to 3 rings, 3 to 8 ring members in each ring and 1 to 3 heteroatoms;

$R^1$ and $R^2$ are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, substituted or unsubstituted aralkyl, or a substituted or unsubstituted heteroaromatic or heteroalicyclic group having 1 to 3 rings, 3 to 8 ring members in each ring and 1 to 3 hetero atoms;

$R^3$, $R^4$, and each $R^5$ substituent are each independently halogen, hydroxyl, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, or substituted or unsubstituted aralkyl; and with at least one of R, $R^1$, $R^2$, $R^3$, $R^4$ and $R^5$ being alkylsulfinyl or alkylsulfonyl; n is an integer of from 0–3; or a pharmaceutically acceptable salt thereof.

5. A method of treating nerve cell death, stroke, heart attack, brain or spinal cord trauma, brain or spinal cord ischemia or heart attack comprising administering to a mammal in need of such treatment an effective amount of a compound of the following formula II:

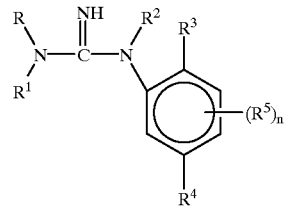

II wherein R is substituted or unsubstituted carbocyclic aryl, substituted or unsubstituted aralkyl, or a substituted or unsubstituted heteroaromatic or heterocyclic group having 1 to 3 rings, 3 to 8 ring members in each ring and 1 to 3 heteroatoms;

$R^1$ and $R^2$ are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted allylsulfinyl, substituted or unsubstituted alkylsulfonyl, substituted or unsubstituted aminoalkyl, substituted or unsubstituted carbocyclic aryl, substituted or unsubstituted aralkyl, or a substituted or unsubstituted heteroaromatic or heteroalicyclic group having 1 to 3 rings, 3 to 8 ring members in each ring and 1 to 3 hetero atoms;

$R^3$, $R^4$, and each $R^5$ substituent are each independently halogen, hydroxyl, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, or substituted or unsubstituted aralkyl; and with at least one of R, $R^1$, $R^2$, $R^3$, $R^4$ and $R^5$ being alkylsulfinyl or alkylsulfonyl; n is an integer of from 0–3; or a pharmaceutically acceptable salt thereof.

6. A method of claim claim 3 wherein the mammal is suffering from stroke.

7. A method of claim 3 wherein the mammal is suffering from brain or spinal cord trauma or brain or spinal cord ischemia.

8. A method of claim 3 wherein the mammal is suffering from heart attack.

9. A method of treating a mammal suffering from nerve cell degeneration resulting from hypoxia, hypoglycemia, brain or spinal cord ischemia or brain or spinal cord trauma, comprising administering to the mammal an effective amount of a compound of the following formula I:

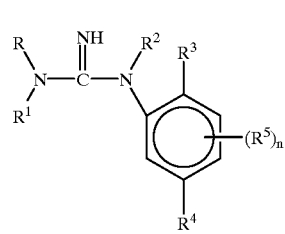

I wherein R is substituted or unsubstituted carbocyclic aryl, substituted or unsubstituted aralkyl, or a substituted or unsubstituted heteroaromatic or heterocyclic group having 1 to 3 rings, 3 to 8 ring members in each ring and 1 to 3 heteroatoms;

R¹ and R² are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted carbocyclic aryl, substituted or unsubstituted aralkyl, or a substituted or unsubstituted heteroaromatic or heteroalicyclic group having 1 to 3 rings, 3 to 8 ring members in each ring and 1 to 3 hetero atoms;

R³, R⁴, and each R⁵ substituent are each independently halogen, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted carbocyclic aryl, or substituted or unsubstituted aralkyl; n is an integer of from 0–3; or a pharmaceutically acceptable salt thereof, with the exclusion of N-(2,4-di-iodo-5-hydroxyphenyl)-N'-(2-tolyl)-guanidine and N-(2-methoxy-5-ethylphenyl)-N'-naphthylguanidine.

10. A method of treating a mammal undergoing surgery where neurological deficit is a potential complication, comprising administering to the mammal a treatment effective amount of the following formula I:

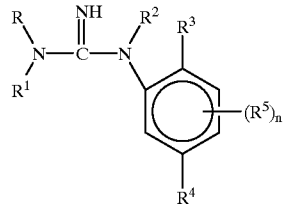

wherein R is substituted or unsubstituted carbocyclic aryl, substituted or unsubstituted aralkyl, or a substituted or unsubstituted heteroaromatic or heterocyclic group having 1 to 3 rings, to 3 to 8 ring members in each ring and 1 to 3 heteroatoms;

R¹ and R² are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted carbocyclic aryl, substituted or unsubstituted aralkyl, or a substituted or unsubstituted heteroaromatic or heteroalicyclic group having 1 to 3 rings, 3 to 8 ring members in each ring and 1 to 3 hetero atoms;

R³, R⁴, and each R⁵ substituent are each independently halogen, hydroxyl, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted carbocyclic aryl, or substituted or unsubstituted aralkyl; n is an integer of from 0–3; or a pharrnaccutically acceptable salt thereof, with the exclusion of N-(2,4-di-iodo-5-hydroxphenyl)-N'-(2-tolyl)-guanidine and N-(2-methoxy-5-ethylphenyl)-N'-naphthylguanidine.

11. The method of any one of claims 1, 3, 6, 7, 8 or 9 wherein the compound is N-(3-methylthiophenyl)-N-methyl-N'-(2-chloro-5-methylthiophenyl)guanidine or a pharmaceutically acceptable salt thereof.

12. The method of any one of claims 1, 3, 6, 7, 8 or 9 wherein the compound is N-(3-ethylphenyl)-N-methyl-N'-(2,5-dibromophenyl)guanidine or a pharmaceutically acceptable salt thereof.

13. A method of claim 1 wherein both R and R² are hydrogen.

14. A method of claim 1 wherein at least two of R, R¹ and R² is other than hydrogen.

15. The method of claim 1 or 3 wherein the compound is of the following Formula Ia:

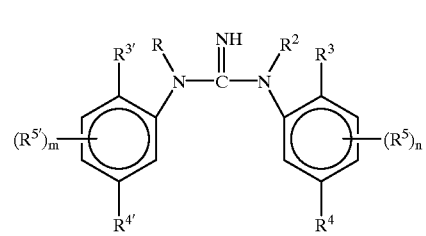

wherein R and R² are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted carbocyclic aryl, substituted or unsubstituted aralkyl, or a substituted or unsubstituted heteroaromatic or heteroalicyclic group having 1 to 3 rings, 3 to 8 ring members in each ring and 1 to 3 hetero atoms;

R³, R⁴, each R⁵, R³', R⁴', and each R⁵' are each independently halogen, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted carbocyclic aryl, or substituted or unsubstituted aralkyl; m and n are each independently an integer of from 0 to 3; or a pharmaceutically acceptable salt thereof.

16. The method of claim 1 or 3 wherein the compound is of the following Formula Ib:

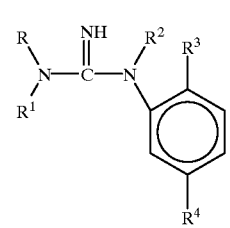

wherein R is substituted or unsubstituted carbocyclic aryl, substituted or unsubstituted aralkyl, or a substituted or unsubstituted heteroaromatic or heterocyclic group having 1 to 3 rings, 3 to 8 ring members in each ring and 1 to 3 heteroatoms;

R¹ and R² are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted carbocyclic aryl, substituted or unsubstituted aralkyl, or a substituted or unsubstituted heteroaromatic or heteroalicyclic group having 1 to 3 rings, 3 to 8 ring members in each ring and 1 to 3 hetero atoms;

$R^3$ and $R^4$ are each independently halogen, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted carbocyclic aryl, or substituted or unsubstituted aralkyl; or a pharmaceutically acceptable salt thereof.

17. The method of any one of claims 1, 3, 6 or 9 wherein the compound is of the following Formula Ic:

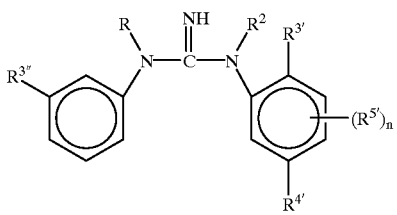

wherein R and $R^2$ are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or unsubstituted carbocyclic aryl, substituted or unsubstituted aralkyl, or a substituted or unsubstituted heteroaromatic or heterocyclic group having 1 to 3 rings, 3 to 8 ring members in each ring and 1 to 3 heteroatoms;

$R^{3'}$, $R^{4'}$, $R^{3''}$ and each $R^{5'}$ substituent are each independently halogen, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted aminoalkyl, substituted or substituted carbocyclic aryl, or substituted or unsubstituted aralkyl; n is an integer of from 0 to 3; or a pharmaceutically acceptable salt thereof.

18. A method of claim 17 wherein both R and $R^2$ are hydrogen.

19. A method of claim 17 wherein at least one of R and $R^2$ is other than hydrogen.

20. A method of claim 19 wherein R and $R^2$ are hydrogen or alkyl having 1 to about 4 carbons.

21. A method of claim 17 wherein R is methyl, ethyl or propyl and $R^2$ is hydrogen.

22. A method of claim 21 where R is methyl.

23. A method of claim 17 wherein $R^{3'}$, $R^{4'}$, $R^{5'}$ and $R^{3''}$ are independently halogen, azido, alkyl, halogenated alkyl, alkoxy, halogenated alkoxy or alkylthio.

24. A method of claim 1 or 3 wherein the compound is:
N-(3-ethylphenyl)-N,N'-dimethyl-N'-(2,5-dichlorophenyl)guanidine;
N-(3-ethylphenyl)-N-methyl-N'-(2,5-dichlorophenyl)guanidine;
N-(3-ethylphenyl)-N'-(2,5-dichlorophenyl)-N'-methylguanidine;
N-(3-ethylphenyl)-N'-(2,5-dichlorophenyl)guanidine;
N-(3-ethylphenyl)-N-methyl-N'-(2,5-dibromophenyl)guanidine;
N-(3-ethylphenyl)-N'-(2,5-dibromophenyl)-N'-methylguanidine;
N-(3-ethylphenyl)-N'-(2,5-dibromophenyl)guanidine;
N-(3-ethylphenyl)-N-methyl-N'-(2-chloro-5-trifluoromethylphenyl)guanidine;
N-(3-ethylphenyl)-N'-(2-chloro-5-trifluoromethylphenyl)guanidine;
N-(3-ethylphenyl)-N,N'-dimethyl-N'-(2-bromo-5-trifluoromethylphenyl)guanidine;
N-(3-ethylphenyl)-N-methyl-N'-(2-bromo-5-trifluoromethylphenyl)guanidine;
N-(3-ethylphenyl)-N'-(2-bromo-5-trifluoromethylphenyl)guanidine;
N-(3-ethylphenyl)-N-methyl-N'-(2-fluoro-5-trifluoromethylphenyl)guanidine;
N-(3-ethylphenyl)-N'-(2-fluoro-5-trifluoromethylphenyl)guanidine;
N-(3-ethylphenyl)-N,N'-dimethyl-N'-(2-chloro-5-ethylphenyl)guanidine;
N-(3-ethylphenyl)-N-methyl-N'-(2-chloro-5-ethylphenyl)guanidine;
N-(3-ethylphenyl)-N'-(2-chloro-5-ethylphenyl)guanidine;
N-(3-ethylphenyl)-N,N'-dimethyl-N'-(2-bromo-5-ethylphenyl)guanidine;
N-(3-ethylphenyl)-N-methyl-N'-(2-bromo-5-ethylphenyl)guanidine;
N-(3-ethylphenyl)-N'-(2-bromo-5-ethylphenyl)guanidine;
N-(3-ethylphenyl)-N,N'-dimethyl-N'-(2-fluoro-5-ethylphenyl)guanidine;
N-(3-ethylphenyl)-N-methyl-N'-(2-fluoro-5-ethylphenyl)guanidine;
N-(3-ethylphenyl)-N'-(2-fluoro-5-ethylphenyl)guanidine;
N-(3-ethylphenyl)-N,N'-dimethyl-N'-(2-chloro-5-methylphenyl)guanidine;
N-(3-ethylphenyl)-N-methyl-N'-(2-chloro-5-methylphenyl)guanidine;
N-(3-ethylphenyl)-N'-(2-chloro-5-ethylphenyl)guanidine;
N-(3-ethylphenyl)-N'-(2-chloro-5-methylphenyl)guanidine;
N-(3-ethylphenyl)-N-methyl-N'-(2-chloro-5-methylthio)guanidine;
N-(3-ethylphenyl)-N'-(2-chloro-5-methylthio)guanidine;
N-(3-ethylphenyl)-N-methyl-N'-(2,4,5-trichlorophenyl)guanidine;
N-(3-ethylphenyl)-N'-(2,4,5-trichlorophenyl)guanidine;
N-(3-ethylphenyl)-N-methyl-N'-(2,3,5-trichlorophenyl)guanidine;
N-(3-ethylphenyl)-N'-(2,3,5-trichlorophenyl)guanidine;
N-(3-methylthiophenyl)-N-methyl-N'-(2-chloro-5-methylthiophenyl)guanidine;
N-(3-methylthiophenyl)-N'-methyl-N'-(2-chloro-5-methylthiophenyl)guanidine;
N-(3-methylthiophenyl)-N'-(2-chloro-5-methylthiophenyl)guanidine;
N-(3-methylthiophenyl)-N-methyl-N'-(2-chloro-5-ethylphenyl)guanidine;
N-(3-methylthiophenyl)-N'-methyl-N'-(2-chloro-5-ethylphenyl)guanidine;
N-(3-methylthiophenyl)-N'-(2-chloro-5-ethylphenyl)guanidine;

N-(3-methylthiophenyl)-N-methyl-N'-(2-bromo-5-ethylphenyl)guanidine;
N-(3-methylthiophenyl)-N'-methyl-N'-(2-bromo-5-ethylphenyl)guanidine;
N-(3-methylthiophenyl)-N'-(2-bromo-5-ethylphenyl)guanidine;
N-(3-methylthiophenyl)-N-methyl-N'-(2,5-dichlorophenyl)guanidine;
N-(3-methylthiophenyl)-N'-methyl-N'-(2,5-dichlorophenyl)guanidine;
N-(3-methylthiophenyl)-N'-(2,5-dichlorophenyl)guanidine;
N-(3-methylthiophenyl)-N-methyl-N'-(2,5-dibromophenyl)guanidine;
N-(3-methylthiophenyl)-N'-methyl-N'-(2,5-dibromophenyl)guanidine;
N-(3-methylthiophenyl)-N'-(2,5-dibromophenyl)guanidine;
N-(3-trifluoromethylphenyl)-N-methyl-N'-(2-chloro-5-methylthiophenyl)guanidine;
N-(3-trifluoromethylphenyl)-N'-methyl-N'-(2-chloro-5-methylthiophenyl)guanidine;
N-(3-trifluoromethylphenyl)-N'-(2-chloro-5-methylthiophenyl)guanidine;
N-(3-trifluoromethylphenyl)-N-methyl-N'-(2-chloro-5-ethylphenyl)guanidine;
N-(3-trifluoromethylphenyl)-N'-methyl-N'-(2-chloro-5-ethylphenyl)guanidine;
N-(3-trifluoromethylphenyl)-N'-(2-chloro-5-ethylphenyl)guanidine;
N-(3-trifluoromethylphenyl)-N-methyl-N'-(2-bromo-5-ethylphenyl)guanidine;
N-(3-trifluoromethylphenyl)-N'-methyl-N'-(2-bromo-5-ethylphenyl)guanidine;
N-(3-trifluoromethylphenyl)-N'-(2-bromo-5-ethylphenyl)guanidine;
N-(3-trifluoromethylphenyl)-N-methyl-N'-(2,5-dichlorophenyl)guanidine;
N-(3-trifluoromethylphenyl)-N'-methyl-N'-(2,5-dichlorophenyl)guanidine;
N-(3-trifluoromethylphenyl)-N'-(2,5-dichlorophenyl)guanidine;
N-(3-trifluoromethylphenyl)-N-methyl-N'-(2,5-dibromophenyl)guanidine;
N-(3-trifluoromethylphenyl)-N'-methyl-N'-(2,5-dibromophenyl)guanidine;
N-(3-trifluoromethylphenyl)-N'-(2,5-dibromophenyl)guanidine;
N-(3-ethylphenyl)-N-methyl-N'-(2-bromo-5-methylthiophenyl)guanidine;
N-(3-ethylphenyl)-N'-methyl-N'-(2-bromo-5-methylthiophenyl)guanidine;
N-(3-ethylphenyl)-N'-(2-bromo-5-methylthiophenyl)guanidine;
N-(3-methylthiophenyl)-N-methyl-N'-(2-bromo-5-methylthiophenyl)guanidine;
N-(3-methylthiophenyl)-N'-methyl-N'-(2-bromo-5-methylthiophenyl)guanidine;
N-(3-methylthiophenyl)-N'-(2-bromo-5-methylthiophenyl)guanidine;
N-(3-methylthiophenyl)-N-methyl-N'-(2-bromo-5-ethylphenyl)guanidine;
N-(3-methylthiophenyl)-N'-methyl-N'-(2-bromo-5-ethylphenyl)guanidine;
N-(3-methylthiophenyl)-N'-(2-bromo-5-ethylphenyl)guanidine;
N-(3-trifluoromethylphenyl)-N-methyl-N'-(2-bromo-5-methylthiophenyl)guanidine;
N-(3-trifluoromethylphenyl)-N'-methyl-N'-(2-bromo-5-methylthiophenyl)guanidine;
N-(3-trifluoromethylphenyl)-N'-(2-bromo-5-methylthiophenyl)guanidine;
N-(3-bromophenyl)-N-methyl-N'-(2-chloro-5-methylthiophenyl)guanidine;
N-(3-bromophenyl)-N'-methyl-N'-(2-chloro-5-methylthiophenyl)guanidine;
N-(3-bromophenyl)-N'-(2-chloro-5-methylthiophenyl)guanidine;
N-(3-trifluoromethoxyphenyl)-N-methyl-N'-(2,5-dibromophenyl)guanidine;
N-(3-trifluoromethoxyphenyl)-N'-methyl-N'-(2,5-dibromophenyl)guanidine;
N-(3-trifluoromethoxyphenyl)-N'-(2,5-dibromophenyl)guanidine;
N-(3-trifluoromethoxyphenyl)-N-methyl-N'-(2-bromo-5-ethylphenyl)guanidine;
N-(3-trifluoromethoxyphenyl)-N'-methyl-N'-(2-bromo-5-ethylphenyl)guanidine;
N-(3-trifluoromethoxyphenyl)-N'-(2-bromo-5-ethylphenyl)guanidine;
N-(3-iodophenyl)-N-methyl-N'-(2-chloro-5-methylthiophenyl)guanidine;
N-(3-iodophenyl)-N'-methyl-N'-(2-chloro-5-methylthiophenyl)guanidine;
N-(3-iodophenyl)-N'-(2-chloro-5-methylthiophenyl)guanidine;
N-(3-iodophenyl)-N-methyl-N'-(2-chloro-5-ethylphenyl)guanidine;
N-(3-iodophenyl)-N'-methyl-N'-(2-chloro-5-ethylphenyl)guanidine;
N-(3-iodophenyl)-N'-(2-chloro-5-ethylphenyl)guanidine;
N-(3-ethylphenyl)-N'-(2-chloro-5-ethylthiophenyl)guanidine;
N-(3-ethylphenyl)-N-methyl-N'-(2-chloro-5-ethylthiophenyl)guanidine;
N-(3-ethylphenyl)-N'-methyl-N'-(2-chloro-5-ethylthiophenyl)guanidine;
N-(3-ethylphenyl)-N,N'-dimethyl-N'-(2-chloro-5-ethylthiophenyl)guanidine;
N-(3-ethylphenyl)-N'-(2-bromo-5-ethylthiophenyl)guanidine;
N-(3-ethylphenyl)-N-methyl-N'-(2-bromo-5-ethylthiophenyl)guanidine;
N-(3-ethylphenyl)-N'-methyl-N'-(2-bromo-5-ethylthiophenyl)guanidine;
N-(3-ethylphenyl)-N,N'-dimethyl-N'-(2-bromo-5-ethylthiophenyl)guanidine;
N-(3-methylthiophenyl)-N'-(2-chloro-5-ethylthiophenyl)guanidine;
N-(3-methylthiophenyl)-N-methyl-N'-(2-chloro-5-ethylthiophenyl)guanidine;
N-(3-methylthiophenyl)-N'-methyl-N'-(2-chloro-5-ethylthiophenyl)guanidine;

N-(3-methylthiophenyl)-N,N'-dimethyl-N'-(2-chloro-5-ethylthiophenyl)guanidine;
N-(3-methylthiophenyl)-N'-(2-bromo-5-ethylthiophenyl)guanidine;
N-(3-methylthiophenyl)-N-methyl-N'-(2-bromo-5-ethylthiophenyl)guanidine;
N-(3-methylthiophenyl)-N'-methyl-N'-(2-bromo-5-ethylthiophenyl)guanidine;
N-(3-methylthiophenyl)-N,N'-dimethyl-N'-(2-bromo-5-ethylthiophenyl)guanidine;
N-(3-trifluoromethylphenyl)-N'-(2-chloro-5-ethylthiophenyl)guanidine;
N-(3-trifluoromethylphenyl)-N-methyl-N'-(2-chloro-5-ethylthiophenyl)guanidine;
N-(3-trifluoromethylphenyl)-N'-methyl-N'-(2-chloro-5-ethylthiophenyl)guanidine;
N-(3-trifluoromethylphenyl)-N,N'-dimethyl-N'-(2-chloro-5-ethylthiophenyl)guanidine;
N-(3-trifluoromethylphenyl)-N'-(2-bromo-5-ethylthiophenyl)guanidine;
N-(3-trifluoromethylphenyl)-N-methyl-N'-(2-bromo-5-ethylthiophenyl)guanidine;
N-(3-trifluoromethylphenyl)-N'-methyl-N'-(2-bromo-5-ethylthiophenyl)guanidine;
N-(3-trifluoromethylphenyl)-N,N'-dimethyl-N'-(2-bromo-5-ethylthiophenyl)guanidine;
N-(3-ethylphenyl)-N'-(2-chloro-5-trifluoromethylthiophenyl)guanidine;
N-(3-ethylphenyl)-N-methyl-N'-(2-chloro-5-trifluoromethylthiophenyl)guanidine;
N-(3-ethylphenyl)-N'-methyl-N'-(2-chloro-5-trifluoromethylthiophenyl)guanidine;
N-(3-ethylphenyl)-N,N'-dimethyl-N'-(2-chloro-5-trifluoromethylthiophenyl)guanidine;
N-(3-ethylphenyl)-N'-(2-bromo-5-trifluoromethylthiophenyl)guanidine;
N-(3-ethylphenyl)-N-methyl-N'-(2-bromo-5-trifluoromethylthiophenyl)guanidine;
N-(3-ethylphenyl)-N'-methyl-N'-(2-bromo-5-trifluoromethylthiophenyl)guanidine;
N-(3-ethylphenyl)-N,N'-dimethyl-N'-(2-bromo-5-trifluoromethylthiophenyl)guanidine;
N-(3-methylthiophenyl)-N'-(2-chloro-5-trifluoromethylthiophenyl)guanidine;
N-(3-methylthiophenyl)-N-methyl-N'-(2-chloro-5-trifluoromethylthiophenyl)guanidine;
N-(3-methylthiophenyl)-N'-methyl-N'-(2-chloro-5-trifluoromethylthiophenyl)guanidine;
N-(3-methylthiophenyl)-N,N'-dimethyl-N'-(2-chloro-5-trifluoromethylthiophenyl)guanidine;
N-(3-methylthiophenyl)-N'-(2-bromo-5-trifluoromethylthiophenyl)guanidine;
N-(3-methylthiophenyl)-N-methyl-N'-(2-bromo-5-trifluoromethylthiophenyl)guanidine;
N-(3-methylthiophenyl)-N'-methyl-N'-(2-bromo-5-trifluoromethylthiophenyl)guanidine;
N-(3-methylthiophenyl)-N,N'-dimethyl-N'-(2-bromo-5-trifluoromethylthiophenyl)guanidine;
N-(3-trifluoromethylphenyl)-N'-(2-chloro-5-trifluoromethylthiophenyl)guanidine;
N-(3-trifluoromethylphenyl)-N-methyl-N'-(2-chloro-5-trifluoromethylthiophenyl)guanidine;
N-(3-trifluoromethylphenyl)-N'-methyl-N'-(2-chloro-5-trifluoromethylthiophenyl)guanidine;
N-(3-trifluoromethylphenyl)-N,N'-dimethyl-N'-(2-chloro-5-trifluoromethylthiophenyl)guanidine;
N-(3-trifluoromethylphenyl)-N'-(2-bromo-5-trifluoromethylthiophenyl)guanidine;
N-(3-trifluoromethylphenyl)-N-methyl-N'-(2-bromo-5-trifluoromethylthiophenyl)guanidine;
N-(3-trifluoromethylphenyl)-N'-methyl-N'-(2-bromo-5-trifluoromethylthiophenyl)guanidine; or
N-(3-trifluoromethylphenyl)-N,N'-dimethyl-N'-(2-bromo-5-trifluoromethylthiophenyl);guanidine;
N-(1-naphthyl)-N'-(2-bromo-5-ethylphenyl)guanidine;
N-(1-naphthyl-N'-(2-fluoro-5-ethylphenyl)guanidine;
N-(1-naphthyl)-N'-(2,5-dichlorophenyl)guanidine;
N-(1-naphthyl)-N'-(2,4,5-trichlorophenyl)guanidine;
N-(1-naphthyl)-N'-(2,3,5-trichlorophenyl)guanidine;
N-(1-naphthyl)-N'-(2,5-dichlorophenyl)-N'-methylguanidine;
N-(1-naphthyl)-N'-(2-chloro-5-methylphenyl)guanidine;
N-(1-naphthyl)-N'-(2,5-dimethylphenyl)guanidine;
N-(1-naphthyl)-N'-(2,5-dibromophenyl)guanidine;
N-(1-naphthyl)-N'-(2-chloro-5-methylphenyl)-N'-methylguanidine;
N-(1-naphthyl)-N'-(2,5-dimethylphenyl)-N'-methylguanidine;
N-(1-naphthyl)-N'-(2,5-dibromophenyl)-N-methylguanidine;
N-(1-naphthyl)-N'-(2,5-dibromophenyl)-N'-methylguanidine;
N-(1-naphthyl)-N'-(2-chloro-5-methylthiophenyl)guanidine;
N-(1-naphthyl)-N'-(2-fluoro-5-trifluoromethylphenyl)guanidine;
N-(1-naphthyl)-N'-(2-chloro-5-trifluoromethylphenyl)guanidine;
N-(1-naphthyl)-N'-(2-bromo-5-trifluoromethylphenyl)guanidine;
N-(1-naphthyl)-N'-(2-methylthio-5-trifluoromethylphenyl)guanidine;
N-(1-naphthyl)-N'-(2-methoxy-5-methylphenyl)guanidine;
N-(1-naphthyl)-N'-(2-chloro-5-ethylphenyl)guanidine;
N-(1-naphthyl)-N'-(2-chloro-5-ethylphenyl)-N'-methylguanidine;
N-(1-naphthyl)-N'-methyl-N'-(2-chloro-5-methylthiophenyl)guanidine;
N-(8-quinolinyl)-N'-(2-chloro-5-methylphenyl)guanidine;
N-(8-quinolinyl)-N'-(2-chloro-5-ethylphenyl)guanidine;
N-(8-quinolinyl)-N'-methyl-(2-chloro-5-ethylphenyl)guanidine;
N-(1-naphthyl)-N'-(2-fluoro-5-methylphenyl)guanidine;
N-(1-naphthyl)-N'-(2-chloro-5-methylthiophenyl)guanidine;
N-(1-naphthyl)-N'-(2-iodo-5-methylthiophenyl)guanidine; or
N-(1-naphthyl)-N'-(2-bromo-5-methylthiophenyl)guanidine; and pharmaceutically acceptable salts of said compounds.

25. A method of claim 4 wherein the compound is:

N-(3-methylsulfonylphenyl)-N-methyl-N'-(2,5-dibromophenyl)guanidine;

N-(3-methylsulfonylphenyl)-N'-methyl-N'-(2,5-dibromophenyl)guanidine;

N-(3-methylsulfonylphenyl)-N'-(2,5-dibromophenyl)guanidine;

N-(3-methylsulfinylphenyl)-N-methyl-N'-(2,5-dibromophenyl)guanidine;

N-(3-methylsulfinylphenyl)-N'-methyl-N'-(2,5-dibromophenyl)guanidine; or

N-(3-methylsulfinylphenyl)-N'-(2,5-dibromophenyl)guanidine; and pharmaceutically acceptable salts thereof.

26. A method of inhibiting NMDA receptor-ion channel related neurotoxicity in a mammal exhibiting such neurotoxicity or susceptible thereto comprising administering to the mammal an effective amount of a compound of the following formula:

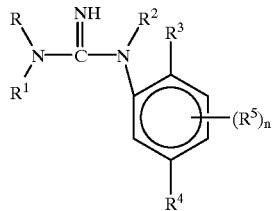

wherein R is substituted or unsubstituted carbocyclic aryl, substituted or unsubstituted aralkyl, or a substituted or unsubstituted heteroaromatic or heterocyclic group having 1 to 3 rings, 3 to 8 ring members in each ring and 1 to 3 heteroatoms;

$R^1$ and $R^2$ are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, substituted or unsubstituted aralkyl, or a substituted or unsubstituted heteroaromatic or heteroalcyclic group having 1 to 3 rings, 3 to 8 ring members in each ring and 1 to 3 hetero atoms;

$R^3$ $R^4$, and each $R^5$ substituent are each independently nitro, cyano, halogen, hydroxyl, azido, substituted or unsubstituted alkyl, substituted or unsubstituted alkenyl, substituted or unsubstituted alkynyl, substituted or unsubstituted alkanoyl, substituted or unsubstituted carboxyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, or substituted or unsubstituted aralkyl, with at least one of $R^3$, $R^4$, $R^5$ being nitro, cyano, substituted or unsubstituted alkanoyl or substituted or unsubstituted carboxyl; n is an integer of from 0–3; or a pharmaceutically acceptable salt thereof, with the exclusion of N-(2,4-di-iodo-5-hydxroxyphenyl)-N'-(2-tolyl)-guanidine and N-(2-methoxy-5-ethylphenyl)-N'-naphthylguanidine.

27. A method of claim 26 wherein the neurotoxicity is caused by hypoxia, hypoglycemia, brain or spinal cord ischemia or brain or spinal cord trauma.

28. A method of treating a mammal suffering from nerve cell death, stroke, heart attack, brain or spinal cord trauma, brain or spinal cord ischemia comprising administering to the mammal a treatment effective amount of the following formula:

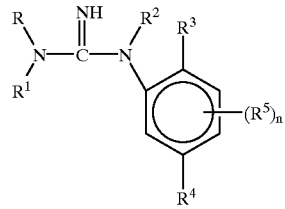

wherein R is substituted or unsubstituted carbocyclic aryl, substituted or unsubstituted aralkyl, or a substituted or unsubstituted heteroaromatic or heterocyclic group having 1 to 3 rings, 3 to 8 ring members in each ring and 1 to 3 heteroatoms;

$R^1$ and $R^2$ are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, substituted or unsubstituted aralkyl, or a substituted or unsubstituted heteroaromatic or heteroalicyclic group having 1 to 3 rings, 3 to 8 ring members in each ring and 1 to 3 hetero atoms;

$R^3$, $R^4$, and each $R^5$ substituent are each independently nitro, cyano, halogen, hydroxyl, azido, substituted or unsubstituted alkyl, substituted or unsubstituted alkenyl, substituted or unsubstituted alkynyl, substituted or unsubstituted alkanoyl, substituted or unsubstituted carboxyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, or substituted or unsubstituted aralkyl, with at least one of $R^3$, $R^4$, $R^5$ being nitro, cyano, substituted or unsubstituted alkanoyl or substituted or unsubstituted carboxyl; n is an integer of from 0–3; or a pharmaceutically acceptable salt thereof, with the exclusion of N-(2,4-di-iodo-5-hydroxyphenyl)-N'-(2-tolyl)-guanidine and N-(2-methoxy-5-ethylphenyl)-N'-naphthylguanidine.

29. A compound of any one of claims 1, 3, 4 or 14 wherein R is substituted or unsubstituted courmarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazol, tetrahydrofuranyl, tetrahydropyranyl, piperdinyl, morpholino, pyrrolindinyl or aralkyl having 1–3 separate or fused rings and from 6 to about 18 carbon ring atoms.

30. A compound of any one of claims 1, 3, 4 or 14 wherein the substituents may be optionally substituted by one or more halogen, cyano, hydroxyl, nitro, azido, alkanoyl, carboxamido, alkyl, alkenyl, alkynyl, alkoxy, aryloxy, alkylthio or aminoalkyl.

31. The method of claim 10 wherein the compound is N-(3-methylthiophenyl)-N-methyl-N'-(2-chloro-5-methylthiophenyl)guanidine or a pharmaceutically acceptable salt thereof.

32. The method of any one of claims 1, 3, 6, 7, 8, 9 or 10 wherein the compound is N-(3-methylphenyl)-N-methyl-N'-(2,5-dibromophenyl)guanidine or a pharmaceutically acceptable salt thereof.

33. A method of any one of claims 1, 2, 3, 4, 5, 6, 7, 8, 9, 10, 13, 14, 18, 19, 20, 21, 22, 23, 25, 26, 27, 28, or 31, wherein the compound is administered transdermally.

34. A method of claim 11 wherein the compound is administered transdermally.

35. A method of claim 12 wherein the compound is administered transdermally.

36. A method of claim 15 wherein the compound is administered transdermally.

37. A method of claim 16 wherein the compound is administered transdermally.

38. A method of claim 17 wherein the compound is administered transdermally.

39. A method of claim 24 wherein the compound is administered transdermally.

40. A method of claim 29 wherein the compound is administered transdermally.

41. A method of claim 30 wherein the compound is administered transdermally.

42. A method of claim 32 wherein the compound is administered transdermally.

* * * * *